US009084781B2

(12) United States Patent
Garraway et al.

(10) Patent No.: US 9,084,781 B2
(45) Date of Patent: Jul. 21, 2015

(54) MEK MUTATIONS CONFERRING RESISTANCE TO MEK INHIBITORS

(75) Inventors: Levi A. Garraway, Newton, MA (US); Caroline Emery, Brighton, MA (US); Carlos Garcia-Echeverria, Saint-Cloud (FR)

(73) Assignees: Novartis AG, Basel (CH); Dana-Farber Cancer Institute, Inc., Boston, MA (US)

(*) Notice: Subject to any disclaimer, the term of this patent is extended or adjusted under 35 U.S.C. 154(b) by 150 days.

(21) Appl. No.: 13/139,060

(22) PCT Filed: Dec. 10, 2009

(86) PCT No.: PCT/US2009/067472
§ 371 (c)(1),
(2), (4) Date: Aug. 31, 2011

(87) PCT Pub. No.: WO2010/068738
PCT Pub. Date: Jun. 17, 2010

(65) Prior Publication Data
US 2012/0015973 A1    Jan. 19, 2012

Related U.S. Application Data

(60) Provisional application No. 61/121,467, filed on Dec. 10, 2008, provisional application No. 61/180,739, filed on May 22, 2009.

(51) Int. Cl.
*C12Q 1/68* (2006.01)
*A61K 31/4184* (2006.01)
*C12N 9/12* (2006.01)
*A61K 38/00* (2006.01)

(52) U.S. Cl.
CPC .......... *A61K 31/4184* (2013.01); *C12N 9/1205* (2013.01); *A61K 38/00* (2013.01)

(58) Field of Classification Search
None
See application file for complete search history.

(56) References Cited

U.S. PATENT DOCUMENTS

| 4,582,788 A | 4/1986 | Erlich |
| 4,656,127 A | 4/1987 | Mundy |
| 4,659,774 A | 4/1987 | Webb et al. |
| 4,682,195 A | 7/1987 | Yilmaz |
| 4,683,194 A | 7/1987 | Saiki et al. |
| 4,683,202 A | 7/1987 | Mullis |
| 4,684,611 A | 8/1987 | Schilperoort et al. |
| 4,816,571 A | 3/1989 | Andrus et al. |
| 4,879,236 A | 11/1989 | Smith et al. |
| 4,946,773 A | 8/1990 | Maniatis et al. |
| 4,952,500 A | 8/1990 | Finnerty et al. |
| 4,959,463 A | 9/1990 | Froehler et al. |
| 5,096,676 A | 3/1992 | McPherson et al. |
| 5,141,813 A | 8/1992 | Nelson |
| 5,223,409 A | 6/1993 | Ladner et al. |
| 5,264,566 A | 11/1993 | Froehler et al. |
| 5,302,523 A | 4/1994 | Coffee et al. |
| 5,322,783 A | 6/1994 | Tomes et al. |
| 5,384,253 A | 1/1995 | Krzyzek et al. |
| 5,419,278 A | 5/1995 | Carter |
| 5,428,148 A | 6/1995 | Reddy et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,554,744 A | 9/1996 | Bhongle et al. |
| 5,563,055 A | 10/1996 | Townsend et al. |
| 5,574,146 A | 11/1996 | Reddy et al. |
| 5,580,859 A | 12/1996 | Felgner et al. |
| 5,589,466 A | 12/1996 | Felgner et al. |
| 5,591,616 A | 1/1997 | Hiei et al. |
| 5,602,244 A | 2/1997 | Caruthers et al. |
| 5,610,042 A | 3/1997 | Chang et al. |
| 5,645,897 A | 7/1997 | Andra |
| 5,650,298 A | 7/1997 | Bujard et al. |
| 5,656,610 A | 8/1997 | Shuler et al. |
| 5,702,932 A | 12/1997 | Hoy et al. |
| 5,705,629 A | 1/1998 | Bhongle |
| 5,736,524 A | 4/1998 | Content et al. |
| 5,780,448 A | 7/1998 | Davis |
| 5,789,215 A | 8/1998 | Berns et al. |
| 5,849,483 A | 12/1998 | Shuber |

(Continued)

FOREIGN PATENT DOCUMENTS

| AT | 404556 B | 12/1998 |
| AT | 277895 T | 10/2004 |
| AT | 302193 T | 9/2005 |
| AT | 302761 T | 9/2005 |
| AT | 309205 T | 11/2005 |
| AT | 310567 T | 12/2005 |
| AT | 311363 T | 12/2005 |
| AT | 344791 T | 11/2006 |
| AT | 383360 T | 1/2008 |
| AU | 2001273498 B2 | 1/2002 |

(Continued)

OTHER PUBLICATIONS

Emery et al (PNAS, 2009, 106(48): Abstract).*
Rodriguez-Viciana et al (Methods in Enzymology, 2008, 438: 277-289).*
Marks et al (Cancer Research, 2008, 68: 5524-5528).*
Sharma et al (Cancer Research, 2006, 66: 8200-8209).*

(Continued)

*Primary Examiner* — Sean Aeder
(74) *Attorney, Agent, or Firm* — Brinks Gilson & Lione

(57) ABSTRACT

The present invention relates to methods, compositions and kits concerning resistance to treatment with an anti-cancer agent, specifically an inhibitor of MEK. In particular embodiments, the invention concerns mutations in a MEK sequence that confer resistance to a MEK inhibitor. Identification of such mutations in a MEK sequence allows the identification and design of second-generation MEK inhibitors. Methods and kits for detecting the presence of a mutant MEK sequence in a sample are also provided.

13 Claims, 13 Drawing Sheets

(56) References Cited

U.S. PATENT DOCUMENTS

| | | |
|---|---|---|
| 5,851,770 A | 12/1998 | Babon et al. |
| 5,866,337 A | 2/1999 | Schon |
| 5,871,986 A | 2/1999 | Boyce |
| 5,925,525 A | 7/1999 | Fodor et al. |
| 5,928,870 A | 7/1999 | Lapidus et al. |
| 5,945,100 A | 8/1999 | Fick |
| 5,952,174 A | 9/1999 | Nikiforov et al. |
| 5,981,274 A | 11/1999 | Tyrrell et al. |
| 5,994,624 A | 11/1999 | Trolinder et al. |
| 6,054,273 A | 4/2000 | Housman |
| 6,200,754 B1 | 3/2001 | Housman et al. |
| 6,296,673 B1 | 10/2001 | Santarsiero et al. |
| 6,310,060 B1 | 10/2001 | Barrett et al. |
| 6,440,966 B1 | 8/2002 | Barrett et al. |
| 6,455,582 B1 | 9/2002 | Tecle |
| 6,469,004 B1 | 10/2002 | Barrett et al. |
| 6,492,363 B2 | 12/2002 | Barrett et al. |
| 6,506,798 B1 | 1/2003 | Barrett et al. |
| 6,545,030 B1 | 4/2003 | Barrett et al. |
| 6,750,217 B2 | 6/2004 | Barrett et al. |
| 6,770,778 B2 | 8/2004 | Barrett et al. |
| 6,821,963 B2 | 11/2004 | Barrett et al. |
| 6,835,749 B2 | 12/2004 | Tecle |
| 6,891,066 B2 | 5/2005 | Rewcastle et al. |
| 6,960,614 B2 | 11/2005 | Barrett et al. |
| 6,989,451 B2 | 1/2006 | Zhang et al. |
| 7,019,033 B2 | 3/2006 | Barrett et al. |
| 7,078,438 B2 | 7/2006 | Rewcastle et al. |
| 7,144,907 B2 | 12/2006 | Wallace et al. |
| 7,160,915 B2 | 1/2007 | Barrett et al. |
| 7,169,816 B2 | 1/2007 | Barrett et al. |
| 7,173,136 B2 | 2/2007 | Hennequin |
| 7,230,099 B2 | 6/2007 | Wallace et al. |
| 7,232,826 B2 | 6/2007 | Velaparthi et al. |
| 7,253,199 B2 | 8/2007 | Arkinstall et al. |
| 7,271,178 B2 | 9/2007 | Wallace et al. |
| 7,273,877 B2 | 9/2007 | Black et al. |
| 7,307,071 B2 | 12/2007 | Lyons et al. |
| 7,371,869 B2 | 5/2008 | Goodnow, Jr. et al. |
| 7,378,423 B2 | 5/2008 | Kawasaki et al. |
| 7,411,001 B2 | 8/2008 | Barrett et al. |
| 2002/0022647 A1 | 2/2002 | Barrett et al. |
| 2003/0004193 A1 | 1/2003 | Barrett et al. |
| 2003/0045521 A1 | 3/2003 | Tecle |
| 2003/0078428 A1 | 4/2003 | Barrett et al. |
| 2003/0092748 A1 | 5/2003 | Barrett et al. |
| 2003/0125359 A1 | 7/2003 | Lyons et al. |
| 2003/0149015 A1 | 8/2003 | Barrett et al. |
| 2003/0216460 A1 | 11/2003 | Wallace et al. |
| 2003/0232889 A1 | 12/2003 | Barrett et al. |
| 2004/0006245 A1 | 1/2004 | Rewcastle et al. |
| 2004/0039037 A1 | 2/2004 | Zhang et al. |
| 2004/0054172 A1 | 3/2004 | Barrett et al. |
| 2004/0092514 A1 | 5/2004 | Velaparthi et al. |
| 2004/0171632 A1 | 9/2004 | Gowan et al. |
| 2005/0004186 A1 | 1/2005 | Barrett et al. |
| 2005/0026964 A1 | 2/2005 | Black et al. |
| 2005/0026970 A1 | 2/2005 | Barrett et al. |
| 2005/0049276 A1 | 3/2005 | Kaufman et al. |
| 2005/0049419 A1 | 3/2005 | Wallace et al. |
| 2005/0049429 A1 | 3/2005 | Barrett et al. |
| 2005/0054701 A1 | 3/2005 | Wallace et al. |
| 2005/0054706 A1 | 3/2005 | Arkinstall et al. |
| 2005/0059710 A1 | 3/2005 | Barrett et al. |
| 2005/0130943 A1 | 6/2005 | Wallace et al. |
| 2005/0130976 A1 | 6/2005 | Wallace et al. |
| 2005/0137263 A1 | 6/2005 | Rewcastle et al. |
| 2005/0153942 A1 | 7/2005 | Wallace et al. |
| 2005/0176820 A1 | 8/2005 | Barrett et al. |
| 2005/0187247 A1 | 8/2005 | Berger et al. |
| 2005/0250782 A1 | 11/2005 | Marlow et al. |
| 2005/0256123 A1 | 11/2005 | Marlow et al. |
| 2005/0282856 A1 | 12/2005 | Hennequin |
| 2006/0014768 A1 | 1/2006 | Kawasaki et al. |
| 2006/0030610 A1 | 2/2006 | Koch et al. |
| 2006/0041146 A1 | 2/2006 | Chu et al. |
| 2006/0052608 A1 | 3/2006 | Barrett et al. |
| 2006/0063814 A1 | 3/2006 | Goodnow, Jr. et al. |
| 2006/0079526 A1 | 4/2006 | Wrasidlo et al. |
| 2006/0106225 A1 | 5/2006 | Wallace et al. |
| 2006/0189649 A1 | 8/2006 | Wallace et al. |
| 2006/0189668 A1 | 8/2006 | Wallace et al. |
| 2006/0189808 A1 | 8/2006 | Wallace et al. |
| 2006/0194802 A1 | 8/2006 | Abdellaoui et al. |
| 2006/0270643 A1 | 11/2006 | Chang et al. |
| 2007/0049591 A1 | 3/2007 | Pinkerton et al. |
| 2007/0105859 A1 | 5/2007 | Isshiki et al. |
| 2007/0112038 A1 | 5/2007 | Marlow et al. |
| 2007/0191346 A1 | 8/2007 | Hennequin |
| 2007/0197617 A1 | 8/2007 | Chen et al. |
| 2007/0238710 A1 | 10/2007 | Yan et al. |
| 2007/0244164 A1 | 10/2007 | Yan et al. |
| 2007/0287709 A1 | 12/2007 | Goutopoulos et al. |
| 2007/0287737 A1 | 12/2007 | Goutopoulos et al. |
| 2007/0293544 A1 | 12/2007 | Abel et al. |
| 2007/0293555 A1 | 12/2007 | Arkinstall et al. |
| 2007/0299103 A1 | 12/2007 | Abel et al. |
| 2008/0058340 A1 | 3/2008 | Maderna et al. |
| 2008/0081821 A1 | 4/2008 | Savy et al. |
| 2008/0085886 A1 | 4/2008 | Savy et al. |
| 2008/0166359 A1 | 7/2008 | Lamb |
| 2008/0188453 A1 | 8/2008 | Adams et al. |

FOREIGN PATENT DOCUMENTS

| | | |
|---|---|---|
| AU | 757046 B2 | 1/2003 |
| AU | 2002359291 B2 | 5/2003 |
| AU | 2002347360 A1 | 6/2003 |
| AU | 2002365665 A1 | 6/2003 |
| AU | 2002365899 B2 | 6/2003 |
| AU | 2003220202 A1 | 9/2003 |
| AU | 756586 C | 1/2004 |
| AU | 2003275282 A1 | 4/2004 |
| AU | 2003278369 A1 | 6/2004 |
| AU | 2003287366 A8 | 6/2004 |
| AU | 2003291268 A1 | 6/2004 |
| AU | 2003286306 A1 | 7/2004 |
| AU | 2004270699 A1 | 3/2005 |
| AU | 2004293018 A1 | 6/2005 |
| AU | 2004293019 A1 | 6/2005 |
| AU | 2005252110 B2 | 12/2005 |
| AU | 2005265769 A1 | 2/2006 |
| AU | 2005274390 A1 | 2/2006 |
| AU | 2005276974 A1 | 3/2006 |
| AU | 2005284293 A1 | 3/2006 |
| AU | 2005298932 A1 | 5/2006 |
| AU | 2005311451 A1 | 6/2006 |
| AU | 2006272837 A1 | 2/2007 |
| AU | 2006299902 A1 | 4/2007 |
| AU | 2006302415 A1 | 4/2007 |
| AU | 2008202731 A1 | 7/2008 |
| BR | 0317254 | 11/2005 |
| BR | 0412851 | 10/2006 |
| BR | 0414111 | 10/2006 |
| BR | 0416692 | 1/2007 |
| BR | 0511967 | 1/2008 |
| BR | 0513750 | 5/2008 |
| BR | 0514515 | 6/2008 |
| BR | 0515371 | 7/2008 |
| CA | 2 290 506 A1 | 1/1999 |
| CA | 2 290 509 A1 | 1/1999 |
| CA | 2 352 326 A1 | 6/2000 |
| CA | 2 349 467 A1 | 7/2000 |
| CA | 2 349 832 A1 | 7/2000 |
| CA | 2 355 374 A1 | 7/2000 |
| CA | 2 355 470 A1 | 7/2000 |
| CA | 2 416 685 A1 | 1/2002 |
| CA | 2 463 101 A1 | 5/2003 |
| CA | 2 466 762 A1 | 6/2003 |
| CA | 2 472 367 A1 | 7/2003 |
| CA | 2 473 545 A1 | 7/2003 |
| CA | 2 478 534 A1 | 9/2003 |
| CA | 2 509 405 A1 | 7/2004 |
| CA | 2 532 067 A1 | 2/2005 |

(56) References Cited

FOREIGN PATENT DOCUMENTS

| | | |
|---|---|---|
| CA | 2 537 321 A1 | 3/2005 |
| CA | 2 545 660 A1 | 6/2005 |
| CA | 2 546 353 A1 | 6/2005 |
| CA | 2 569 850 A1 | 12/2005 |
| CA | 2 575 232 A1 | 2/2006 |
| CA | 2 576 599 A1 | 2/2006 |
| CA | 2 578 283 A1 | 3/2006 |
| CA | 2 579 130 A1 | 3/2006 |
| CA | 2 582 247 A1 | 5/2006 |
| CA | 2 586 796 A1 | 6/2006 |
| CA | 2 587 178 A1 | 6/2006 |
| CA | 2 618 218 A1 | 2/2007 |
| CA | 2 608 201 A1 | 4/2007 |
| CA | 2 622 755 A1 | 4/2007 |
| CN | 1652792 A | 8/2005 |
| CN | 1874769 A | 12/2006 |
| CN | 1905873 A | 1/2007 |
| CN | 101006085 A | 7/2007 |
| CN | 101006086 A | 7/2007 |
| CN | 101023079 A | 8/2007 |
| CN | 101044125 A | 9/2007 |
| CN | 101065358 A | 10/2007 |
| CN | 101124199 A | 2/2008 |
| EE | 200100339 A | 10/2002 |
| EE | 200100373 A | 10/2002 |
| EE | 200100374 A | 12/2002 |
| EE | 200300030 A | 10/2004 |
| EP | 0 050 424 A1 | 4/1982 |
| EP | 0 084 796 B1 | 8/1983 |
| EP | 0 201 184 A2 | 12/1986 |
| EP | 0 237 362 A1 | 9/1987 |
| EP | 0 266 032 A1 | 5/1988 |
| EP | 1 438 295 A2 | 7/2004 |
| EP | 0 993 439 B1 | 9/2004 |
| EP | 1 467 965 A2 | 10/2004 |
| EP | 1 467 968 A2 | 10/2004 |
| EP | 0 258 017 B2 | 12/2004 |
| EP | 1 482 944 A2 | 12/2004 |
| EP | 1 545 529 A2 | 6/2005 |
| EP | 1 144 385 B1 | 8/2005 |
| EP | 1 144 394 B1 | 8/2005 |
| EP | 1 575 943 A1 | 9/2005 |
| EP | 1 578 346 A2 | 9/2005 |
| EP | 1 578 736 A1 | 9/2005 |
| EP | 1 140 291 B1 | 11/2005 |
| EP | 1 144 371 B1 | 11/2005 |
| EP | 1 144 372 B1 | 11/2005 |
| EP | 1 673 339 A2 | 6/2006 |
| EP | 1 674 452 A1 | 6/2006 |
| EP | 1 682 138 A2 | 7/2006 |
| EP | 1 689 233 A2 | 8/2006 |
| EP | 0 993 437 B1 | 11/2006 |
| EP | 1 780 197 A1 | 5/2007 |
| EP | 1 799 656 A1 | 6/2007 |
| EP | 1 802 579 A1 | 7/2007 |
| EP | 1 838 675 A1 | 10/2007 |
| EP | 1 761 528 B1 | 1/2008 |
| EP | 1 894 932 A1 | 3/2008 |
| EP | 1 912 636 A2 | 4/2008 |
| EP | 1 922 307 A2 | 5/2008 |
| EP | 1 781 649 B1 | 8/2008 |
| EP | 1 966 155 A1 | 9/2008 |
| EP | 1 967 516 A1 | 9/2008 |
| EP | 1 791 837 B1 | 8/2009 |
| EP | 1 651 214 B1 | 9/2009 |
| EP | 1 828 184 B1 | 9/2009 |
| EP | 1 934 174 B1 | 4/2011 |
| ES | 2 229 515 T3 | 4/2005 |
| ES | 2 247 859 T3 | 3/2006 |
| ES | 2 249 060 T3 | 3/2006 |
| ES | 2 251 851 T3 | 5/2006 |
| ES | 2 252 996 T3 | 5/2006 |
| FR | 2 650 840 A1 | 2/1991 |
| GB | 2323845 | 10/1998 |
| JP | 2000-204075 A | 7/2000 |
| JP | 2000-204077 A | 7/2000 |
| JP | 2000-204079 A | 7/2000 |
| JP | 2000-212157 A | 8/2000 |
| JP | 2002-509536 A | 3/2002 |
| JP | 2002-511092 A | 4/2002 |
| JP | 2002-532570 A | 10/2002 |
| JP | 2002-534497 A | 10/2002 |
| JP | 2002-534510 A | 10/2002 |
| JP | 2002-534515 A | 10/2002 |
| JP | 2004-504294 A | 2/2004 |
| JP | 2004-093459 A | 3/2004 |
| JP | 2004-115474 A | 4/2004 |
| JP | 2005-508972 A | 4/2005 |
| JP | 2005-515251 A | 5/2005 |
| JP | 2005-515253 A | 5/2005 |
| JP | 2005-526008 A | 9/2005 |
| JP | 2005-526076 A | 9/2005 |
| JP | 2006-083133 A | 3/2006 |
| JP | 2006-508944 A | 3/2006 |
| JP | 2006-516967 A | 7/2006 |
| JP | 3811775 B2 | 8/2006 |
| JP | 2006-528621 A | 12/2006 |
| JP | 2007-504241 A | 3/2007 |
| JP | 2007-511614 A | 5/2007 |
| JP | 2007-511615 A | 5/2007 |
| JP | 2008-501631 A | 1/2008 |
| JP | 2008-509950 A | 4/2008 |
| JP | 2008-510839 A | 4/2008 |
| JP | 2008-513397 A | 5/2008 |
| JP | 2008-517024 A | 5/2008 |
| JP | 4090070 B2 | 5/2008 |
| JP | 2008-520615 A | 6/2008 |
| JP | 2008-521858 A | 6/2008 |
| JP | 4131741 B2 | 8/2008 |
| JP | 2008-201788 A | 9/2008 |
| KR | 10-2007-026343 | 3/2007 |
| KR | 10-2007-034581 | 3/2007 |
| KR | 10-2007-034635 | 3/2007 |
| KR | 10-2007-041752 | 4/2007 |
| KR | 10-2007-043895 | 4/2007 |
| KR | 10-2007-067727 | 6/2007 |
| KR | 10-2008-019236 | 3/2008 |
| KR | 10-2008-050601 | 6/2008 |
| KR | 10-2008-068637 | 7/2008 |
| RU | 2300528 C2 | 6/2007 |
| TR | 2001 01871 T2 | 10/2001 |
| TR | 2001 02029 T2 | 11/2001 |
| TR | 2001 02030 T2 | 1/2002 |
| TW | 396149 B | 7/2000 |
| TW | 592692 B | 6/2004 |
| WO | WO 91-02087 A1 | 2/1991 |
| WO | WO 92-15712 A1 | 9/1992 |
| WO | WO 94-09699 A1 | 5/1994 |
| WO | WO 95-06128 A2 | 3/1995 |
| WO | WO 99-01421 A1 | 1/1999 |
| WO | WO 99-01426 A1 | 1/1999 |
| WO | WO 00-37141 A1 | 6/2000 |
| WO | WO 00-41994 A1 | 7/2000 |
| WO | WO 00-42002 A1 | 7/2000 |
| WO | WO 00-42003 A1 | 7/2000 |
| WO | WO 00-42022 A1 | 7/2000 |
| WO | WO 00-42029 A1 | 7/2000 |
| WO | WO 02-06213 A2 | 1/2002 |
| WO | WO 03-035626 A2 | 5/2003 |
| WO | WO 03-047523 A2 | 6/2003 |
| WO | WO 03/047523 A2 * | 6/2003 |
| WO | WO 03-047583 A1 | 6/2003 |
| WO | WO 03-047585 A1 | 6/2003 |
| WO | WO 03-062189 A1 | 7/2003 |
| WO | WO 03-062191 A1 | 7/2003 |
| WO | WO 03-077855 A2 | 9/2003 |
| WO | WO 2004-030620 A1 | 4/2004 |
| WO | WO 2004-041185 A2 | 5/2004 |
| WO | WO 2004-041811 A1 | 5/2004 |
| WO | WO 2004-044219 A2 | 5/2004 |
| WO | WO 2004-056789 A1 | 7/2004 |
| WO | WO 2005-000818 A1 | 1/2005 |
| WO | WO 2005-007616 A1 | 1/2005 |
| WO | WO 2005-009975 A2 | 2/2005 |

(56) References Cited

FOREIGN PATENT DOCUMENTS

| | | |
|---|---|---|
| WO | WO 2005-023759 A2 | 3/2005 |
| WO | WO 2005-028426 A1 | 3/2005 |
| WO | WO 2005-051301 A2 | 6/2005 |
| WO | WO 2005-051302 A2 | 6/2005 |
| WO | WO 2005-082891 A1 | 9/2005 |
| WO | WO 2005-121142 A1 | 12/2005 |
| WO | WO 2006-011466 A1 | 2/2006 |
| WO | WO 2006-018188 A2 | 2/2006 |
| WO | WO 2006-024034 A1 | 3/2006 |
| WO | WO 2006-024836 A1 | 3/2006 |
| WO | WO 2006-029862 A1 | 3/2006 |
| WO | WO 2006-045514 A1 | 5/2006 |
| WO | WO 2006-056427 A1 | 6/2006 |
| WO | WO 2006-058752 A1 | 6/2006 |
| WO | WO 2006-133417 A1 | 12/2006 |
| WO | WO 2007-014011 A2 | 2/2007 |
| WO | WO 2007-025090 A2 | 3/2007 |
| WO | WO 2007-044084 A2 | 4/2007 |
| WO | WO 2007-044515 A1 | 4/2007 |
| WO | WO 2007-071951 A1 | 6/2007 |
| WO | WO 2007-096259 A1 | 8/2007 |
| WO | WO 2007-121269 A2 | 10/2007 |
| WO | WO 2007-121481 A2 | 10/2007 |
| WO | WO 2007-123936 A1 | 11/2007 |
| WO | WO 2007-123939 A2 | 11/2007 |
| WO | WO 2008-020203 A1 | 2/2008 |
| WO | WO 2008-021389 A2 | 2/2008 |
| WO | WO 2008-024724 A1 | 2/2008 |
| WO | WO 2008-024725 A1 | 2/2008 |
| WO | WO 2008-028141 A2 | 3/2008 |
| WO | WO 2008-055236 A2 | 5/2008 |
| WO | WO 2008-067481 A1 | 6/2008 |
| WO | WO 2008-076415 A1 | 6/2008 |
| WO | WO 2008/120004 A1 | 10/2008 |
| WO | WO 2008-120004 A1 | 10/2008 |
| ZA | 98-05726 | 6/1998 |
| ZA | 98-05728 | 6/1998 |
| ZA | 2001-005219 | 6/2001 |
| ZA | 2001-005224 | 6/2001 |

OTHER PUBLICATIONS

Marks et al (Cancer Research, 2006, 68: 5524-5528).*
Estep et al (PLoS one, 2007, 12 (e1279): 1-7).*
Bentivegna et al (Hum Mutat, 2008, 29(3): 441-450).*
Narumi et al (American Journal of Medical Genetics, 2007, 143A:799-807).*
Nyström et al., "Noonan and cardio-facio-cutaneous syndromes: two clinically and genetically overlapping disorders," J. Med. Genet., vol. 45, No. 8, pp. 500-506, Apr. 24, 2008, Uppsala, Sweden.
Decision to Grant a Patent mailed Nov. 5, 2014 for Japanese Patent Application No. 2011-540884.
Boobbyer, D. N. A. et al., "New Hydrogen-Bond Potentials for Use in Determining Energetically Favorable Binding Sites on Molecules of Known Structure," Journal of Medical Chemistry, vol. 32, No. 5, 1989, pp. 1083-1094.
Brünger A. T. et al, "Solution of a Protein Crystal Structure with a Model Obtained from NMR Interproton Distance Restraints," Science, vol. 235, 1987, pp. 1049-1053.
Brünger A. T. et al., "Crystallography & NMR System: A New Software Suite for Macromolecular Structure Determination," Acta Crystallography, vol. D54, 1998, pp. 905-921.
Carbonelli, D. L. et al., "A Plasmid Vector for Isolation of Strong Promoters in *Escherichia Coli*," FEMS Microbiology Letters, vol. 177, 1999, pp. 75-82.
Carell, T. et al., "A Novel Procedure for the Synthesis of Libraries Containing Small Organic Molecules," Angewandte Chemie International Edition Engl., vol. 33, No. 20, 1994, pp. 2059-2061.
Carell T. et al., "A Solution-Phase Screening Procedure for the Isolation of Active Compounds from a Library of Molecules," Angewandte Chemie International Edition Engl., vol. 33, No. 20, 1994, pp. 2061-2064.
Chandler, S. D. et al., "RNA Splicing Specificity Determined by the Coordinated Action of RNA Recognition Motifs in SR Proteins," Proceedings of the National Academy of Sciences of the United States of America, vol. 94, 1997, pp. 3596-3601.
Chen, C. et al., "High-Efficiency Transformation of Mammalian Cells by Plasmid DNA," Molecular and Cellular Biology, vol. 7, No. 8, 1987, pp. 2745-2752.
Chou, T. C. et al., Abstract of "Quantitative Analysis of Dose-Effect Relationships: The Combined Effects of Multiple Drugs or Enzyme Inhibitors," Advances in Enzyme Regulation, vol. 22, 1984, pp. 27-55.
Cocea, L. "Duplication of a Region in the Multiple Cloning Site of a Plasmid Vector to Enhance Cloning-Mediated Addition of Restriction Sites to a DNA Fragment," BioTechniques, vol. 23, No. 5, 1997, pp. 814-816.
Cull, M. G. et al., "Screening for receptor ligands using large libraries of peptides linked to the C terminus of the *lac* repressor," Proceedings of the National Academy of Sciences of the United States of America, vol. 89, 1992, pp. 1865-1869.
Cwirla, S. E. et al., "Peptides on Phage: A Vast Library of Peptides for Identifying Ligands," Proceedings of the National Academy of Sciences of the United States of America, vol. 87, 1990, pp. 6378-6382.
DesJarlias, R. L. et al., "Using Shape Complemenarity as an Initial Screen in Designing Lignads for a Receptor Binding Site of Known Three-Dimensional Structure," Journal of Medicinal Chemistry, vol. 31, No. 4, 1988, pp. 722-729.
Devlin, J. J. et al., "Random Peptide Libraries: A Source of Specific Protein Binding Molecules," Science, vol. 249, 1990, pp. 404-406.
Drenth, J., Ch. 1, "Crystallizing a Protein," Principles of Protein X-ray Crystallography, New York: Springer-Verlag, copyright 1994, pp. 1-19.
Emery, C. M. et al., "MEK1 mutations confer resistance to MEK and B-RAF inhibition," Proceedings of the National Academy of Sciences of the United States of America, vol. 106, No. 48, 2009, pp. 20411-20416.
Erb, E. et al., "Recursive Deconvolution of Combinatorial Chemical Libraries," Proceedings of the National Academy of Sciences of the United States of America, vol. 91, 1994, pp. 11422-11426.
Estep, A. L. et al., "Mutation Analysis of BRAF, MEK1 and MEK2 in 15 Ovarian Cancer Cell Lines: Implications for Therapy," PLoS One, vol. 2, No. 12, 2007, e1279, 7 pages.
Fechheimer, M. et al., "Transfection of Mammalian Cells with Plasmid DNA by Scrape Loading and Sonication Loading," Proceedings of the National Academy of Sciences of the United States of America, vol. 84, 1987, pp. 8463-8467.
Felici, F. et al., "Selection of Antibody Ligands from a Large Library of Oligopeptides Expressed on a Multivalent Exposition Vector," Journal of Molecular Biology, vol. 222, 1991, pp. 301-310.
Fodor, S. P. A. et al., "Multiplexed Biochemical Assays with Biological Chips," Nature, vol. 364, 1993, pp. 555-556.
Fraley, R. T. et al., "Entrapment of a Bacterial Plasmid in Phospholipid Vesicles: Potential for Gene Transfer," Proceedings of the National Academy of Sciences of the United States of America, vol. 76, No. 7, 1979, pp. 3348-3352.
Friday, B. B. et al., "Advances in Targeting the Ras/Raf/Erk Mitogen-Activated Protein Kinase Cascade with MEK Inhibitors for Cancer Therapy," Clinical Cancer Research vol. 14, No. 2, 2008, pp. 342-346.
Froehler, B. C. et al., "Synthesis of DNA Via Deoxynucleoside H-phosphonate Intermediates," Nucleic Acids Research, vol. 14, No. 13, 1986, pp. 5399-5407.
Gallop, M. A. et al., "Applications of Combinatorial Technologies to Drug Discovery. 1. Background and Peptide Combinatorial Libraries," Journal of Medical Chemistry, vol. 37, No. 9, 1994, pp. 1233-1251.
Geromichalos, G. D., "Importance of Molecular Computer Modeling in Anitcancer Drug Development," Journal of Balkan Union of Oncology (BUON), vol. 12, Suppl. 1, 2007, pp. S101-S118.
Goodford, P. J. et al., "A Computational Procedure for Determining Energetically Favorable Binding Sites on Biologically Important Macromolecules," (1985) Journal of Medicinal Chemistry, vol. 28, pp. 849-857.

(56) References Cited

OTHER PUBLICATIONS

Gopal, T. V., "Gene Transfer Method for Transient Gene Expression, Stable Transformation, and Cotransformation of Suspension Cell Cultures," Molecular and Cellular Biology, vol. 5, No. 5, 1985, pp. 1188-1190.
Gossen, M. et al., "Tight control of gene expression in mammalian cells by tetracycline-responsive promoters," Proceedings of the National Academy of Sciences of the United States of America, vol. 89, 1992, pp. 5547-5551.
Gossen, M. et al., "Transcriptional Activation by Tetracyclines in Mammalian Cells," Science, vol. 268, 1995, pp. 1766-1769.
Graham, F. L. et al., "A New Technique for the Assay of Infectivity of Human Adenovirus 5 DNA," Virology, vol. 52, 1973, pp. 456-467.
Harland, R. et al., "Translation of mRNA Injected into Xenopus Oocytes Is Specifically Inhibited by Antisense RNA," Journal of Cell Biology, vol. 101, 1985, pp. 1094-1099.
Ho, C. M. W. et al., "Cavity Search: An Algorithm for the Isolation and Display of Cavity-Like Binding Regions," Journal of Computer-Aided Molecular Design, vol. 4, 1990, pp. 337-354.
Holford, N. H. G. et al., "Understanding the Does-Effect Relationship: Clinical Application of Pharmacokinetic-Pharmacodynamic Models," Clinical Pharmacokinetics, vol. 6, 1981, pp. 429-453.
Horwell, D. et al., "'Targeted' Molecular Diversity: Design and Development of Non-Peptide Antagonists for Cholecystokinin and Tachykinin Receptors," Immunopharmacology, vol. 33, 1996, pp. 68-72.
Houghten, R. A. et al., "The Use of Synthetic Peptide Combinatorial Libraries for the Identification of Bioactive Peptides," BioTechniques, vol. 13, No. 3, 1992, pp. 412-421.
International Search Report dated Feb. 17, 2010 for International Application No. PCT/US2009/067472, 3 pages.
Kaeppler H. F. et al., "Silicon Carbide Fiber-Mediated DNA Delivery Into Plant Cells," Plant Cell Reports, vol. 9, 1990, pp. 415-418.
Kaneda, Y. et al., "Increased Expression of DNA Cointroduced with Nuclear Protein in Adult Rat Liver," Science, vol. 243, 1989, pp. 375-378.
Kato, K. et al., "Expression of Hepatitis B Virus Surface Antigen in Adult Rat Liver," Journal of Biological Chemistry, vol. 266, No. 6, 1991, pp. 3361-3364.
Katsoulis, IE et al., "Endoscopic Palliation of Malignant Dysphagia: A Challenging Task in Inoperable Oesophageal Cancer," World Journal of Surgical Oncology, vol. 4, 2006, 5 pages.
Kornher, J. S. et al., "Mutation Detection Using Nucleotide Analogs that Alter Electrophoretic Mobility," Nucleic Acids Research, vol. 17, No. 19, 1989, pp. 7779-7784.
Kuppuswamy, M. N. et al., "Single Nucleotide Primer Extension to Detect Genetic Diseases: Experimental Application to Hemophilia B (Factor IX) and Cystic Fibrosis Genes," Proceedings of the National Academy of Sciences of the United States of America, vol. 88, pp. 1143-1147.
Lam, K.S. et al., "A New Type of Synthetic Peptide Library for Identifying Ligand-Binding Activity," Nature, vol. 354, 1991, pp. 82-84.
Lam, K.S., Abstract of "Application of Combinatorial Library Methods in Cancer Research and Drug Discovery," Anticancer Drugs Design, vol. 12, No. 3, 1997, pp. 145-167.
Landegren et al., "A Ligase-Mediated Gene Detection Technique," Science, vol. 241, 1988, pp. 1077-1080.
Levenson, V. V. et al., "Internal Ribosomal Entry Site-Containing Retroviral Vectors with Green Fluorescent Protein and Drug Resistance Markers," Human Gene Therapy, vol. 9, 1998, pp. 1233-1236.
Mallon, R. et al., "Identification of 4-anilino-3-quinolinecarbonitrile inhibitors of mitogen-activated protein/extracellular signal-regulated kinase 1 kinase," Molecular Cancer Therapeutics, vol. 3, No. 6, 2004, pp. 755-762.
Maxam, A. M., et al., "A New Method for Sequencing DNA," Proceedings of the National Academy of Sciences of the United States of America, vol. 74, No. 2, pp. 560-564, (1991).

Meng, E. C. et al., "Automated Docking with Grid-Based Energy Evaluation," Journal of Computational Chemistry, vol. 13, No. 4, 1992, pp. 505-524.
Meng, E. C. et al., "Orientational Sampling and Rigid-Body Minimization in Molecular Docking," Proteins: Structure, Function, and Genetics, vol. 17, 1993, pp. 266-278.
Mullis, K. et al., "Specific Enzymatic Amplification of DNA In Vitro: The Polymerase Chain Reaction," Cold Spring Harbor Symposia on Quantitative Biology, vol. 51, 1986, pp. 263-273.
Narula, S. S. et al., "Solution structure of the C-terminal SH2 domain of the human tyrosine kinase Syk complexed with a phosphotyrosine pentapeptide," Structure, vol. 3, No. 10, 1995, pp. 1061-1073.
Nickerson, D. A. et al., "Automated DNA Diagnostics Using an ELISA-based Oligonucleotide Ligation Assay," Proceedings of the National Academy of Sciences of the United States of America, vol. 87, 1990, pp. 8923-8927.
Nicolau, C. et al., "Liposome-Mediated DNA Transfer in Eukaryotic Cells. Dependence of the Transfer Efficiency Upon the Type of Liposomes Used and the Host Cell Cycle Stage," Biochimica et Biobhysica Acta, vol. 721, 1982, pp. 185-190.
Nicolau, C. et al., "Liposomes as Carriers for in Vivo Gene Transfer and Expression," Methods in Enzymology, vol. 149, 1987, pp. 157-176.
Nyrén, P. et al., "Solid Phase DNA Minisequencing by an Enzymatic Luminometric Inorganic Pryophosphate Detection Assay," Analytical Biochemistry, vol. 208, 1993, pp. 171-175.
Nyström, A-M et al., "Noonan and cardio-facio-cutaneous syndromes: two clinically and genetically overlapping disorders," Journal of Medical Genetics, vol. 45, 2008, pp. 500-506.
Omirulleh, S. et al., "Activity of a Chimeric Promoter with the Doubled CaMV 35S Enhancer Element in Protoplast-Derived Cells and Transgenic Plains in Maize," Plant Molecular Biology, vol. 21, 1993, pp. 415-428.
Potrykus, I. et al., "Molecular and General Genetics of a Hybrid Foreign Gene Introduced into Tobacco by Direct Gene Transfer," Molecular and General Genetics, vol. 199, 1985, pp. 169-177.
Prezant, T. R. et al., "Trapped-Oligonucleotide Nucleotide Incorporation (TONI) Assay, a Simple Method for Screening Point Mutations," Human Mutation, vol. 1, 1992, pp. 159-164.
Rippe, R. A. et al., "DNA-Mediated Gene Transfer into Adult Rat Hepatocytes in Primary Culture," Molecular and Cellular Biology, vol. 10, No. 2, 1990, pp. 689-695.
Sanger, F., et al., Abstract of "A Rapid Method for Determining Sequences in DNA by Primed Synthesis with DNA Polymerase," Journal of Molecular Biology, vol. 94, No. 3, 1975, pp. 441-446.
Scott, J. K., et al., "Searching for Peptide Ligands with an Epitope Library," Science, 1990, vol. 249, pp. 386-390.
Shoichet, B. K. et al., "Structure-Based Discovery of Inhibitors of Thymidylate Synthase," Science, 1993, vol. 259, pp. 1445-1450.
Sokolov, B. P., "Primer Extension Technique for the Detection of Single Nucleotide in Genomic DNA," Nucleic Acids Research, vol. 18, No. 12, 1989, pp. 3671.
Stevens, R. C. et al., "High-throughput protein crystallization," Current Opinion in Structural Biology, vol. 10, 2000, pp. 558-563.
Syvänen, A-C. et al., "Identification of Individuals by Analysis of Biallelic DNA Markers, Using PCR and Solid-Phase Minisequencing," American Journal of Human Genetics, vol. 52, 1993, pp. 46-59.
Syvänen, A-C. et al., "A Primer-Guided Nucleotide Incorporation Assay in the Genotyping of Apolipoprotein E," Genomics, vol. 8, 1990, pp. 684-692.
Ugozzolli, L. et al., "Detection of Specific Alleles by Using Allele-Specific Primer Extension Followed by Capture on Solid Support," Genetic Analysis, Techniques and Applications, vol. 9, No. 4, 1992, pp. 107-112.
Wong, T-K. et al., "Appearance of β-lactamase activity in animal cells upon liposome-mediated gene transfer," Gene, vol. 10, 1980, pp. 87-94.
Zhang, N. et al., "MEK (MAPKK) Inhibitors. Part 2: Structure-Activity Relationships of 4-Anilino-3cyano-6,7-dialkoxyquinolines," Bioorganic & Medicinal Chemistry Letters, vol. 11, 2001, pp. 1407-1410.

* cited by examiner

Wild-type Human MEK1 Nucleic Acid Sequence (SEQ ID NO:1) (NM_002755; gi:169790828)

```
AGGCGAGGCTTCCCCTTCCCCGCCCCTCCCCGGCCTCCAGTCCCTCCCAGGGC
CGCTTCGCAGAGCGGCTAGGAGCACGGCGGCGGCGGCACTTTCCCCGGCAGGAG
CTGGAGCTGGGCTCTGGTGCGCGCGCGGCTGTGCCGCCCGAGCCGGAGGGACTG
GTTGGTTGAGAGAGAGAGAGGAAGGGAATCCCGGGCTGCCGAACCGCACGTTCAG
CCCGCTCCGCTCCTGCAGGGCAGCCTTTCGGCTCTCTGCGCGCGAAGCCGAGTCC
CGGGCGGGTGGGGCGGGGGTCCACTGAGACCGCTACCGGCCCCTCGGCGCTGAC
GGGACCGCGCGGGGCGCACCCGCTGAAGGCAGCCCCGGGGCCCGCGGCCCGGA
CTTGGTCCTGCGCAGCGGGCGCGGGGCAGCGCAGCGGGAGGAAGCGAGAGGTG
CTGCCCTCCCCCCGGAGTTGGAAGCGCGTTACCCGGGTCCAAAATGCCCAAGAAG
AAGCCGACGCCCATCCAGCTGAACCCGGCCCCCGACGGCTCTGCAGTTAACGGGA
CCAGCTCTGCGGAGACCAACTTGGAGGCCTTGCAGAAGAAGCTGGAGGAGCTAGA
GCTTGATGAGCAGCAGCGAAAGCGCCTTGAGGCCTTTCTTACCCAGAAGCAGAAG
GTGGGAGAACTGAAGGATGACGACTTTGAGAAGATCAGTGAGCTGGGGGCTGGCA
ATGGCGGTGTGGTGTTCAAGGTCTCCCACAAGCCTTCTGGCCTGGTCATGGCCAG
AAAGCTAATTCATCTGGAGATCAAACCCGCAATCCGGAACCAGATCATAAGGGAGC
TGCAGGTTCTGCATGAGTGCAACTCTCCGTACATCGTGGGCTTCTATGGTGCGTTC
TACAGCGATGGCGAGATCAGTATCTGCATGGAGCACATGGATGGAGGTTCTCTGGA
TCAAGTCCTGAAGAAAGCTGGAAGAATTCCTGAACAAATTTTAGGAAAAGTTAGCAT
TGCTGTAATAAAAGGCCTGACATATCTGAGGGAGAAGCACAAGATCATGCACAGAG
ATGTCAAGCCCTCCAACATCCTAGTCAACTCCCGTGGGGAGATCAAGCTCTGTGAC
TTTGGGGTCAGCGGGCAGCTCATCGACTCCATGGCCAACTCCTTCGTGGGCACAA
GGTCCTACATGTCGCCAGAAAGACTCCAGGGGACTCATTACTCTGTGCAGTCAGAC
ATCTGGAGCATGGGACTGTCTCTGGTAGAGATGGCGGTTGGGAGGTATCCCATCC
CTCCTCCAGATGCCAAGGAGCTGGAGCTGATGTTTGGGTGCCAGGTGGAAGGAGA
TGCGGCTGAGACCCCACCCAGGCCAAGGACCCCCGGGAGGCCCCTTAGCTCATAC
GGAATGGACAGCCGACCTCCCATGGCAATTTTTGAGTTGTTGGATTACATAGTCAA
CGAGCCTCCTCCAAAACTGCCCAGTGGAGTGTTCAGTCTGGAATTTCAAGATTTTGT
GAATAAATGCTTAATAAAAAACCCCGCAGAGAGCAGATTTGAAGCAACTCATGGT
TCATGCTTTTATCAAGAGATCTGATGCTGAGGAAGTGGATTTTGCAGGTTGGCTCTG
CTCCACCATCGGCCTTAACCAGCCCAGCACACCAACCCATGCTGCTGGCGTCTAA
GTGTTTGGGAAGCAACAAAGAGCGAGTCCCCTGCCCGGTGGTTTGCCATGTCGCTT
TTGGGCCTCCTTCCCATGCCTGTCTCTGTTCAGATGTGCATTTCACCTGTGACAAAG
GATGAAGAACACAGCATGTGCCAAGATTCTACTCTTGTCATTTTAATATTACTGTCT
TTATTCTTATTACTATTATTGTTCCCCTAAGTGGATTGGCTTTGTGCTTGGGGCTATT
TGTGTGTATGCTGATGATCAAAACCTGTGCCAGGCTGAATTACAGTGAAATTTTGGT
GAATGTGGGTAGTCATTCTTACAATTGCACTGCTGTTCCTGCTCCATGACTGGCTGT
CTGCCTGTATTTTCGGGATTCTTTGACATTTGGTGGTACTTTATTCTTGCTGGGCAT
ACTTTCTCTAGGAGGGAGCCTTGTGAGATCCTTCACAGGCAGTGCATGTGAAGC
ATGCTTTGCTGCTATGAAAATGAGCATCAGAGAGTGTACATCATGTTATTTTATTATT
ATTATTTGCTTTTCATGTAGAACTCAGCAGTTGACATCCAAATCTAGCCAGAGCCCT
TCACTGCCATGATAGCTGGGCTTCACCAGTCTGTCTACTGTGGTGATCTGTAGAC
TTCTGGTTGTATTTCTATATTTATTTTCAGTATACTGTGTGGGATACTTAGTGGTATG
TCTCTTTAAGTTTTGATTAATGTTTCTTAAATGGAATTATTTTGAATGTCACAAATTGA
TCAAGATATTAAAATGTCGGATTTATCTTTCCCCATATCCAAGTACCAATGCTGTTGT
AAACAACGTGTATAGTGCCTAAAATTGTATGAAAATCCTTTTAACCATTTTAACCTAG
ATGTTTAACAAATCTAATCTCTTATTCTAATAAATATACTATGAAATAAAAAAAAAAGG
ATGAAAGCTAAAAAAAAAAAAAAAAAAAA
```

*Figure 8*

Wild-type Human MEK1 Polypeptide Sequence (SEQ ID NO:2) (NP_002746; gi:5579478)

MPKKKPTPIQLNPAPDGSAVNGTSSAETNLEALQKKLEELELDEQQRKRLEAFL
TQKQKVGELKDDDFEKISELGAGNGGVVFKVSHKPSGLVMARKLIHLEIKPAIR
NQIIRELQVLHECNSPYIVGFYGAFYSDGEISICMEHMDGGSLDQVLKKAGRIP
EQILGKVSIAVIKGLTYLREKHKIMHRDVKPSNILVNSRGEIKLCDFGVSGQLIDS
MANSFVGTRSYMSPERLQGTHYSVQSDIWSMGLSLVEMAVGRYPIPPPDAKE
LELMFGCQVEGDAAETPPRPRTPGRPLSSYGMDSRPPMAIFELLDYIVNEPPP
KLPSGVFSLEFQDFVNKCLIKNPAERADLKQLMVHAFIKRSDAEEVDFAGWLC
STIGLNQPSTPTHAAGV

*Figure 9*

Wild-type Human MEK2 Nucleic Acid Sequence (SEQ ID NO:3) (NM_030662; gi:187171274)

CCCCTGCCTCTCGGACTCGGGCTGCGGCGTCAGCCTTCTTCGGGCCTCGGCA
GCGGTAGCGGCTCGCTCGCCTCAGCCCCAGCGCCCTCGGCTACCCTCGGCC
CAGGCCCGCAGCGCCGCCCGCCCTCGGCCGCCCCGACGCCGGCCTGGGCCG
CGGCCGCAGCCCCGGGCTCGCGTAGGCGCCGACCGCTCCCGGCCCGCCCCC
TATGGGCCCCGGCTAGAGGCGCCGCCGCCGCCGGCCCGCGGAGCCCCGATG
CTGGCCCGGAGGAAGCCGGTGCTGCCGGCGCTCACCATCAACCCTACCATCG
CCGAGGGCCCATCCCCTACCAGCGAGGGCGCCTCCGAGGCAAACCTGGTGGA
CCTGCAGAAGAAGCTGGAGGAGCTGGAACTTGACGAGCAGCAGAAGAAGCGG
CTGGAAGCCTTTCTCACCCAGAAAGCCAAGGTCGGCGAACTCAAAGACGATGA
CTTCGAAAGGATCTCAGAGCTGGGCGCGGGCAACGGCGGGGTGGTCACCAAA
GTCCAGCACAGACCCTCGGGCCTCATCATGGCCAGGAAGCTGATCCACCTTGA
GATCAAGCCGGCCATCCGGAACCAGATCATCCGCGAGCTGCAGGTCCTGCAC
GAATGCAACTCGCCGTACATCGTGGGCTTCTACGGGGCCTTCTACAGTGACGG
GGAGATCAGCATTTGCATGGAACACATGGACGGCGGCTCCCTGGACCAGGTG
CTGAAAGAGGCCAAGAGGATTCCCGAGGAGATCCTGGGGAAAGTCAGCATCG
CGGTTCTCCGGGGCTTGGCGTACCTCCGAGAGAAGCACCAGATCATGCACCG
AGATGTGAAGCCCTCCAACATCCTCGTGAACTCTAGAGGGGAGATCAAGCTGT
GTGACTTCGGGGTGAGCGGCCAGCTCATCGACTCCATGGCCAACTCCTTCGTG
GGCACGCGCTCCTACATGGCTCCGGAGCGGTTGCAGGGCACACATTACTCGG
TGCAGTCGGACATCTGGAGCATGGGCCTGTCCCTGGTGGAGCTGGCCGTCGG
AAGGTACCCCATCCCCCCGCCCGACGCCAAAGAGCTGGAGGCCATCTTTGGC
CGGCCCGTGGTCGACGGGGAAGAAGGAGAGCCTCACAGCATCTCGCCTCGGC
CGAGGCCCCCCGGGCGCCCCGTCAGCGGTCACGGGATGGATAGCCGGCCTG
CCATGGCCATCTTTGAACTCCTGGACTATATTGTGAACGAGCCACCTCCTAAGC
TGCCCAACGGTGTGTTCACCCCCGACTTCCAGGAGTTTGTCAATAAATGCCTCA
TCAAGAACCCAGCGGAGCGGGCGGACCTGAAGATGCTCACAAACCACACCTTC
ATCAAGCGGTCCGAGGTGGAAGAAGTGGATTTTGCCGGCTGGTTGTGTAAAAC
CCTGCGGCTGAACCAGCCCGGCACACCCACGCGCACCGCCGTGTGACAGTGG
CCGGGCTCCCTGCGTCCGCTGGTGACCTGCCCACCGTCCCTGTCCATGCCC
CGCCCTTCCAGCTGAGGACAGGCTGGCGCCTCCACCCACCCTCCTGCCTCAC
CCCTGCGGAGAGCACCGTGGCGGGGCGACAGCGCATGCAGGAACGGGGGTC
TCCTCTCCTGCCCGTCCTGGCCGGGGTGCCTCTGGGGACGGGCGACGCTGCT
GTGTGTGGTCTCAGAGGCTCTGCTTCCTTAGGTTACAAAACAAAACAGGGAGA
GAAAAAGCAAAAAAAAAAAAAAAAAAAAAAAAAAAA

*Figure 10*

Wild-type Human MEK2 Polypeptide Sequence (SEQ ID NO:4) (NP_109587; gi:13489054)

MLARRKPVLPALTINPTIAEGPSPTSEGASEANLVDLQKKLEELELDEQQK
KRLEAFLTQKAKVGELKDDDFERISELGAGNGGVVTKVQHRPSGLIMAR
KLIHLEIKPAIRNQIIRELQVLHECNSPYIVGFYGAFYSDGEISICMEHMDG
GSLDQVLKEAKRIPEEILGKVSIAVLRGLAYLREKHQIMHRDVKPSNILVNS
RGEIKLCDFGVSGQLIDSMANSFVGTRSYMAPERLQGTHYSVQSDIWSM
GLSLVELAVGRYPIPPPDAKELEAIFGRPVVDGEEGEPHSISPRPRPPGR
PVSGHGMDSRPAMAIFELLDYIVNEPPPKLPNGVFTPDFQEFVNKCLIKN
PAERADLKMLTNHTFIKRSEVEEVDFAGWLCKTLRLNQPGTPTRTAV

*Figure 11*

```
               10        20         30        40        50
MEK1   MPKKKPT--PIQLNPA-PDGSAVNGTSSAEINLEALQKKLEELELDEQQRKRLEAFLTQK
       . ..:.   . .::.  .: . .. ...:.:: :::::::::::::.:::::::::::
MEK2   LARRKPVLPALTINPTIAEGPSPTSEGASEANLVDLQKKLEELELDEQQKKRLEAFLTQK
              10        20        30        40        50        60

60        70        80        90       100       110
MEK1   QKVGELKDDDFEKISELGAGNGGVVFKVSHKPSGLVMARKLIHLEIKPAIRNQIIRELQV
       :::::::::::.:::::::::::: ::.:.:::.:::::::::::::::::::::::::
MEK2   AKVGELKDDDFERISELGAGNGGVVTKVQHRPSGLIMARKLIHLEIKPAIRNQIIRELQV
              70        80        90       100       110       120

120       130       140       150       160       170
MEK1   LHECNSPYIVGFYGAFYSDGEISICMEHMDGGSLDQVLKKAGRIPEQILGKVSIAVIKGL
       ::::::::::::::::::::::::::::::::::::::::.: ::::.:::::::::..::
MEK2   LHECNSPYIVGFYGAFYSDGEISICMEHMDGGSLDQVLKEAKRIPEEILGKVSIAVLRGL
              130       140       150       160       170       180

180       190       200       210       220       230
MEK1   TYLREKHKIMHRDVKPSNILVNSRGEIKLCDFGVSGQLIDSMANSFVGTRSYMSPERLQG
       .:::::::.:::::::::::::::::::::::::::::::::::::::::::.::::::
MEK2   AYLREKHQIMHRDVKPSNILVNSRGEIKLCDFGVSGQLIDSMANSFVGTRSYMAPERLQG
              190       200       210       220       230       240

240       250       260       270       280       290
MEK1   THYSVQSDIWSMGLSLVEMAVGRYPIPPPDAKELELMFGCQV----EGDAAETPPRPRIP
       :::::::::::::::::::.:::::::::::::::: .:: :    ::.   ::::  :
MEK2   THYSVQSDIWSMGLSLVELAVGRYPIPPPDAKELEAIFGRPVVDGEEGEPHSISPRPRPP
              250       260       270       280       290       300

300       310       320       330       340       350
MEK1   GRPLSSYGMDSRPPMAIFELLDYIVNEPPPKLPSGVFSLEFQDFVNKCLIKNPAERADLK
       :::.:...::::::: :::::::::::::::::::.:::. ..:.:::::::::::::::
MEK2   GRPVSGHGMDSRPAMAIFELLDYIVNEPPPKLPNGVFTPDFQEFVNKCLIKNPAERADLK
              310       320       330       340       350       360

360       370       380       390
MEK1   QLMVHAFIKRSDAEEVDFAGWLCSTIGLNQPSTPTHAA
       .:  :.:::::..:::::::::::.:. ::::.::..:
MEK2   MLTNHTFIKRSEVEEVDFAGWLCKTLRLNQPGTPTRTA
              370       380       390
```

MEK MUTATIONS CONFERRING RESISTANCE TO MEK INHIBITORS

RELATED APPLICATIONS

This application claims priority to U.S. Provisional Patent Application No. 61/121,467, filed on Dec. 10, 2008, and to U.S. Provisional Patent Application No. 61/180,739, filed on May 22, 2009. The entire contents of the foregoing patent applications are incorporated herein by reference.

BACKGROUND OF THE INVENTION

The treatment of cancer is one of the greatest challenges in modern medicine. While chemotherapeutic agents are typically an effective means of treating or reducing the symptoms associated with cancer, in some cases, resistance to one or more chemotherapeutic agents manifests during treatment. As a result, a given chemotherapeutic agent can become ineffective in certain individuals. The molecular mechanisms responsible for the development of resistance in various types of cancer are poorly understood. Elucidation of the mechanisms that underlie resistance to specific agents is essential to discovering treatment approaches that effectively circumvent drug resistance.

SUMMARY OF THE INVENTION

The present invention pertains to mutation-mediated resistance to chemotherapeutic treatment of cancer. In specific embodiments, the present invention is directed to mutations identified in MEK polypeptides, and in nucleic acid molecules encoding the MEK polypeptides. These mutations confer resistance to MEK inhibitors currently in therapeutic use. The identification of these mutations allows for the development of second-generation MEK inhibitors that exhibit activity against a MEK polypeptide containing one or more mutations, such as the mutations described herein. Such second-generation MEK inhibitors are useful in many clinical and therapeutic applications, including the treatment of cancer.

Accordingly, the invention features, in a first aspect, an isolated nucleic acid molecule encoding a mutant MEK polypeptide having a MEK activity, wherein said mutant MEK polypeptide comprises an amino acid sequence having at least one amino acid substitution as compared to a wild type MEK polypeptide selected from the group consisting of MEK1 (SEQ ID NO:2) and MEK2 (SEQ ID NO:4), the at least one amino acid substitution conferring resistance to one or more MEK inhibitors on the mutant MEK protein. In one embodiment, the wild type MEK polypeptide is MEK1 and the at least one substitution occurs at one or more amino acid positions selected from the group consisting of 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H. In another embodiment, the wild type MEK polypeptide is MEK1 and the at least one substitution occurs at one or more amino acid positions selected from the group consisting of 56Q, 99I, 104K, 113R, 120E, 128G, 133F, 215L, 237G, 326P and 368E. In one embodiment, the wild type MEK polypeptide is MEK2 and the at least one substitution occurs at one or more amino acid positions selected from the group consisting of 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another embodiment, the wild type MEK polypeptide is MEK2, and the at least one substitution occurs at one or more amino acid positions selected from the group consisting of 60Q, 103I, 108K, 117R, 124E, 132G, 137F, 219L, 241G, 334P and 376E. In an exemplary embodiment, the wild type MEK polypeptide is MEK1 and the at least one substitution is selected from the group consisting of 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D. In another exemplary embodiment, the wild type MEK polypeptide is MEK1 and the at least one substitution is selected from the group consisting of 56Q>P, 99I>T, 104K>N, 113R>S, 120E>D, 128G>D, 133F>L, 215L>P, 237G>V, 326P>L, 368E>K. In another exemplary embodiment, the wild type MEK polypeptide is MEK2 and the at least one substitution is selected from the group consisting of 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In another exemplary embodiment, the wild type MEK polypeptide is MEK2 and the at least one substitution is selected from the group consisting of 60Q>P, 103I>T, 108K>N, 117R>S, 124E>D, 132G>D, 137F>L, 219L>P, 241G>V, 334P>L, 376E>K.

In one embodiment of the foregoing aspect, the mutant MEK polypeptide has one to five amino acid substitutions as compared to the wild type MEK polypeptide. In another embodiment, the mutant MEK polypeptide has one amino acid substitution as compared to the wild type MEK polypeptide. In an exemplary embodiment, the mutant MEK polypeptide is a MEK1 polypeptide comprising a 111I>N substitution, a 115L>R substitution, a 124P>L substitution and/or a 129F>L substitution. In another exemplary embodiment, mutant MEK polypeptide is a MEK2 polypeptide comprising a 115I>N substitution, a 119L>R substitution, a 128P>L substitution or a 133F>L substitution. In various embodiments of the foregoing aspect, the MEK inhibitor is selected from the group consisting of CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile (referenced herein as "Compound A"), and 4[3-Chloro-4-(1-methyl-1H-imidazol-2-ylsulfanyl)-phenylamino]-6-methoxy-7-(3-morpholin-4-yl-propoxy)-quinoline-3-carbonitrile (referenced herein as "Compound B").

The isolated nucleic acid molecules encoding mutant MEK polypeptides can be inserted into an expression vector and expressed in a host cell. Accordingly, in another aspect, the invention features an expression vector comprising a nucleic acid molecule as set forth herein. In another aspect, the invention features a host cell comprising the foregoing expression vector. In another aspect, the invention features a method of producing a mutant MEK polypeptide, comprising culturing a host cell containing an expression vector encoding a mutant MEK polypeptide, such that a mutant MEK polypeptide is produced by the cell.

In other aspects, the invention features an isolated mutant MEK polypeptide having a MEK activity, wherein said mutant MEK polypeptide comprises an amino acid sequence having at least one amino acid substitution as compared to a wild type MEK polypeptide selected from the group consisting of MEK1 (SEQ ID NO: 2) and MEK2 (SEQ ID NO:4), the at least one amino acid substitution conferring resistance to one or more MEK inhibitors on the mutant MEK polypeptide. In one embodiment of this aspect, the wild type MEK polypeptide is MEK1 and the at least one substitution occurs at one or more amino acid positions selected from the group consisting of 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H. In another embodiment, the wild type MEK polypeptide is MEK1 and the at least one substitution occurs at one or more amino acid positions selected from the group consisting of 56Q, 99I, 104K, 113R, 120E, 128G, 133F, 215L, 237G, 326P and 368E. In one embodiment, the wild type MEK polypeptide is MEK2 and the at least one substitution occurs at one or more amino acid positions selected from the group consisting of 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another embodiment, the wild type MEK polypeptide is MEK2, and the at least one substitution occurs at one or more amino acid positions selected from the group consisting of 60Q, 103I, 108K, 117R, 124E, 132G, 137F, 219L, 241G, 334P and 376E. In an exemplary embodiment, the wild type MEK polypeptide is MEK1 and the at least one substitution is selected from the group consisting of 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D. In another exemplary embodiment, the wild type MEK polypeptide is MEK1 and the at least one substitution is selected from the group consisting of 56Q>P, 99I>T, 104K>N, 113R>S, 120E>D, 128G>D, 133F>L, 215L>P, 237G>V, 326P>L and 368E>K. In another exemplary embodiment, the wild type MEK polypeptide is MEK2 and the at least one substitution is selected from the group consisting of 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In another exemplary embodiment, the wild type MEK polypeptide is MEK2 and the at least one substitution is selected from the group consisting of 60Q>P, 103I>T, 108K>N, 117R>S, 124E>D, 132G>D, 137F>L, 219L>P, 241G>V, 334P>L and 376E>K.

In one embodiment of the foregoing aspect, the mutant MEK polypeptide has one to five amino acid substitutions as compared to the wild type MEK polypeptide. In another embodiment, the mutant MEK polypeptide has one amino acid substitution as compared to the wild type MEK polypeptide. In an exemplary embodiment, the mutant MEK polypeptide is a MEK1 polypeptide that comprises a 111I>N substitution, a 115L>R substitution, a 124P>L substitution and/or a 129F>L substitution. In another exemplary embodiment, mutant MEK polypeptide is a MEK2 polypeptide that comprises a 115I>N substitution, a 119L>R substitution, a 128P>L substitution or a 133F>L substitution. In various embodiments of the foregoing aspect, the MEK inhibitor is selected from the group consisting of CI-1040, AZD6244, PD318088, PD98059, PD334581, RDEA119, Compound A, and Compound B.

In another aspect, the invention features a method of identifying a compound that is useful in treating cancer, comprising: providing an assay composition comprising a mutant MEK polypeptide and a MEK substrate; contacting the assay composition with a test compound under conditions that permit phosphorylation of the MEK substrate in the absence of the test compound; and determining the effect of the compound on phosphorylation of the MEK substrate; wherein downmodulation of phosphorylation of the MEK substrate as compared to a suitable control identifies the compound as a compound that is useful in treating cancer.

In a related aspect, the invention features a method of identifying a compound as a second generation MEK inhibitor, comprising: providing an assay composition comprising a mutant MEK polypeptide and a MEK substrate; contacting the assay composition with a test compound under conditions that permit phosphorylation of the MEK substrate in the absence of the test compound; and determining the effect of the compound on phosphorylation of the MEK substrate; wherein downmodulation of phosphorylation of the MEK substrate as compared to a suitable control identifies the compound as a second generation MEK inhibitor.

In exemplary embodiments of the foregoing aspects, the MEK substrate is ERK1/2. In other embodiments, the assay composition is a cell extract.

In another aspect, the invention features a method of identifying a compound that is useful in treating cancer, comprising: providing a cell comprising a mutant MEK polypeptide; contacting the cell with a test compound; and determining the effect of the compound on ERK1/2 phosphorylation; wherein downmodulation of ERK1/2 phosphorylation as compared to an appropriate control identifies the compound as a compound that is useful in treating cancer. In a related aspect, the invention provides a method of identifying a compound that is a second generation MEK inhibitor, comprising: providing a cell comprising a mutant MEK polypeptide; contacting the cell with a test compound; and determining the effect of the compound on ERK1/2 phosphorylation; wherein downmodulation of ERK1/2 phosphorylation as compared to an appropriate control identifies the compound as a second generation MEK inhibitor.

In another aspect, the invention features a method of identifying a compound that is useful in treating cancer, comprising: providing a cell comprising a mutant MEK polypeptide; contacting the cell with a test compound; and determining the effect of the compound on cell proliferation; wherein reduction in cell proliferation as compared to an appropriate control identifies the compound as a compound that is useful in treating cancer. In a related aspect, the invention provides a method of identifying a compound that is a second generation MEK inhibitor, comprising: providing a cell comprising a mutant MEK polypeptide; contacting the cell with a test compound; and determining the effect of the compound on cell proliferation; wherein reduction in cell proliferation as compared to an appropriate control identifies the compound as a second generation MEK inhibitor.

In another aspect, the invention features a cell-based screening method for identifying a test compound as a second generation MEK inhibitor, the method comprising contacting the host cell comprising a mutant MEK polypeptide with a test compound, wherein sensitivity of the host cell to the test compound identifies the compound as a second-generation MEK inhibitor. In one embodiment of this aspect, sensitivity of the host cell to the test compound is measured using an assay selected from the group consisting of a cell proliferation assay, a cell viability assay, and a ERK1/2 phosphorylation assay, wherein a reduction in cell proliferation, cell viability, or ERK1/2 phosphorylation in the presence of the test compound identifies the compound as a second-generation MEK inhibitor.

In another aspect, the invention features a method of identifying a second-generation MEK inhibitor, comprising: selecting a potential drug using computer-assisted modeling with a three-dimensional crystal or solution structure of a mutant MEK polypeptide, wherein said mutant MEK polypeptide comprises an amino acid sequence having at least one amino acid substitution as compared to a wild type MEK polypeptide selected from the group consisting of MEK1 (SEQ ID NO: 2) and MEK2 (SEQ ID NO:4), the at least one amino acid substitution conferring resistance to one or more MEK inhibitors on the mutant MEK polypeptide; contacting said potential drug with the mutant MEK polypeptide; and detecting the interaction of said potential drug with the mutant MEK polypeptide; wherein a compound that is capable of interacting with the mutant MEK polypeptide is identified as a second-generation MEK inhibitor.

In one embodiment of the foregoing aspects, the test compound is a member of a library of compounds.

In another aspect, the invention features a compound identified by one of the foregoing methods. Such compounds are useful, for example, in inhibiting the activity of a mutant MEK polypeptide. Accordingly, in another aspect, the invention features a method of inhibiting the activity of a mutant MEK polypeptide, comprising contacting the mutant MEK polypeptide with a compound identified according to one of the foregoing methods. In an exemplary embodiment, the compound inhibits the activity of a mutant MEK polypeptide and a wild-type MEK polypeptide. In one embodiment, said contacting occurs in vitro. In another embodiment, said contacting occurs in vivo. In another embodiment, said contacting occurs in a subject. In an exemplary embodiment, said contacting occurs in a subject having a cancer. In one embodiment, the subject having a cancer has relapsed from treatment with a first generation MEK inhibitor selected from the group consisting of CI-1040, AZD6244, PD318088, PD98059, PD334581, RDEA119, Compound A, and Compound B. In an exemplary embodiment, the cancer is a melanoma.

In another aspect, the invention features a method of treating a subject having a cancer, comprising administering to the subject a compound identified according to one of the foregoing methods. In an exemplary embodiment, the compound inhibits the activity of a mutant MEK polypeptide and a wild-type MEK polypeptide. In one embodiment, the subject has relapsed from treatment with a first generation MEK inhibitor selected from the group consisting of CI-1040, AZD6244, PD318088, PD98059, PD334581, RDEA119, Compound A, and Compound B. In a particular embodiment, the cancer comprises a MEK polypeptide having one or more mutations with respect to a wild type MEK polypeptide, and/or a MEK nucleic acid molecule encoding a MEK polypeptide having one or more mutations with respect to a wild type MEK polypeptide, wherein the one or more mutations confer resistance to one or more MEK inhibitors on the mutant MEK polypeptide. In an exemplary embodiment, the cancer is a melanoma.

In another aspect, the invention features a method of screening a subject having cancer, the method comprising obtaining a cancer cell-containing sample from the subject; and determining the presence or absence of one or more amino acid substitutions in a wild type MEK polypeptide selected from the group consisting of MEK1 (SEQ ID NO: 2) and MEK2 (SEQ ID NO:4) in the cancer cell-containing sample. In one embodiment of this aspect, the wild type MEK polypeptide is MEK1 and the one or more amino acid substitutions occur at one or more residues selected from the group consisting of 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H. In another embodiment, the wild type MEK polypeptide is MEK1 and the one or more amino acid substitutions occur at one or more residues selected from the group consisting of 56Q, 99I, 104K, 113R, 120E, 128G, 133F, 215L, 237G, 326P and 368E. In one embodiment, the wild type MEK polypeptide is MEK2 and the one or more amino acid substitutions occur at one or more residues selected from the group consisting of 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another embodiment, the wild type MEK polypeptide is MEK2 and the one or more amino acid substitutions occur at one or more residues selected from the group consisting of 60Q, 103I, 108K, 117R, 124E, 132G, 137F, 219L, 241G, 334P and 376E.

In one embodiment of the foregoing aspect, detection of one or more mutations in the MEK1 or MEK2 polypeptides identifies the subject as having a relatively high risk of relapse during treatment with a first generation MEK inhibitor. In another embodiment, detection of one or more mutations in the MEK1 or MEK2 polypeptides identifies the subject as being unresponsive to treatment with a first generation MEK inhibitor. In exemplary embodiments, the first generation MEK inhibitor is selected from the group consisting of CI-1040, AZD6244, PD318088, PD98059, PD334581, RDEA119, Compound A, and Compound B. In another embodiment of the foregoing aspect, the presence of one or more mutations in the MEK1 or MEK2 polypeptides stratifies the subject to treatment with a second generation MEK inhibitor. In another embodiment, the presence of one or more mutations in the MEK polypeptide stratifies the subject to treatment with a combination therapy that includes administration of both a MEK inhibitor (e.g., a first generation MEK inhibitor or a second generation MEK inhibitor) and a RAF inhibitor.

In another aspect, the invention provides a method of identifying a subject having cancer who is likely to benefit from treatment with a MEK inhibitor and a RAF inhibitor, comprising (a) assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2 and/or assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4; and (b) correlating the presence of the one or more mutations in a nucleic acid molecule encoding a MEK polypeptide with a subject who is likely to benefit from treatment with a MEK inhibitor and a RAF inhibitor.

In another aspect, the invention provides a method of optimizing treatment of a subject having cancer, comprising: (a) extracting nucleic acid from cells of the cancer; and (b) sequencing a nucleic acid molecule encoding a MEK polypeptide; wherein the presence of nucleotides that alter the identity of an amino acid residue at one or more amino acids of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or the presence of nucleotides that alter the identity of an amino acid residue at one or more amino acids of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4, indicates a need to treat the subject with a MEK inhibitor and a RAF inhibitor.

In another aspect, the invention provides a method of optimizing treatment of a subject having cancer, comprising: (a) extracting nucleic acid from cells of the cancer; and (b) subjecting the sample to PCR and identifying the nucleotide sequence of a nucleic acid molecule encoding a MEK polypeptide; wherein the presence of nucleotides that alter the identity of an amino acid residue at one or more amino acid of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or the presence of nucleotides that alter the identity of an amino acid residue at one or more amino acid of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4, indicates a need to treat the subject with a MEK inhibitor and a RAF inhibitor.

In another aspect, the invention provides a method of treating a subject having cancer, comprising: (a) extracting nucleic acid from cells of the cancer; (b) sequencing a nucleic acid molecule encoding a MEK polypeptide; and (c) administering a MEK inhibitor and a RAF inhibitor to the subject when the nucleic acid molecule contains nucleotides that alter the identity of an amino acid residue at one or more amino acid of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or when the nucleic acid molecule contains nucleotides that alter the identity of an amino acid residue at one or more amino acid of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4.

In another aspect, the invention provides a method of treating a subject having cancer, comprising: (a) extracting nucleic acid from cells of the cancer; (b) subjecting the sample to PCR and identifying the nucleotide sequence of a nucleic acid molecule encoding a MEK polypeptide; and (c) administering a MEK inhibitor and a RAF inhibitor to the subject when the nucleic acid molecule contains nucleotides that alter the identity of an amino acid residue at one or more amino acids of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or when the nucleic acid molecule contains nucleotides that alter the identity of an amino acid residue at one or more amino acid of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4.

In exemplary embodiments of the foregoing aspects, the RAF inhibitor is PLX4720, PLX4032, BAY 43-9006 (Sorafenib), ZM 336372, RAF 265, AAL-881, LBT-613, or CJS352.

In another aspect, the invention provides a method of identifying a subject having cancer as having a high risk of relapse during treatment with a first-generation MEK inhibitor, comprising: (a) extracting nucleic acid from cells of the cancer; and (b) sequencing a nucleic acid molecule encoding a MEK polypeptide; wherein the presence of nucleotides that alter the identity of an amino acid residue at one or more amino acids of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or the presence of nucleotides that alter the identity of an amino acid residue at one or more amino acids of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4, identifies the subject as having a high risk of relapse during treatment with a first-generation MEK inhibitor.

In another aspect, the invention provides a method of identifying a subject having cancer as having a high risk of relapse during treatment with a first generation MEK inhibitor, comprising: (a) assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2 and/or assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4; and (b) correlating the presence of the one or more mutations in a nucleic acid molecule encoding a MEK polypeptide with a subject having a high risk of relapse during treatment with a first generation MEK inhibitor.

In another aspect, the invention provides a method of identifying a subject having cancer as being unresponsive to treatment with a first-generation MEK inhibitor, comprising: (a) extracting nucleic acid from cells of the cancer; and (b) sequencing a nucleic acid molecule encoding a MEK polypeptide; wherein the presence of nucleotides that alter the identity of an amino acid residue at one or more amino acids of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or the presence of nucleotides that alter the identity of an amino acid residue at one or more amino acids of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4, identifies the subject as being unresponsive to treatment with a first-generation MEK inhibitor.

In another aspect, the invention provides a method of identifying a subject having cancer as being unresponsive to treatment with a first-generation MEK inhibitor, comprising: (a) assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2 and/or assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4; and (b) correlating the presence of the one or more mutations in a nucleic acid molecule encoding a MEK polypeptide with a subject who is unresponsive to treatment with a first-generation MEK inhibitor.

In exemplary embodiments of the foregoing aspects, the MEK inhibitor is CI-1040, AZD6244, PD318088, PD98059, PD334581, RDEA119, Compound A, or Compound B.

In another aspect, the invention provides a method of identifying a subject having cancer who is likely to benefit from treatment with a second-generation MEK inhibitor, comprising: (a) extracting nucleic acid from cells of the cancer; and (b) sequencing a nucleic acid molecule encoding a MEK polypeptide; wherein the presence of nucleotides that alter the identity of an amino acid residue at one or more amino acids of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2, or the presence of nucleotides that alter the identity of an amino acid residue at one or more amino acids of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4, identifies the subject as being likely to benefit from treatment with a second-generation MEK inhibitor.

In another aspect, the invention provides a method of identifying a subject having cancer who is likely to benefit from treatment with a second-generation MEK inhibitor, comprising: (a) assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 56Q, 67D, 74L, 99I, 103I, 104K, 106A, 107I, 111I, 113R, 115L, 119H, 120E, 124P, 128G, 129F, 133F, 167G, 203E, 211V, 215L, 237G, 247W, 258V, 260R, 276G, 286G, 302M, 303D, 308M, 326P, 328G, 368E and 399H of SEQ ID NO:2 and/or assaying a nucleic acid sample obtained from the cancer for the presence of one or more mutations in a nucleic acid molecule encoding a MEK polypeptide that alter the identity of one or more amino acid residues of the encoded MEK polypeptide relative to the amino acid at one or more positions selected from the group consisting of 60Q, 71D, 78L, 103I, 107I, 108K, 110A, 111I, 115I, 117R, 119L, 123H, 124E, 128P, 132G, 133F, 137F, 171G, 207E, 215V, 219L, 241G, 251W, 262V, 264R, 280G, 310M, 311D, 316M, 334P, 336G, and 376E of SEQ ID NO:4; and (b) correlating the presence of the one or more mutations in a nucleic acid molecule encoding a MEK polypeptide with a subject who is likely to benefit from treatment with a second-generation MEK inhibitor.

In one embodiment of the foregoing aspects, the second generation MEK inhibitor is the Roche compound RG7420.

In some embodiments of the foregoing aspects, the cancer is a leukemia, a lymphoma, a myeloma, a carcinoma, a metastatic carcinoma, a sarcoma, an adenoma, a nervous system cancer or a geritourinary cancer. In an exemplary embodiment, the cancer is a melanoma.

In one aspect, the invention provides kits for optimizing treatment of a subject having cancer, identifying a subject having cancer who is likely to benefit from treatment with a MEK inhibitor and a RAF inhibitor, identifying a subject having cancer who has a high risk of relapse during treatment with a first-generation MEK inhibitor, identifying a subject having cancer who is unresponsive to treatment with a first-generation MEK inhibitor, and/or for identifying a subject having cancer who is likely to benefit from treatment with a second-generation MEK inhibitor, comprising: (a) a detection reagent useful for identifying the presence or absence of one or more mutations in a MEK polypeptide of SEQ ID NO:1 or SEQ ID NO:2; and (b) instructions describing a method set forth herein. In an exemplary embodiment, the detection reagent comprises nucleic acid primers useful for amplification of a MEK polypeptide.

In various embodiments of the foregoing aspects, the presence of one or more mutations in a MEK polypeptide, e.g., a MEK polypeptide in a cancer cell-containing sample, is determined by a method comprising determining the sequence of a nucleic acid molecule encoding the MEK polypeptide. In other embodiments, the presence of one or more mutations in a MEK polypeptide is determined using an antibody that recognizes a MEK polypeptide comprising the one or more mutations. In another embodiment, the foregoing methods further comprise administering a compound of identified according to a method described herein to a subject in whom the presence of one or more mutations in a MEK polypeptide was detected.

In another aspect, the invention features a method of inhibiting a MEK polypeptide in a subject, comprising administering a compound identified by one of the foregoing methods to a subject in whom the presence of one or more mutations in a MEK polypeptide was detected.

BRIEF DESCRIPTION OF THE DRAWINGS

FIG. 8 depicts the wild-type human MEK1 nucleic acid sequence (SEQ ID NO:1) (Accession No. NM_002755; gi:169790828).

FIG. 9 depicts the wild-type human MEK1 polypeptide sequence (SEQ ID NO:2) (Accession No. NP_002746; gi:5579478).

FIG. 10 depicts the wild-type human MEK2 nucleic acid sequence (SEQ ID NO:3) (Accession No. NM_030662; gi:187171274).

FIG. 11 depicts the wild-type human MEK2 polypeptide sequence (SEQ ID NO:4) (Accession No. NP_109587; gi:13489054).

FIG. 12 depicts a sequence alignment between wild-type human MEK1 (SEQ ID NO:2) and wild-type human MEK2 (SEQ ID NO:4).

DETAILED DESCRIPTION OF THE INVENTION

Figure 1:
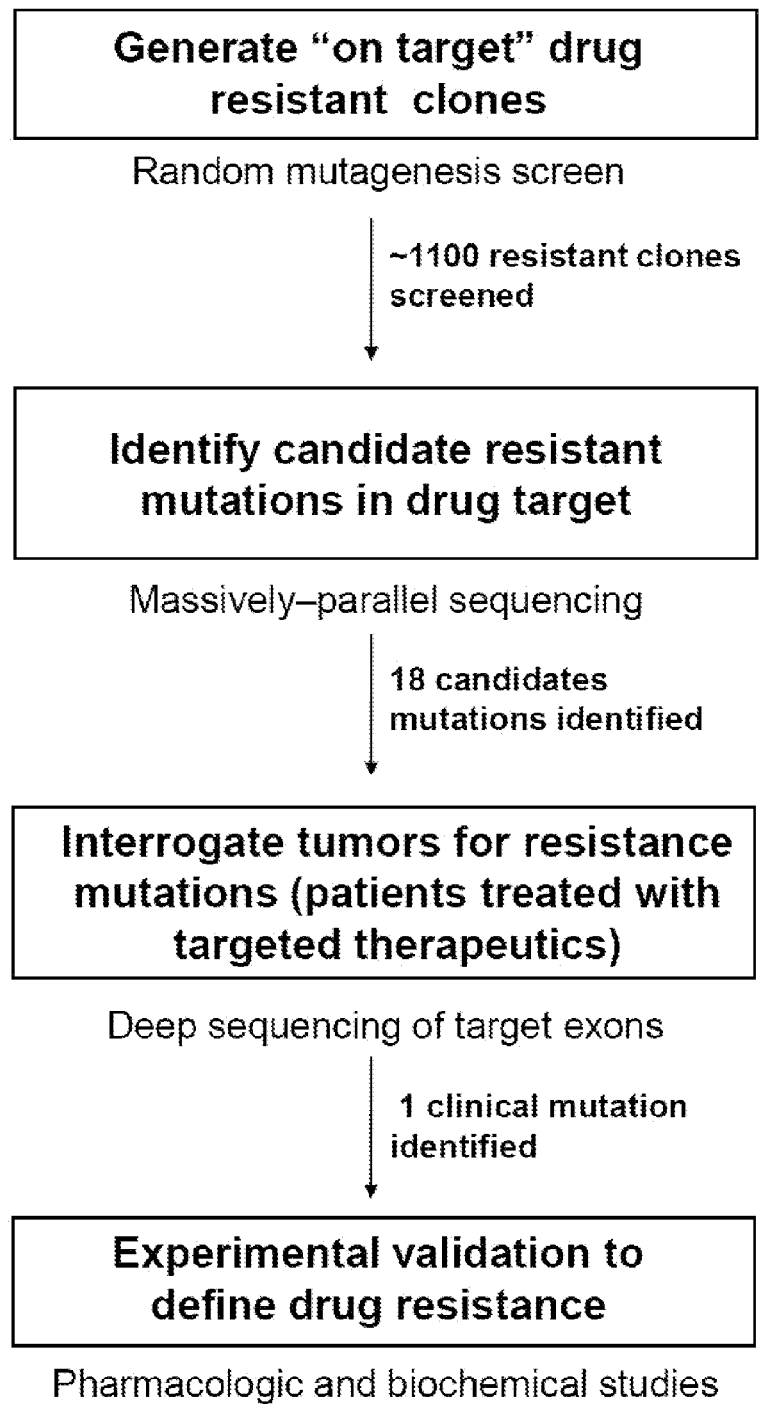
FIG. 1 presents a schematic diagram depicting the design of a study to identify "on-target" resistance mutations in vitro and in vivo. A random mutagenesis screen was performed using a class of first-generation MEK inhibitors in clinical development. High-frequency mutations in MEK1 were identified, and the corresponding exons were probed by deep sequencing of patient samples. The resistance phenotype of representative MEK1 alleles was confirmed by experimental studies.

The present invention relates to the development of resistance to chemotherapeutic therapy for cancer, particularly in cancers having aberrant activation of MAP kinase signaling pathways. Aberrant activation of MAP kinase signaling can result from mutation or overexpression of one or more MAP kinase signaling components. Mutation or overexpression of a component of a MAP kinase signaling pathway may allow a cancer cell to become resistant to one or more chemotherapeutic agents. In particular embodiments, the present invention pertains to development of resistance to a drug that targets a MEK polypeptide. The MEK polypeptide is a key component of MAP kinase signaling pathways. In specific embodiments, the invention concerns mutations in a MEK polypeptide that confer resistance to a drug that targets the MEK polypeptide, but that do not destroy the endogenous enzymatic activity of the MEK polypeptide. In an exemplary embodiment, the mutations in the MEK polypeptide confer resistance to the MEK inhibitors CI-1040, AZD6244, PD318088, PD98059, PD334581, RDEA119, Compound A, and Compound B. Accordingly, a "resistance mutation," as used herein, is a mutation in a MEK polypeptide which confers resistance to one or more MEK inhibitors, e.g., CI-1040, AZD6244, PD318088, PD98059, PD334581, RDEA119, Compound A, and Compound B. Compounds A and B (6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile, respectively) are further described in Zhang et al., Bioorganic & Medicinal Chemistry Letters, 11(11):1407-1410 (2001) and Mallon et al., Mol Cancer Ther. June; 3(6): 755-62 (2004), the entire contents of which are incorporated herein by reference.

The identification of mutations in the MEK polypeptide that confer resistance to a drug that targets the MEK polypeptide allows the development of "second-generation MEK inhibitors." As used herein, the term "second-generation MEK inhibitor" refers to an agent that inhibits a biological activity of a MEK polypeptide containing one or more resistance mutations, such as the mutations described herein. In a preferred embodiment, a second-generation MEK inhibitor also inhibits a biological activity of a wild-type MEK polypeptide. Accordingly, a second generation MEK inhibitor of the invention can inhibit a biological activity of a MEK polypeptide containing one or more resistance mutations and can inhibit a biological activity of a wild-type MEK polypeptide. Such second-generation MEK inhibitors are useful in many clinical and therapeutic applications, for example, in the treatment of cancer. In contrast, the term "first-generation MEK inhibitor," as used herein, refers to an agent that inhibits a biological activity of a wild-type MEK polypeptide, but does not inhibit a biological activity of a MEK polypeptide containing one or more resistance mutations, such as the mutations described herein. Exemplary first-generation MEK inhibitors include CI-1040, AZD6244, PD318088, PD98059, PD334581, RDEA119, Compound A, and Compound B. In one embodiment, a first-generation MEK inhibitor binds to a MEK polypeptide at or near the ATP binding site of the MEK polypeptide. An exemplary second-generation MEK inhibitor is the Roche compound RG7420.

Additional MEK inhibitors include the compounds described in the following patent publications, the entire contents of which are incorporated herein by reference: WO 2008076415, US 20080166359, WO 2008067481, WO 2008055236, US 20080188453, US 20080058340, WO 2007014011, WO 2008024724, US 20080081821, WO 2008024725, US 20080085886, WO 2008021389, WO 2007123939, US 20070287709, WO 2007123936, US 20070287737, US 20070244164, WO 2007121481, US 20070238710, WO 2007121269, WO 2007096259, US 20070197617, WO 2007071951, EP 1966155, IN 2008MN01163, WO 2007044084, AU 2006299902, CA 2608201, EP 1922307, EP 1967516, MX 200714540, IN 2007DN09015, NO 2007006412, KR 2008019236, WO 2007044515, AU 2006302415, CA 2622755, EP 1934174, IN 2008DNO2771, KR 2008050601, WO 2007025090, US 20070049591, WO 2007014011, AU 2006272837, CA 2618218, EP 1912636, US 20080058340, MX 200802114, KR 2008068637, US 20060194802, WO 2006133417, WO 2006058752, AU 2005311451, CA 2586796, EP 1828184, JP 2008521858, US 20070299103, NO 2007003393, WO 2006056427, AU 2005308956, CA 2587178, EP 1838675, JP 2008520615, NO 2007003259, US 20070293544, WO 2006045514, AU 2005298932, CA 2582247, EP 1802579, CN 101065358, JP 2008517024, IN 2007DNO2762, MX 200704781, KR 2007067727, NO 2007002595, JP 2006083133, WO 2006029862, US 20060063814, U.S. Pat. No. 7,371,869, AU 2005284293, CA 2579130, EP 1791837, CN 101023079, JP 2008513397, BR 2005015371, KR 2007043895, MX 200703166, IN 2007CN01145, WO 2006024034, AU 2005276974, CA 2578283, US 20060079526, EP 1799656, CN 101044125, JP 2008510839, MX 200702208, IN 2007DNO2041, WO 2006018188, AU 2005274390, CA 2576599, EP 1781649, CN 101006085, JP 2008509950, BR 2005014515, AT 404556, US 20060041146, MX 200701846, IN 2007CN00695, KR 2007034635, WO 2006011466, AU 2005265769, CA 2575232, EP 1780197, BR 2005013750, JP 4090070, MX 200700736, CN 101124199, KR 2007041752, IN 2007DN01319, WO 2005121142, AU 2005252110, CA 2569850, US 20060014768, U.S. Pat. No. 7,378,423, EP 1761528, CN 101006086, AT 383360, BR 2005011967, JP 2008501631, EP 1894932, ES 2297723, MX 2006PA14478, NO 2007000155, IN 2007CN00102, KR 2007034581, HK 1107084, JP 2008201788, US 20050256123, US 20050250782, US 20070112038, US 20050187247, WO 2005082891, WO 2005051302, AU 2004293019, CA 2546353, US 20050130943, US 20050130976, US 20050153942, EP 1689233, JP 2007511615, WO 2005051301 AU 2004293018, CA 2545660, US 20050130943, US 20050130976, US 20050153942, EP 1682138, BR 2004016692, CN 1905873, JP 2007511614, MX 2006PA05657, IN 2006DNO3183, NO 2006002692, KR 2007026343, WO 2005028426, EP 1674452, US 20070105859, US 20050054701, U.S. Pat. No. 7,230,099, US 20050049419, U.S. Pat. No. 7,144,907, AU 2004270699, CA 2537321, WO 2005023759, EP 1673339, BR 2004014111, CN 1874769, JP 2007504241, JP 4131741, US 20060030610, MX 2006PA02466, NO 2006001506, US 20050049419, U.S. Pat. No. 7,144,907, US 20050054701, U.S. Pat. No. 7,230,099, AU 2004270699, CA 2537321, WO 2005023759, EP 1673339, BR 2004014111, CN 1874769, JP 2007504241, JP 4131741 US 20060030610, MX 2006PA02466, IN 2006DN01661, NO 2006001506, US 20060189808, US 20060189649, U.S. Pat. No. 7,271,178, US 20060189668, US 20050049276, WO 2005009975, CA 2532067, EP 1651214, BR 2004012851, JP 2006528621, US 20050026970, U.S. Pat. No. 7,160,915, MX 2006PA00921, WO 2005007616, US 20050059710, WO 2005000818, US 20050026964, U.S. Pat. No. 7,273,877, WO 2004056789, US 20050004186, CA 2509405, AU 2003286306, EP 1578736, BR 2003017254, JP 2006516967, MX 2005PA06803, WO 2004044219, AU 2003291268, WO 2004041811, AU 2003278369, EP 1575943, JP 2006508944, US 20050282856, U.S. Pat. No. 7,173,136, US 20070191346, WO 2004041185, AU 2003287366, US 20060270643, WO 2004030620, AU 2003275282, US 20040092514, U.S. Pat. No. 7,232,826, EP 1545529, US 20040039037, U.S. Pat. No. 6,989,451, WO 2003077855, CA 2478534, AU 2003220202, US 20030216460, EP 1482944, CN 1652792, JP 2005526076, RU 2300528, BR 2003006016, MX 2004PA08894, US 20060106225, WO 2003062191, CA 2473545, EP 1467968, BR 2003007060, JP 2005515253, TW 592692, US 20040006245, U.S. Pat. No. 6,891,066, MX 2004PA05527, US 20050137263, U.S. Pat. No. 7,078,438, WO 2003062189, CA 2472367, EP 1467965, BR 2003007071, JP 2005515251, US 20030232889, U.S. Pat. No. 6,770,778, MX 2004PA05528, WO 2003047585, AU 2002347360, WO 2003047583, AU 2002365665, WO 2003047523, CA 2466762, AU 2002365899, US 20030125359, U.S. Pat. No. 7,307,071, JP 2005526008, EP 1578346, WO 2003035626, CA 2463101, AU 2002359291, EP 1438295, JP 2005508972, US 20050054706, U.S. Pat. No. 7,253,199, US 20070293555, AU 2008202731, U.S. Pat. No. 6,506,798, WO 9901421, WO 2000041994, U.S. Pat. No. 6,310,060, WO 2002006213, CA 2416685, AU 2001073498, BR 2001012584, HU 2003002781, JP 2004504294, JP 3811775, EE 200300030, NZ 524120, AU 2001273498, IN 2003MN00028, NO 2003000249, KR 773621, MX 2003PA00591, HR 2003000083, BG 107564, ZA 2003000348, US 20040054172, U.S. Pat. No. 6,960,614, HK 1055943, US 20050176820, U.S. Pat. No. 7,411,001, WO 2000042029, JP 2000204077, CA 2355374, EP 1144394, BR 9916896, TR 200102029, HU 2001005092, JP 2002534515, EE 200100374, NZ 513432, AT 302761, ES 2249060, ZA 2001005219, MX 2001PA06659, IN 2001MN00785, NO 2001003451, HR 2001000525, BG 105801, U.S. Pat. No. 6,545,030, HK 1042488, US 20030004193, WO 2000042022, JP 2000204079, CA 2355470, EP 1144385, BR 9916904, TR 200102030, HU 2001005113, EE 200100373, JP 2002534510, NZ 513433, AT 302193, ES 2247859, MX 2001PA06568, ZA 2001005224, IN 2001MN00786, U.S. Pat. No. 6,469,004, NO 2001003452, HR 2001000524, BG 105800, WO 2000042003, JP 2000212157, CA 2349832, EP 1144371, BR 9916885, AT 309205, ES 2252996, MX 2001PA04332, U.S. Pat. No. 6,440,966, US 20030092748, U.S. Pat. No. 6,750,217, WO 2000042002, JP 2000204075, CA 2349467, EP 1144372, BR 9916894, JP 2002534497, AT 311363, ES 2251851, MX 2001PA04331, U.S. Pat. No. 6,455,582, US 20030045521, U.S. Pat. No. 6,835,749, WO 2000037141, CA 2352326, BR 9916839, EP 1140291, TR 200101871, HU 2001004844, JP 2002532570, EE 200100339, NZ 512859, AT 310567, ES 2253928, ZA 2001004277, MX 2001PA05476, IN 2001MN00673, NO 2001003099, HR 2001000473, BG 105715, US 20040171632, GB 2323845, WO 9901426, CA 2290506, AU 9882627, AU 757046, EP 993439, BR 9810366, NZ 501276, HU 2000003731, JP 2002511092, AT 277895, IL 132840, PT 993439, ES 2229515, TW 396149, ZA 9805728, MX 9910649, NO 9906491, NO 315271, US 20030078428, U.S. Pat. No. 6,821,963, US 20050049429, US 20060052608, U.S. Pat. No. 7,169,816, WO 9901421, CA 2290509, AU 9882626, AU 756586, EP 993437, BR 9810385, JP 2002509536, NZ 501277, AT 344791, ES 2274572, TW 221831, ZA 9805726, MX 9910576, U.S. Pat. No. 6,310,060, U.S. Pat. No. 6,506,798, US 20020022647, U.S. Pat. No. 6,492,363, US 20030019015, and U.S. Pat. No. 7,019,033. Compounds described in the foregoing publications can be tested using the methods described herein to determine if they are "first-generation MEK inhibitors" or "second-generation MEK inhibitors."

Identification of resistance mutations in the MEK polypeptide also allows for the screening of patients having a cancer in order to determine the presence or absence of one or more MEK resistance mutations in the cancer. Determining the presence or absence of one or more MEK resistance mutations in a cancer allows for alteration of the treatment strategy of a cancer patient. Such alterations can include, for example, starting or stopping treatment with a first generation MEK inhibitor, or starting or stopping treatment with a second generation MEK inhibitor.

The present invention further describes methods of suppressing the emergence of MEK resistance mutations in a subject having cancer. Such methods involve the combined administration of a MEK inhibitor (e.g., a first generation MEK inhibitor or a second generation MEK inhibitor) and a RAF inhibitor. Accordingly, the present invention provides a combination therapy for treating or preventing the symptoms of a cancer, comprising administration of a MEK inhibitor and a RAF inhibitor. The MEK inhibitor may be administered concomitant with, prior to, or following the administration of a RAF inhibitor. As set forth herein, a combination therapy involving a MEK inhibitor and a RAF inhibitor suppresses the emergence of MEK resistance mutations to a greater extent than administration of either a MEK inhibitor or a RAF inhibitor alone.

Various aspects of the invention are described in further detail in the following subsections. Unless otherwise defined, all technical and scientific terms used herein have the same meaning as is commonly understood by one of ordinary skill in the art to which this invention belongs. In case of conflict, the present specification, including definitions, will control. Although methods and materials similar or equivalent to those described herein can be used in the practice of the invention, examples of suitable methods and materials are described below. The materials, methods, and examples described herein are illustrative only and are not intended to be limiting. All publications, patent applications, patents, and other references mentioned herein are incorporated by reference in their entirety.

I. MEK Biological Activity

As used herein, the terms "MEK protein" and "MEK polypeptide" are intended to encompass MEK isoforms, such as MEK1 and MEK2. MEK1 and MEK2 (also known as MKK1 (MAP kinase kinase 1) and MKK2 (MAP kinase kinase 2)) are dual-specific tyrosine and serine/theronine kinases that play a key role in mitogen-activated protein kinase (MAPK) intracellular signaling. Both MEK isoforms are approximately 45 kDa in size, and are expressed ubiquitously in mammalian cells. MEK1 and MEK2 are highly homologous, with MEK2 being 80% identical and 90% similar to MEK1. MEK1 and MEK2 each contain an activation loop that includes two serine residues at positions 217 and 221. Phosphorylation of these residues by the protein kinase Raf results in MEK activation during MAPK signaling. MEK also contains two regulatory phosphorylation sites outside the activation loop. Phosphorylation at Serine 298 may help prime MEK1 for activation. Conversely, phosphorylation at Serine 212 may decrease MEK1 activity.

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors including SOS-1 and CDC25 to the cell membrane. These guanine nucleotide exchange factors interact with and activate the GTPase Ras. Common Ras isoforms include K-Ras, N-Ras, H-Ras and others. Following Ras activation, the serine/threonine kinase Raf (e.g., A-Raf, B-Raf or Raf-1) is recruited to the cell membrane through interaction with Ras. Raf is then phosphorylated. Raf directly activates MEK1 and MEK2 by phosphorylation of two serine residues at positions 217 and 221. Following activation, MEK1 and MEK2 phosphorylate tyrosine (Tyr-185) and threonine (Thr-183) residues in serine/threonine kinases Erk1 and Erk2, resulting in Erk activation. Activated Erk regulates many targets in the cytosol and also translocates to the nucleus, where it phosphorylates a number of transcription factors regulating gene expression. Erk kinase has numerous targets, including Elk-1, c-Ets1, c-Ets2, p90RSK1, MNK1, MNK2, MSK1, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating Raf mutations have been identified in melanoma and ovarian cancer. The most common mutation, BRAF 600V>E, results in constitutive activation of the downstream MAP kinase pathway and is required for melanoma cell proliferation, soft agar growth, and tumor xenograft formation. Based on the defined role of MAPK over-activation in human cancers, targeting components of the MAPK pathway with specific inhibitors is a promising approach to cancer therapy. MEK1 and MEK2 are attractive targets for therapy because of the high degree of specificity they display for their Erk1/2 substrates. The high degree of homology between MEK1 and MEK2 make it likely that a small-molecule MEK inhibitor would effectively inhibit both proteins. CI-1040 (also known as PD184352) is a MEK inhibitor that has been tested in Phase I and Phase II clinical trials. CI-1040 was found to inhibit MEK1 with an in vitro $IC_{50}$ of 17 nmol/L (Friday et al. Clin. Cancer Res. (2008) 14(2):342-346; incorporated herein by reference in its entirety). CI-1040 additionally inhibited MEK in cell-based assays, and reduced human colon cancer xenograft growth, indicating that MEK inhibition is a viable method of cancer therapy.

As used interchangeably herein, the terms "MEK activity," "MEK biological activity" or "functional activity of MEK," include activities exerted by a MEK protein, e.g., MEK1 or MEK2, on a MEK responsive cell or tissue, e.g., a cancer cell, or on a MEK nucleic acid molecule or protein target molecule, as determined in vivo or in vitro, according to standard techniques. MEK activity can be a direct activity, such as an association with a MEK-target molecule e.g., ERK1/2, or phosphorylation of a substrate (e.g., ERK1/2). Alternatively, a MEK activity is an indirect activity, such as a downstream biological event mediated by interaction of the MEK protein with an MEK target molecule, e.g., ERK1/2. As MEK is in a signal transduction pathway involving ERK1/2, modulation of MEK modulates a molecule in a signal transduction pathway involving ERK1/2.

II. MEK Resistance Mutations

While treatment of cancer with MEK inhibitors, including CI-1040, is a promising therapeutic approach, patients receiving such therapies frequently relapse or fail to respond, and as a result the patients' disease progresses. As described herein, the present invention relates to the discovery of mutations in MEK that confer resistance to MEK inhibitors currently in clinical development. Acquisition of such mutations in cancer cells makes patients resistant to treatment with certain MEK inhibitors. In exemplary embodiments, the invention regards development of resistance to the MEK inhibitors CI-1040, AZD6244, PD318088, PD98059, PD334581, RDEA119, Compound A, and Compound B.

As described herein, tumors harboring a druggable oncogene dependency tend to develop on-target clinical resistance through point mutations. Elaboration of on-target resistance mechanisms has enabled the design of second-generation inhibitors with enhanced potency against a range of resistant variants. Toward this end, most resistance mutations identified herein populate the MEK allosteric drug binding pocket adjacent to the ATP binding motif. Some first-generation MEK inhibitors, e.g., aryl amine inhibitors, function by locking MEK into a "closed" but inactive conformation, in which the activation loop causes the C helix to become externally rotated and displaced. Without wishing to be bound by theory, MEK mutations may introduce resistance through direct interference of drug binding or by forcing the C helix towards a closed conformation that disrupts the binding pocket. The design of second-generation MEK inhibitors, e.g., ATP-competitive inhibitors or novel allosteric modulators, may override resistance to this mode of non-competitive kinase inhibition.

The clinical emergence of a resistant MEK1 mutation in metastatic $BRAF^{V600E}$ melanoma as described herein suggests that the biological relevance of RAF/MEK-associated dependency is maintained even in advanced stages of malignancy. Thus, the failure of first-generation RAF or MEK inhibitors to elicit durable tumor responses in many $BRAF^{V600E}$ melanomas may indicate suboptimal drug potency or pharmacodynamics in the clinical setting. Based on the findings described herein, treatment modalities involving targeted agents in RAF- or MEK-driven tumors may benefit from more potent drugs, altered dosing of existing drugs, or combined RAF and MEK inhibition. These therapeutic innovations, together with robust tumor genomic profiling to stratify patients, should speed the advent of personalized cancer treatment in cancers with "druggable" oncogene mutations.

(A) Identification of MEK Mutations Conferring Resistance to MEK Inhibitors

In various embodiments, the present invention relates to methods of identifying mutations in a MEK polypeptide, or mutations in a nucleic acid molecule encoding the MEK polypeptide, that confer resistance of the MEK polypeptide to drugs that inhibit MEK activity. A "mutant MEK polypeptide," as referenced herein, includes a MEK polypeptide containing one or more mutations that confer resistance to one or more known MEK inhibitors. Likewise, a "mutant MEK nucleic acid molecule," as referenced herein, includes a nucleic acid molecule that encodes a mutant MEK polypeptide. Nucleic acid molecules encoding MEK polypeptides that contain one or more mutations can be created using any suitable method known in the art, including, for example, random mutagenesis or site-directed mutagenesis of a wild-type MEK nucleic acid sequence, which can be conducted in E. coli. In exemplary embodiments, the wild-type MEK nucleic acid sequence is a human wild-type MEK nucleic acid sequence. In specific embodiments the wild-type MEK nucleic acid sequence is wild-type human MEK1 (SEQ ID NO:1) or wild-type human MEK2 (SEQ ID NO:3). The mutant MEK nucleic acid molecules can then be screened in cells otherwise sensitive to treatment with a MEK inhibitor to identify a nucleic acid that encodes a mutant MEK polypeptide that is resistant to treatment with the MEK inhibitor.

Any suitable method can be used to screen mutant MEK nucleic acids and mutant MEK polypeptides for resistance to treatment with a MEK inhibitor. For example, a nucleic acid molecule encoding a mutant MEK polypeptide can be expressed in cells otherwise sensitive to treatment with a MEK inhibitor. An exemplary cell line useful for this purpose is the melanoma cell line A375. Following expression of the mutant MEK polypeptide, the cells can be treated with a MEK inhibitor. The activity of the mutant MEK polypeptide can then be measured and compared to the activity of a wild-type MEK polypeptide similarly expressed and treated with the MEK inhibitor. Activity of a MEK polypeptide can be determined by, for example, measuring proliferation or viability of cells following treatment with the MEK inhibitor, wherein proliferation or viability are positively correlated with MEK activity. Cell growth, proliferation, or viability can be determined using any suitable method known in the art. In one embodiment, cell growth can be determined using well-based cell proliferation/viability assays such as MTS or Cell Titer GLo, in which cell growth in the presence of a MEK inhibitor is expressed as a percentage of that observed in untreated cells cultured in the absence of the MEK inhibitor. In certain embodiments, resistance is defined as a shift in the GI50 value of at least 2 fold, more preferably at least 3 fold, most preferably at least 4-5 fold, with respect to a suitable control. In other embodiments, resistance is defined as a GI50 value of ~1 uM). Activity of a MEK polypeptide can also be measured by, for example, determining the relative amount of phosphorylated ERK1/2 present in the cell following treatment with the MEK inhibitor. Activity of a wild-type or mutant MEK polypeptide can also be determined using an in vitro phosphorylation assay, in which MEK activity is determined by measuring the proportion of phosphorylated ERK 1/2 substrate in the assay following treatment with the MEK inhibitor. A mutant MEK polypeptide having greater activity than a wild-type MEK polypeptide following treatment with a MEK inhibitor is identified as containing a mutation that confers resistance to a MEK inhibitor. The mutation conferring resistance to a MEK inhibitor can then be identified by sequencing the nucleic acid encoding the mutant MEK polypeptide, or by sequencing the mutant MEK polypeptide directly.

In this manner, several amino acid residues of the human MEK1 polypeptide were identified that, when mutated, confer resistance to the MEK inhibitor CI-1040. These amino acid residues include one or more of the following: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G, 399H, 56Q, 99I, 104K, 113R, 120E, 128G, 133F, 215L, 237G, 326P, and 368E. In certain embodiments, the mutant MEK polypeptides of the invention contain a mutation with respect to the wild-type human MEK1 polypeptide sequence at one or more of these amino acid residues. In related embodiments, the mutant MEK nucleic acid molecules of the invention contain a mutation with respect to the wild-type human MEK1 nucleic acid sequence at one or more nucleotides encoding one or more of the these amino acid residues. In exemplary embodiments, the mutant MEK polypeptides of the invention contain one of more of the following resistance mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L, 399H>D, 56Q>P, 99I>T, 104K>N, 113R>S, 120E>D, 128G>D, 133F>L, 215L>P, 237G>V, 326P>L and 368E>K. In other exemplary embodiments, the mutant MEK nucleic acid molecules of invention encode a mutant MEK polypeptide containing one or more of the following resistance mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L, 399H>D, 56Q>P, 99I>T, 104K>N, 113R>S, 120E>D, 128G>D, 133F>L, 215L>P, 237G>V, 326P>L, and 368E>K.

The MEK resistance mutations identified above also confer resistance to a MEK inhibitor when introduced at corresponding residues in MEK2. Accordingly, amino acid residues of the human MEK2 polypeptide that, when mutated, confer resistance to the MEK inhibitor CI-1040 include one or more of the following: 71D, 78L, 107I, 110A, 111I, 115I, 119L, 123H, 128P, 132G, 133F, 171G, 207E, 215V, 251W, 262V, 264R, 280G, 310M, 311D, 316M, 336G, 60Q, 103I, 108K, 117R, 124E, 132G, 137F, 219L, 241G, 334P and 376E. In certain embodiments, the mutant MEK polypeptides of the invention contain a mutation with respect to the wild-type human MEK2 polypeptide sequence at one or more of these amino acid residues. In related embodiments, the mutant MEK nucleic acid molecules of the invention contain a mutation with respect to the wild-type human MEK2 nucleic acid sequence at one or more nucleotides encoding one or more of the these amino acid residues. In exemplary embodiments, the mutant MEK polypeptides of the invention contain one of more of the following resistance mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, 336G>R, 60Q>P, 103I>T, 108K>N, 117R>S, 124E>D, 132G>D, 137F>L, 219L>P, 241G>V, 334P>L and 376E>K. In all embodiments of the invention, a mutant MEK molecule or a mutant MEK polypeptide refers to either a MEK1 or MEK2 polypeptide having one or more mutations that confer resistance to a MEK inhibitor.

As described herein, identification of mutations in MEK conferring resistance to MEK inhibitors allows the design and screening of "second generation MEK inhibitors," which are effective at inhibiting a MEK protein having one or more resistance mutations. Such second-generation MEK inhibitors are useful in many clinical and therapeutic applications, for example, in the treatment of cancer. Identification of resistance mutations in the MEK polypeptide also allows the screening of patients having a cancer in order to determine the presence or absence of one or more MEK resistance mutations in the cancer. Determining the presence or absence of one or more MEK resistance mutations in a cancer allows alteration of the treatment strategy of a cancer patient. For example, identification of one or more of the MEK resistance mutations described herein in a cancer cell-containing sample from a patient having a cancer can be used to stratify the patient to treatment with a second-generation MEK inhibitor. Identification of MEK resistance mutations also allows the screening and identification of patients having a high risk of relapse or lack of response to treatment with certain MEK inhibitors.

The foregoing MEK resistance mutations also confer resistance to inhibitors of RAF kinase, e.g., the B-RAF inhibitor PLX4720. Resistance to inhibitors of a RAF kinase can be determined, for example, by measuring the activity a mutant MEK polypeptide in the presence of a RAF inhibitor, and comparing the activity to that of a wild-type MEK polypeptide similarly treated with the RAF inhibitor. Activity of a MEK polypeptide can be determined using the methods set forth herein.

III. Methods for Identifying Second-Generation MEK Inhibitors

Identification of MEK resistance mutations allows the development and/or identification of "second-generation MEK inhibitors." As used herein, a second-generation MEK inhibitor is an agent that effectively inhibits the activity of a MEK polypeptide containing one or more mutations described herein. A second-generation MEK inhibitor may or may not inhibit the activity of a wild-type MEK polypeptide in addition to a mutant MEK polypeptide. In a preferred embodiment, a second-generation MEK inhibitor inhibits the activity of both a wild-type MEK polypeptide and a mutant MEK polypeptide. In an exemplary embodiment, a second-generation MEK inhibitor inhibits the activity of a MEK1 polypeptide containing mutations at one or more of the following amino acid residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H; and/or a MEK2 polypeptide containing mutations at one or more of the following residues 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another exemplary embodiment, a second-generation MEK inhibitor inhibits the activity of a MEK1 polypeptide containing mutations at one or more of the following amino acid residues: 56Q, 99I, 104K, 113R, 120E, 128G, 133F, 215L, 237G, 326P and 368E; and/or a MEK2 polypeptide containing mutations at one or more of the following residues: 60Q, 103I, 108K, 117R, 124E, 132G, 137F, 219L, 241G, 334P and 376E.

Accordingly, the present invention provides methods for identifying a test compound as a second-generation MEK inhibitor. In one embodiment, a compound can be identified as a second-generation MEK inhibitor by determining the relative MEK activity of a mutant MEK polypeptide in the presence or absence of the compound, with respect to a wild-type MEK polypeptide. When in the presence of a compound that is a second-generation MEK inhibitor, a mutant MEK polypeptide has a lower level of MEK activity than in the absence of the compound. When in the presence of a compound that is not a second-generation MEK inhibitor, a mutant MEK polypeptide has an equivalent or higher level of MEK activity than in the absence of the compound. In certain embodiments, MEK activity can be measured in an in vitro assay using recombinant MEK polypeptides. In other embodiments, MEK activity can be measured in an in vivo assay using cultured cells or experimental animals.

Any indicator of MEK activity is suitable for determining whether or not a compound is a second-generation MEK inhibitor. In an exemplary embodiment, MEK activity is determined by measuring phosphorylation of the MEK substrate ERK1/2, wherein a decrease in ERK1/2 phosphorylation indicates a decrease in MEK activity. In one embodiment, ERK1/2 phosphorylation is measured in a cell or cell extract. In an alternate embodiment, ERK1/2 phosphorylation is measured in an in vitro phosphorylation assay using purified or recombinant proteins. Methods of detecting ERK1/2 phosphorylation known in the art are suitable for measuring ERK1/2 phosphorylation as an indication of the activity of a MEK polypeptide or a mutant MEK polypeptide. Such methods include, but are not limited to, Western blot and mass spectroscopy. In certain embodiments, an ERK1/2 phosphorylation assay can be performed in vitro using recombinant proteins. In other embodiments, an ERK1/2 phosphorylation assay can be performed in vivo using cultured cells or experimental animals.

In one embodiment, a host cell expressing a mutant MEK polypeptide is used in the identification of a second-generation MEK inhibitor, wherein the sensitivity of the host cell to a test compound identifies the test compound as a second-generation MEK inhibitor. As used herein, the term "sensitivity of the host cell to a test compound" is intended to mean that the test compound has a measurable effect on one or more parameters including cell growth, cell proliferation, cell viability and/or intracellular signal transduction (e.g., signal transduction mediated by MEK as evidenced by, for example, phosphorylation of one or more MEK substrates, such as ERK1/2).

A compound can be identified as a second-generation MEK inhibitor by determining the viability or proliferation rate of cells expressing a mutant MEK polypeptide in the presence or absence of the compound. The cell line used in such an assay should be sensitive to a MEK inhibitor when the cell line expresses a wild-type MEK polypeptide, and should be resistant to the MEK inhibitor (i.e., a first-generation MEK inhibitor) when the cell line expresses a mutant MEK polypeptide. An exemplary cell line useful for identification of a second-generation MEK inhibitor is the melanoma cell line A375. A375 cells are sensitive to the MEK inhibitor CI-1040 when expressing a wild-type MEK polypeptide, but are resistant to CI-1040 when expressing a mutant MEK polypeptide, for example, a MEK1 polypeptide containing one or more of the following resistance mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L, 399H>D, 56Q>P, 99I>T, 104K>N, 113R>S, 120E>D, 128G>D, 133F>L, 215L>P, 237G>V, 326P>L and 368E>K; or a MEK2 polypeptide containing one or more of the following resistance mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, 336G>R, 60Q>P, 103I>T, 108K>N, 117R>S, 124E>D, 132G>D, 137F>L, 219L>P, 241G>V, 334P>L and 376E>K.

When in the presence of a compound that is a second-generation MEK inhibitor, a cell line expressing a mutant MEK polypeptide has a lower viability or proliferation rate than in the absence of the compound, and/or a lower viability or proliferation rate than a cell line expressing a wild type MEK polypeptide in the presence of the compound. When in the presence of a compound that is not a second-generation MEK inhibitor, a cell line expressing a mutant MEK polypeptide has an equivalent or higher viability or proliferation rate than in the absence of the compound, and/or an equivalent or higher viability or proliferation rate than a cell line expressing a wild type MEK polypeptide in the presence of the compound. Methods of measuring cell viability and/or proliferation rate known in the art are suitable for determining the sensitivity of a cell line expressing a MEK polypeptide or a mutant MEK polypeptide to a test compound. Such methods include, but are not limited to, measurement of Trypan blue exclusion, metabolism of tetrazolium compounds, tritiated thymidine incorporation, BrdU incorporation, glucose uptake, ATP concentration, and level of apoptosis. In one embodiment, cell proliferation can be determined using well-based cell proliferation/viability assays such as MTS or Cell Titer GLo. In certain embodiments, sensitivity is defined as a shift in the GI50 value of at least 2 fold, more preferably at least 3 fold, most preferably at lease 4-5 fold, with respect to a suitable control.

Accordingly, in one embodiment, the invention provides a method of identifying a compound that is a second generation MEK inhibitor, comprising providing an assay composition comprising a MEK substrate and a MEK polypeptide having one or more mutations with respect to a wild-type MEK polypeptide, contacting the assay composition with a test compound under conditions that permit phosphorylation of the MEK substrate in the absence of the test compound, and determining the effect of the compound of phosphorylation of the MEK substrate, wherein downmodulation of phosphorylation of the MEK substrate as compared to a suitable control identifies the compound as a second generation MEK inhibitor. A compound identified in this way is a compound useful for treating a cancer, e.g., a cancer in which a mutant MEK polypeptide has been detected. A MEK polypeptide useful in the foregoing methods is a MEK polypeptide containing one or more mutations which confer resistance to the MEK inhibitors CI-1040, AZD6244, PD318088, PD98059, PD334581, RDEA119, Compound A, and Compound B, e.g., a MEK polypeptide containing one or more of the mutations described herein. A MEK substrate useful in the foregoing methods is ERK1/2. A decrease, reduction, or downmodulation of ERK1/2 phosphorylation is an indication that the compound is a MEK inhibitor. The foregoing methods can be performed in vitro wherein the MEK polypeptide and the MEK substrate are isolated or purified proteins. The foregoing methods can also be performed in vitro wherein the MEK polypeptide and the MEK substrate are components of a cell extract. In this embodiment, the assay composition is a cell extract. A suitable control is any control that would be apparent to a skilled person performing the method, and includes, for example, a similar or identical assay composition not treated with a test compound or treated with a control compound, or an analogous assay composition or cell extract comprising a "wild-type" MEK1 or MEK2 polypeptide.

In another embodiment, the invention provides a method of identifying a compound that is a second generation MEK inhibitor, comprising providing a cell comprising a mutant MEK polypeptide, contacting the cell with a test compound, and determining the effect of the compound on ERK1/2 phosphorylation or cell proliferation, wherein a decrease, reduction, or downmodulation of ERK1/2 phosphorylation or cell proliferation as compared to an appropriate control identifies the compound as a second generation MEK inhibitor. A compound identified in this way is a compound useful for treating a cancer, e.g., a cancer in which a mutant MEK polypeptide has been detected. A suitable control is any control that would be apparent to a skilled person performing the method, and includes, for example, a similar or identical cell not treated with a test compound or treated with a control compound, or an analogous cell or cell extract in which recombinant, "wild-type" MEK1 or MEK2 was expressed.

In one embodiment, the test compound used in the foregoing methods is a MEK inhibitor that inhibits a biological activity of a wild type MEK polypeptide. MEK inhibitors that are second generation MEK inhibitors are described herein.

In another embodiment, the test compound is a member of a library of test compounds. A "library of test compounds" refers to a panel comprising a multiplicity of test compounds. An approach for the synthesis of molecular libraries of small organic molecules has been described (Carell et al. (1994). *Angew. Chem. Int. Ed. Engl.* 33:2059; Carell et al. (1994) *Angew. Chem. Int. Ed. Engl.* 33:2061). The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68-; and in Gallop et al. (1994); *J. Med. Chem.* 37:1233-. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library. Exemplary compounds that can be screened for activity include, but are not limited to, peptides, nucleic acids, carbohydrates, small organic molecules, and natural product extract libraries.

Second generation MEK inhibitors can also be rationally designed based on the structure of MEK1 or MEK2 alleles containing one or more of the resistance mutations described herein. As described herein, residues of MEK that confer resistance to MEK inhibitors are located in or near the C-helix, the activation loop, and the ATP binding pocket of the MEK polypeptide. This region of the MEK polypeptide is the same region bound by the first-generation MEK inhibitors CI-1040 and AZD6244. Identification of MEK1 and MEK2 mutant alleles conferring resistance to MEK inhibitors allows comparison between the structure of the C-helix, activation loop and ATP binding pocket of the mutant alleles and the wild-type protein. Knowledge of the altered structural features that confer resistance to first-generation MEK inhibitors allows rational design and construction of ligands, including inhibitors, that will bind the C-helix, activation loop, and/or the ATP binding pocket of the mutant alleles. Such inhibitors can be designed such that they bind both the mutant and wild-type MEK alleles. Inhibitors designed to bind the C-helix, activation loop, and/or ATP binding pocket of MEK alleles containing one or mutations described herein are second-generation MEK inhibitors. The ability of such rationally designed inhibitors to inhibit a biological activity of a mutant MEK polypeptide can be confirmed using the in vitro and/or in vivo assays described herein.

The structure of a MEK polypeptide containing one or more of the resistance mutations described herein can be determined by computer-assisted modeling, or by determining the crystal or solution structure of the mutant MEK polypeptide. Any suitable method known in the art can be used to determine the structure of a mutant MEK polypeptide.

Exemplary computer-assisted modeling methods include the use of software programs such as PYMOL, CAVITY (described in J. Comp. Aided. Mol. Des. (1990) 4:337-354 (incorporated herein by reference)) and Discovery Studio® (Accelrys, San Diego, Calif.). Additional techniques useful for computer-assisted molecular modeling are described in J BUON. (2007) 12 Suppl 1:S101-18 (incorporated herein by reference). Computer-based analysis of a protein with a known structure can also be used to identify molecules which will bind to the protein. Such methods rank molecules based on their shape complementary to a receptor site. For example, using a 3-D database, a program such as DOCK can be used to identify molecules which will bind to XBP-1, IRE-1 alpha, and/or EDEM. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445. In addition, the electronic complementarity of a molecule to a targeted protein can also be analyzed to identify molecules which bind to the target. This can be determined using, for example, a molecular mechanics force field as described in Meng et al. (1992) J. Computer Chem. 13:505 and Meng et al. (1993) Proteins 17:266. Other programs which can be used include CLIX which uses a GRID force field in docking of putative ligands (see, for example, Lawrence et al. (1992) Proteins 12:31; Goodford et al. (1985) J. Med. Chem. 28:849; and Boobbyer et al. (1989) J. Med. Chem. 32:1083, incorporated by reference in their entirety).

Crystallization can be performed by any crystallization method including, but not limited to batch, dialysis and vapor diffusion (e.g., sitting drop and hanging drop) methods. Micro, macro and/or streak seeding of crystals can also be performed to facilitate crystallization. Crystals comprising MEK1 or MEK2 mutant alleles can be formed by a variety of different methods known in the art. For example, crystallizations can be performed by batch, dialysis, and vapor diffusion (sitting drop and hanging drop) methods. A detailed description of basic protein crystallization setups can be found in McRee, D., *Practical Protein Crystallography*, $2^{nd}$ Ed. (1999), Academic Press Inc. Further descriptions regarding performing crystallization experiments are provided in Stevens et al. (2000) Curr. Opin. Struct. Biol.: 10(5):558-63, and U.S. Pat. Nos. 6,296,673; 5,419,278; and 5,096,676, the entire contents of which are incorporated herein by reference. Such crystals can be used to perform X-ray or neutron diffraction analysis in order to determine the three-dimensional structure of MEK mutant alleles. A solution structure of a MEK polypeptide or mutant MEK polypeptide can be identified using nuclear magnetic resonance spectroscopy using techniques known in the art. Suitable methods for polypeptide structure determination by X-Ray crystallography or NMR spectroscopy are described in Brunger et al., (1998) "Crystallography & NMR system (CNS): A new software system for macromolecular structure determination," Acta Crystallogr D54, 905-921; Brunger et al. (1987) "Solution of a Protein Crystal Structure With a Model Obtained From NMR Interproton Distance Restraints," Science 235, 1049-1053; Drenth, "Principles of Protein X-ray Crystallography," (1994), Springer-Verlag. pp. 1-19; and Narula et al. (1995) "Solution structure of the C-terminal SH2 domain of the human tyrosine kinase Syk complexed with a phosphotyrosine pentapeptide," Structure 3, 1061-1073, incorporated herein by reference in their entirety. Upon identification of the crystal or solution structure of a mutant MEK polypeptide, inhibitors of the mutant MEK polypeptide can be identified using the computer assisted modeling approaches described above.

Second-generation MEK inhibitors identified by the foregoing methods are useful for treating a disease or condition associated with expression of a wild-type and/or mutant MEK polypeptide. For example, second-generation MEK inhibitors are useful for treating a cancer in a subject, particularly a cancer in which a mutant MEK polypeptide has been identified. In an exemplary embodiment, second-generation MEK inhibitors are useful for treating a cancer containing a MEK1 polypeptide having a mutation at one or more of the following amino acid residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H, and/or a MEK2 polypeptide having a mutation at one or more of the following amino acid residues: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another exemplary embodiment, second-generation MEK inhibitors are useful for treating a cancer containing a MEK1 polypeptide having a mutation at one or more of the following amino acid residues: 56Q, 99I, 104K, 113R, 120E, 128G, 133F, 215L, 237G, 326P, and 368E; and/or a MEK2 polypeptide having a mutation at one or more of the following amino acid residues: 60Q, 103I, 108K, 117R, 124E, 132G, 137F, 219L, 241G, 334P and 376E. In a related embodiment, second-generation MEK inhibitors are useful for treating a cancer containing a MEK1 polypeptide having one or more of the following mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D, and/or a MEK2 polypeptide having one or more of the following mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In another exemplary embodiment, second-generation MEK inhibitors are useful for treating a cancer containing a MEK1 polypeptide having one or more of the following mutations: 56Q>P, 99I>T, 104K>N, 113R>S, 120E>D, 128G>D, 133F>L, 215L>P, 237G>V, 326P>L, and 368E>K, and/or a MEK2 polypeptide having one or more of the following mutations: 60Q>P, 103I>T, 108K>N, 117R>S, 124E>D, 132G>D, 137F>L, 219L>P, 241G>V, 334P>L, and 376E>K.

IV. Isolated Nucleic Acid Molecules

The present invention concerns polynucleotides or nucleic acid molecules relating to the MEK gene and its respective gene product. These polynucleotides or nucleic acid molecules are isolatable and purifiable from mammalian cells. In particular aspects of the invention, the isolated MEK nucleic acid molecules described herein comprise one or more mutations conferring resistance to a MEK inhibitor. A "mutant MEK nucleic acid molecule," as referenced herein, includes a MEK nucleic acid molecule that encodes a mutant MEK polypeptide, i.e., a MEK polypeptide containing one or more mutations that confer resistance to one or more known MEK inhibitors.

It is contemplated that an isolated and purified MEK nucleic acid molecule, e.g., a mutant MEK nucleic acid molecule, can take the form of RNA or DNA. As used herein, the term "RNA transcript" refers to an RNA molecule that is the product of transcription from a DNA nucleic acid molecule. Such a transcript can encode for one or more polypeptides.

As used in this application, the term "polynucleotide" refers to a nucleic acid molecule, RNA or DNA, that has been isolated, such as being free of total genomic nucleic acid. Therefore, a "polynucleotide encoding MEK" refers to a nucleic acid segment that contains MEK coding sequences, yet is isolated away from, or purified and free of, total genomic DNA and proteins. When the present application refers to the function or activity of a MEK-encoding polynucleotide or nucleic acid, it is meant that the polynucleotide encodes a molecule that is capable of performing an activity of a wild-type MEK polypeptide, for example, phosphorylation of the ERK1/2 substrate.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 1989; Ausubel, 1996). There can be times when the full or partial genomic sequence is preferred. Alternatively, cDNA can be advantageous because it represents coding regions of a polypeptide and eliminates introns and other regulatory regions.

It also is contemplated that a given MEK-encoding nucleic acid or MEK gene from a given cell may be represented by natural variants or strains that have slightly different nucleic acid sequences but, nonetheless, encode an active MEK polypeptide. In a preferred embodiment, the active MEK polypeptide is an active human MEK polypeptide. In particularly preferred embodiments, the active MEK polypeptide is a mutant MEK polypeptide that has an activity of a wild-type MEK polypeptide, but which is resistant to one or more known MEK inhibitors. Consequently, certain aspects of the present invention encompass derivatives of MEK with minimal amino acid changes, but that possess the same biological function.

The term "gene" is used for simplicity to refer to a functional protein, polypeptide, or peptide-encoding unit. As will be understood by those in the art, this functional term includes genomic sequences, cDNA sequences, and smaller engineered gene segments that express, or can be adapted to express, proteins, polypeptides, domains, fusion proteins, and mutant proteins. The nucleic acid molecule encoding MEK can comprise a contiguous nucleic acid sequence of the following lengths: at least about 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences can be identical or complementary to, for example, SEQ ID NO:1, or a fragment thereof.

Various embodiments of the invention relate to genetic mutations in MEK. As used herein, a mutation refers to an addition, deletion, or substitution of a single nucleotide at a site in a MEK nucleic acid molecule. In an exemplary embodiment, a mutant MEK nucleic acid molecule contains one or more mutations that confer resistance to a particular therapy, such as a MEK inhibitor, e.g., CI-1040. In a related embodiment, a mutant MEK nucleic acid molecule contains one or more mutations such that the mutant MEK nucleic acid molecule encodes a mutant MEK polypeptide, wherein the mutant MEK polypeptide contains one or more mutations that confer resistance to a particular therapy, such as a MEK inhibitor, e.g., CI-1040. Thus, in particular aspects of the invention, an alteration in a sequence results in a change that affects the properties of a polypeptide encoded by the sequence such that at least some resistance to therapy, such as therapy with a MEK inhibitor, occurs as a result.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode mutant MEK polypeptides or peptides that include within its amino acid sequence a contiguous amino acid sequence in accordance with, or essentially corresponding to mutant MEK polypeptides. In exemplary embodiments, the invention concerns isolated DNA segments and recombinant vectors incorporating DNA sequences that encode a MEK protein, polypeptide or peptide that includes within its amino acid sequence a contiguous amino acid sequence of a MEK polypeptide comprising one or more mutations that confer resistance to a MEK inhibitor. In certain embodiments, the one or more mutations occur at positions 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G or 399H of a MEK1 polypeptide. In other embodiments, the one or more mutations occur at positions 56Q, 99I, 104K, 113R, 120E, 128G, 133F, 215L, 237G, 326P or 368E of a MEK1 polypeptide. In other embodiments, the one or more MEK1 mutations include the following: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L or 399H>D. In other embodiments, the one or more MEK1 mutations include the following: 56Q>P, 99I>T, 104K>N, 113R>S, 120E>D, 128G>D, 133F>L, 215L>P, 237G>V, 326P>L or 368E>K. In certain embodiments, the one or more mutations occur at positions 71D, 78L, 107I, 110A, 111I, 115I, 119L, 123H, 128P, 132G, 133F, 171G, 207E, 215V, 251W, 262V, 264R, 280G, 310M, 311D, 316M or 336G of a MEK2 polypeptide. In other embodiments, the one or more mutations occur at positions 60Q, 103I, 108K, 117R, 124E, 132G, 137F, 219L, 241G, 334P or 376E of a MEK2 polypeptide. In other embodiments, the one or more MEK2 mutations include the following: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In other embodiments, the one or more MEK2 mutations include the following: 60Q>P, 103I>T, 108K>N, 117R>S, 124E>D, 132G>D, 137F>L, 219L>P, 241G>V, 334P>L, 376E>K.

The nucleic acid segments used in the present invention, regardless of the length of the coding sequence itself, can be combined with other DNA or RNA sequences, such as promoters, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol.

It is contemplated that the nucleic acid constructs of the present invention encode a MEK polypeptide or a mutant MEK polypeptide. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs can be prepared that include a contiguous stretch of nucleotides identical to or complementary to all or part of a MEK gene. A nucleic acid construct can comprise at least 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100, 000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000, 002, etc. Non-limiting examples of intermediate ranges include about 3 to about 32, about 150 to about 500,001, about 3,032 to about 7,145, about 5,000 to about 15,000, about 20,007 to about 1,000,003, etc.

Certain embodiments of the present invention concern various nucleic acids, including vectors, promoters, therapeutic nucleic acids, and other nucleic acid elements involved in transformation and expression in cells. In certain aspects, a nucleic acid comprises a wild-type or a mutant nucleic acid. In particular aspects, a nucleic acid encodes for or comprises a transcribed nucleic acid.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the MEK gene, other regulatory regions such as enhancers for MEK are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid can encompass a double-stranded molecule or a triple-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

A nucleic acid can be made by any technique known to one of ordinary skill in the art, for example, by chemical synthesis, or by enzymatic production or biological production.

Non-limiting examples of a synthetic nucleic acid (e.g., a synthetic MEK primer that facilitates identification of a mutation conferring resistance to a MEK inhibitor), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotides can be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in an amplification reactions such as PCR (see for example, U.S. Pat. Nos. 4,683,202 and 4,682,195, each incorporated herein by reference), or one produced by synthesis of oligonucleotides, as described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

A nucleic acid can be purified on polyacrylamide gels, cesium chloride centrifugation gradients, or by any other means known to one of ordinary skill in the art as part of assessment for a mutation that confers resistance to MEK (see for example, Sambrook et al., 1989, incorporated herein by reference). In preferred aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, the bulk of cellular components or in vitro reaction components, including, for example, macromolecules such as lipids or proteins, small biological molecules, and the like.

V. Expression Vectors and Host Cells

The present invention encompasses expression vector compositions and the use of such vectors to encode for a MEK polypeptide, e.g., a mutant MEK polypeptide, as well as host cell compositions into which such expression vectors have been introduced. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors can contain nucleic acid sequences that serve other functions as well and are described infra.

1. Promoters and Enhancers

A "promoter" is a control sequence that is a region of a nucleic acid sequence at which initiation and rate of transcription are controlled. It can contain genetic elements at which regulatory proteins and molecules can bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter can be one naturally associated with a gene or sequence, as can be obtained by isolating the 5' non-coding sequences located upstream of the coding segment and/or exon. Such a promoter can be referred to as "endogenous." Similarly, an enhancer can be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed can be constitutive, tissue-specific, inducible, and/or useful under the appropriate conditions to direct high level expression of the introduced DNA segment. The promoter can be heterologous or exogenous, for example, a non-MEK promoter with respect to MEK encoding sequence. In some examples, a prokaryotic promoter is employed for use with in vitro transcription of a desired sequence. Prokaryotic promoters for use with many commercially available systems include T7, T3, and Sp6.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements. In certain embodiments of the invention, the use of internal ribosome entry sites (IRES) elements are used to create multigene, or polycistronic, messages.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences can require donor and/or acceptor splicing sites to ensure proper processing of the transcript for protein expression (see, for example, Chandler et al., 1997, herein incorporated by reference).

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

6. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence can be employed. Preferred embodiments include the SV40 polyadenylation signal and/or the bovine growth hormone polyadenylation signal, convenient and/or known to function well in various target cells. Polyadenylation can increase the stability of the transcript or may facilitate cytoplasmic transport.

Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, the cells containing a nucleic acid construct of the present invention can be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) can be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. A cell comprising a MEK polynucleotide, either mutated or wild-type, can be employed in the invention. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. A "recombinant host cell" refers to a host cell that carries a recombinant nucleic acid, i.e. a nucleic acid that has been manipulated in vitro or that is a replicated copy of a nucleic acid that has been so manipulated.

A host cell can be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE™ Competent Cells and Solopack™ Gold Cells (Stratagene®, La Jolla). Alternatively, bacterial cells such as E. coli LE392 could be used as host cells for phage viruses.

A preferred eukaryotic host cell of the invention is the melanoma cell line A375, wherein the cell has been transformed with an expression vector encoding a MEK polypeptide, e.g., a mutant MEK polypeptide of the invention.

10. Expression Systems

Numerous expression systems exist that comprise at least a part or all of the compositions discussed above. Prokaryote- and/or eukaryote-based systems can be employed for use with the present invention to produce MEK nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac™ 2.0 from Invitrogen™ and BacPack™ Baculovirus Expression System from Clontech™.

Other examples of expression systems include Stratagene's Complete Control™ Inducible Mammalian Expression System, which involves a synthetic ecdysone-inducible receptor, or its pET Expression System, an E. coli expression system. Another example of an inducible expression system is available from Invitrogen, which carries the T-Rex™ (tetracycline-regulated expression) System, an inducible mammalian expression system that uses the full-length CMV promoter. The Tet-On™ and Tet-Off™ systems from Clontech™ can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

Invitrogen also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

VI. Isolated Polypeptide Molecules

Another aspect of the invention pertains to isolated and/or purified MEK proteins, and biologically active portions thereof. In particular aspects of the invention, the MEK polypeptides described herein comprise one or more mutations conferring resistance to a MEK inhibitor. A "mutant MEK polypeptide", as referenced herein, includes a MEK polypeptide containing one or more mutations that confer resistance to one or more known MEK inhibitors.

An "isolated" or "purified" protein or biologically active portion thereof is substantially free of cellular material when produced by recombinant DNA techniques, or chemical precursors or other chemicals when chemically synthesized. The language "substantially free of cellular material" includes preparations of MEK proteins in which the protein is separated from cellular components of the cells in which it is naturally or recombinantly produced. In one embodiment, the language "substantially free of cellular material" includes preparations of MEK protein having less than about 30% (by dry weight) of non-MEK protein (also referred to herein as a "contaminating protein"), more preferably less than about 20% of non-MEK protein, still more preferably less than about 10% of non-MEK protein, and most preferably less than about 5% of non-MEK protein. When the MEK protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of MEK protein in which the protein is separated from chemical precursors or other chemicals which are involved in the synthesis of the protein. In one embodiment, the language "substantially free of chemical precursors or other chemicals" includes preparations of MEK protein having less than about 30% (by dry weight) of chemical precursors or non-MEK chemicals, more preferably less than about 20% chemical precursors or non-MEK chemicals, still more preferably less than about 10% chemical precursors or non-MEK chemicals, and most preferably less than about 5% chemical precursors or non-MEK chemicals.

Biologically active portions of a MEK protein include peptides comprising amino acid sequences derived from the amino acid sequence of a MEK protein, e.g., the amino acid sequence shown in SEQ ID NOs:2 and 4, or the amino acid sequence of a protein homologous to a MEK protein, which include fewer amino acids than a full length MEK protein or the full length protein which is homologous to a MEK protein, and exhibit at least one activity of a MEK protein. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a MEK protein. Moreover, other biologically active portions, in which other regions of the protein are deleted, can be prepared by recombinant techniques and evaluated for one or more of the activities described herein. Preferably, the biologically active portions of a MEK protein include one or more selected domains/motifs or portions thereof having biological activity. In preferred embodiments, biologically active portions of a MEK protein comprise one or more mutations with respect to a wild-type MEK sequence, wherein said one or more mutations, when present in a full-length mutant MEK polypeptide, confer resistance of the mutant MEK polypeptide to known MEK inhibitors. In exemplary embodiments, the mutations occur at amino acids corresponding to one or more of the following positions in a wild-type MEK1 protein: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H; or in one or more of the following positions in a wild-type MEK2 protein: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In other embodiments, the mutations occur at amino acids corresponding to one or more of the following positions in a wild-type MEK1 protein: 56Q, 99I, 104K, 113R, 120E, 128G, 133F, 215L, 237G, 326P and 368E; or in one or more of the following positions in a wild-type MEK2 protein: 60Q, 103I, 108K, 117R, 124E, 132G, 137F, 219L, 241G, 334P and 376E. In a related embodiment, the mutations include one or more of the following MEK1 residues: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D; or one or more of the following MEK2 residues: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In another embodiment, the mutations include one or more of the following MEK1 residues: 56Q>P, 99I>T, 104K>N, 113R>S, 120E>D, 128G>D, 133F>L, 215L>P, 237G>V, 326P>L and 368E>K; or one or more of the following MEK2 residues: 60Q>P, 103I>T, 108K>N, 117R>S, 124E>D, 132G>D, 137F>L, 219L>P, 241G>V, 334P>L, 376E>K.

MEK proteins are preferably produced by recombinant DNA techniques. For example, a nucleic acid molecule encoding the protein is cloned into an expression vector (as described above), the expression vector is introduced into a host cell (as described above) and the MEK protein is expressed in the host cell. The MEK protein can then be isolated from the cells by an appropriate purification scheme using standard protein purification techniques. Alternative to recombinant expression, a MEK protein, polypeptide, or peptide can be synthesized chemically using standard peptide synthesis techniques. Moreover, a native MEK protein and/or a mutant MEK protein can be isolated from cells (e.g., cancer cells), for example using an anti-MEK antibody, which can be produced by standard techniques utilizing a MEK protein or fragment thereof of this invention.

The invention also provides MEK chimeric or fusion proteins. As used herein, a MEK "chimeric protein" or "fusion protein" comprises a MEK polypeptide operatively linked to a non-MEK polypeptide. A "MEK polypeptide" refers to a polypeptide having an amino acid sequence corresponding to a MEK protein, whereas a "non-MEK polypeptide" refers to a polypeptide having an amino acid sequence corresponding to a protein which is not substantially homologous to the MEK protein, e.g., a protein which is substantially different from the MEK protein, which does not display a MEK activity and which is derived from the same or a different organism. Within the fusion protein, the term "operatively linked" is intended to indicate that the MEK polypeptide and the non-MEK polypeptide are fused in-frame to each other. The non-MEK polypeptide can be fused to the N-terminus or C-terminus of the MEK polypeptide. For example, in one embodiment the fusion protein is a GST-MEK fusion protein in which the MEK sequences are fused to the C-terminus of the GST sequences. Such fusion proteins can facilitate the purification of recombinant MEK proteins. In another embodiment, the fusion protein is a MEK protein containing a heterologous signal sequence at its N-terminus. In certain host cells (e.g., mammalian host cells), expression and/or secretion of a MEK protein can be increased through use of a heterologous signal sequence.

Preferably, a MEK chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A MEK-encoding nucleic acid can be cloned into such an expression vector such that the fusion moiety is linked in-frame to the MEK protein.

In a preferred embodiment, the isolated MEK polypeptides of the invention contain one or more mutations (e.g., substitutions or deletions) with respect to a wild-type MEK polypeptide sequence. In one embodiment, the mutant MEK polypeptides contain one or more mutations with respect to a human wild-type MEK polypeptide sequence (SEQ ID NO:2). In a particularly preferred embodiment, the one or more mutations confer resistance to a MEK inhibitor. In an exemplary embodiment, the MEK inhibitor is CI-1040. A mutant MEK protein of the invention exhibits a biological activity characteristic of a wild-type MEK protein. Such a biological activity can include, for example, phosphorylation of ERK1/2. Exemplary mutant MEK polypeptides of the invention include MEK polypeptides comprising a mutation at one or more of the following amino acid residues with respect to the wild type human MEK1 polypeptide: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H, or at one or more of the following amino acid residues with respect to the wild-type human MEK2 polypeptide: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another embodiment, exemplary mutant MEK polypeptides of the invention include MEK polypeptides comprising a mutation at one or more of the following amino acid residues with respect to the wild type human MEK1 polypeptide: 56Q, 99I, 104K, 113R, 120E, 128G, 133F, 215L, 237G, 326P, and 368E, or at one or more of the following amino acid residues with respect to the wild-type human MEK2 polypeptide: 60Q, 103I, 108K, 117R, 124E, 132G, 137F, 219L, 241G, 334P, and 376E. Exemplary mutant MEK polypeptides of the invention also include MEK polypeptides comprising one or more of the following amino acid substitutions with respect to the wild type human MEK1 protein: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D; or the wild-type MEK2 protein: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In another embodiment, exemplary mutant MEK polypeptides of the invention also include MEK polypeptides comprising one or more of the following amino acid substitutions with respect to the wild type human MEK1 protein: 56Q>P, 99I>T, 104K>N, 113R>S, 120E>D, 128G>D, 133F>L, 215L>P, 237G>V, 326P>L and 368E>K; or the wild-type MEK2 protein: 60Q>P, 103I>T, 108K>N, 117R>S, 124E>D, 132G>D, 137F>L, 219L>P, 241G>V, 334P>L, 376E>K.

Mutant MEK proteins can be generated by mutagenesis of a wild-type MEK protein, or of the nucleic acid molecule encoding a wild-type MEK protein. Mutant MEK proteins can also be identified by screening combinatorial libraries of MEK mutants for a mutant MEK protein having a desired activity, e.g., resistance to a MEK inhibitor. Several techniques are known in the art for screening gene products of combinatorial libraries made by point mutations or truncation, and for screening cDNA libraries for gene products having a selected property. Such techniques are adaptable for rapid screening of the gene libraries generated by combinatorial mutagenesis. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

VIII. Detection of Mutations

In another aspect, the invention pertains to methods of detecting the presence of a mutant MEK protein in a sample (e.g., a biological sample from a cancer patient). A variety of screening methods can be used to detect the presence of a mutant MEK protein of the invention in a sample, e.g., a nucleic acid and/or a polypeptide sample. In specific embodiments, the sample contains a cell or cell extract. In exemplary embodiments, the sample is obtained from a subject, e.g., a subject having cancer.

Methods for detecting the presence of resistance mutations in genomic DNA, cDNA, and RNA (i.e., mRNA) containing a sequence encoding a MEK protein, or biologically active portion thereof, can be used within the scope of the present invention. Likewise, methods for detecting the presence of resistance mutations in MEK polypeptides, or biologically active portions thereof, can be used within the scope of the present invention. In particular embodiments, methods including, but not limited to, the following can be used to detect the presence of a MEK1 polypeptide, or a nucleic acid molecule encoding a MEK1 polypeptide, having a mutation at one or more of the following amino acid residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G, 399H, 56Q, 99I, 104K, 113R, 120E, 128G, 133F, 215L, 237G, 326P, and 368E; or to detect the presence of a MEK2 polypeptide, or a nucleic acid molecule encoding a MEK2 polypeptide, having a mutation at one or more of the following amino acid residues: 71D, 78L, 107I, 110A, 111I, 115I, 119L, 123H, 128P, 132G, 133F, 171G, 207E, 215V, 251W, 262V, 264R, 280G, 310M, 311D, 316M, 336G, 60Q, 103I, 108K, 117R, 124E, 132G, 137F, 219L, 241G, 334P, and 376E. In exemplary embodiments, methods including, but not limited to, the following can be used to detect the presence of a MEK1 polypeptide, or a nucleic acid molecule encoding a MEK1 polypeptide, having one or more of the following mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L, 399H>D, 56Q>P, 99I>T, 104K>N, 113R>S, 120E>D, 128G>D, 133F>L, 215L>P, 237G>V, 326P>L, and 368E>K; or a MEK2 polypeptide, or a nucleic acid molecule encoding a MEK2 polypeptide, having one or more of the following mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, 336G>R, 60Q>P, 103I>T, 108K>N, 117R>S, 124E>D, 132G>D, 137F>L, 219L>P, 241G>V, 334P>L, and 376E>K.

Point mutations can be detected using any suitable method known in the art, including, for example, denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP"), polymerase chain reaction, sequencing, hybridization, or "hybrid capture" followed by pyrosequencing or single-molecule sequencing. One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations. U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. For example, Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that can be used in the practice of the present invention are disclosed in U.S. Pat. Nos. 5,849,483, 5,851,770, 5,866,337, 5,925,525 and 5,928,870, each of which is incorporated herein by reference in its entirety.

Screening methods can be performed to screen an individual for the occurrence of the mutations identified above. For example, in one embodiment, a sample (such as blood or other bodily fluid or cell or tissue sample) is taken from a patient for analysis. In an exemplary embodiment, the patient is a cancer patient. Methods suitable for processing such samples for detection of a mutation in a MEK nucleic acid or a MEK polypeptide are known in the art, and the skilled artisan may adapt the processing of such samples in accordance with the chosen method of detection. For example, when detecting the presence of mutations in a nucleic acid encoding a MEK polypeptide, biological samples (e.g., cell samples or tissue samples) may be processed such that the nucleic acid material in the sample is accessible to reagents used to detect mutations (e.g., nucleic acid probes, primers, etc.). Accordingly, in certain embodiments, the nucleic acid material in a biological sample is extracted from cells within the sample. "Extraction" of nucleic acid material as used herein refers to the process of making the nucleic acid material in a biological sample accessible to contact by reagents used for detection. For example, in a cell sample, the nucleic acid material (e.g., mRNA encoding a MEK polypeptide, DNA encoding a MEK polypeptide, etc.) is located inside the cell membrane, making it inaccessible by detection reagents added to the sample. Accordingly, extraction of the nucleic acid material by disrupting the integrity of the cell membrane is commonly employed. Exemplary means of extracting nucleic acid material from a cell are known in the art and include, but are not limited to, mechanical disruption (e.g., sonication, French press, vortexing, Dounce homogenization, etc.), and/or detergent-mediated disruption (e.g., disruption in lysis buffer containing detergents such as Triton-X-100, CHAPS, SDS, etc.). Depending on the method of detection, the nucleic acid material may or may not be isolated from other components of the sample during or following extraction. For example, for detection methods employing PCR amplification of a nucleic acid molecule encoding a MEK polypeptide, nucleic acid material that has been extracted from cells may be used without further isolation (e.g., as a component of a crude lysate). In one embodiment, a biological sample may be isolated on filter paper that is then processed using standard extraction techniques prior to PCR amplification of a nucleic acid molecule encoding a MEK polypeptide. Such filter paper can contain chemical reagents that lyse cells, and can additionally contain reagents that stabilize and protect nucleic acid material (e.g., Whatman FTA™, GE Healthcare). PCR amplification of a MEK nucleic acid molecule may be performed from samples stored on filter paper without isolation from other cellular components. In other embodiments, nucleic acid material may be isolated from other non-nucleic acid components in the sample using techniques known in the art, including, for example, those described by Sambrook, Fritsch and Maniatis, *Molecular Cloning*: Cold Spring Harbor Laboratory Press (1989), and by *Current Protocols in Molecular Biology*, eds. Ausubel et al., John Wiley & Sons (1992). As described therein, modifications to the methods of extraction and/or isolation may be used depending on the type of nucleic acid material to be assayed (e.g. DNA or RNA). Methods of detecting mutations in a MEK polypeptide also may employ extraction and/or isolation of polypeptides from a biological sample. Techniques suitable for extracting and/or isolating polypeptides from a biological sample are well known in the art and are further described in, for example, *Current Protocols in Molecular Biology*, eds. Ausubel et al., John Wiley & Sons (1992).

The presence or absence of one or more mutations described herein determines the ability of the screened individuals to resist therapy with a first-generation MEK inhibitor. According to methods provided by the invention, these results will be used to adjust and/or alter the dose of the first-generation MEK inhibitor, or to select a course of treatment using a second-generation MEK inhibitor. Effective treatment of a subject having cancer can comprise the eradication of a cancer cell, the cessation or reduction of cancer (such as solid tumor) growth rate, or the amelioration of at least one cancer symptom.

The resistance mutations in MEK polypeptides, or in nucleic acid molecules encoding MEK polypeptides, can be detected using any suitable methods known in the art, or modifications thereof, including the methods described below. Such methods include the use of allele-specific polymerase chain reaction, direct or indirect sequencing of the site, the use of restriction enzymes where the respective alleles of the site create or destroy a restriction site, the use of allele-specific hybridization probes, the use of antibodies that are specific for mutant MEK polypeptides, or any other biochemical interpretation.

1. DNA Sequencing

The most commonly used method of characterizing a mutation is direct DNA sequencing of the genetic locus that flanks and includes the polymorphism. Such analysis can be accomplished using either the "dideoxy-mediated chain termination method," also known as the "Sanger Method" (Sanger, F., et al., 1975) or the "chemical degradation method," also known as the "Maxam-Gilbert method" (Maxam, A. M., et al., 1977). Sequencing in combination with genomic sequence-specific amplification technologies, such as the polymerase chain reaction, can be utilized to facilitate the recovery of the desired genes (Mullis, K. et al., 1986; European Patent Appln. 50,424; European Patent Appln. 84,796, European Patent Application 258,017, European Patent Appln. 237,362; European Patent Appln. 201, 184; U.S. Pat. Nos. 4,683,202; 4,582,788; and 4,683,194), all of which are incorporated herein by reference. Sequencing of pooled samples can also be accomplished using Solexa/Illumina sequencing (Illumina,® San Diego, Calif.), pyrosequencing, or other single-molecule sequencing approaches. In one embodiment, mutations in the MEK gene can be detected by cloning and sequencing a MEK allele present in a sample obtained from the subject. If desired, MEK mRNA can be sequenced directly, or the polymerase chain reaction technique ("PCR") can be used to amplify MEK DNA or mRNA to produce encoding DNA ("cDNA"), and the resultant cDNA can be sequenced. PCR can also be used to selectively amplify a region of the MEK allele. Techniques that may be used to detect one or more mutations in a MEK nucleic acid include, but are not limited to, those described in Sambrook, Fritsch and Maniatis, *Molecular Cloning*: Cold Spring Harbor Laboratory Press (1989); *Current Protocols in Molecular Biology*, Ausubel et al., eds., John Wiley & Sons (1992); *PCR Protocols, Current Methods and Applications*, White, B. A., ed., Humana Press Inc. (1993), *PCR Sequencing Protocols*, Rapley R. et al., eds., Humana Press Inc. (1996)

2. Exonuclease Resistance

Other methods that can be employed to determine the identity of a nucleotide present at a mutated site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

3. Microsequencing Methods

Several other primer-guided nucleotide incorporation procedures for assaying mutated sites in DNA have been described (Komher, J. S. et al., 1989; Sokolov, B. P., 1990; Syvanen 1990; Kuppuswamy et al., 1991; Prezant et al., 1992; Ugozzoll, L. et al., 1992; Nyren et al., 1993). These methods rely on the incorporation of labeled deoxynucleotides to discriminate between bases at a mutated site. As the signal is proportional to the number of deoxynucleotides incorporated, mutations that occur in runs of the same nucleotide result in a signal that is proportional to the length of the run (Syvanen et al., 1993).

4. Extension in Solution

French Patent 2,650,840 and PCT Application No. WO91/02087 discuss a solution-based method for determining the identity of the nucleotide of a mutated site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

5. Genetic Bit™ Analysis or Solid-Phase Extension

PCT Appln. No. 92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here, the primer or the target molecule is immobilized to a solid phase.

6. Oligonucleotide Ligation Assay (OLA)

Oligonucleotide Ligation Assay is a solid phase method that uses different methodology than that described above (Landegren et al., 1988). Two oligonucleotides capable of hybridizing to abutting sequences of a single strand of a target DNA are utilized. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide using avidin. Other nucleic acid detection assays, based on this method, combined with PCR are also described (Nickerson et al., 1990). Here, PCR is used to achieve the exponential amplification of target DNA, which is then detected using the OLA.

7. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone, and unlike the polymerase-based assays, this method enhances the specificity of the polymerase step by combining it with a second hybridization and a ligation step for a signal to be attached to the solid phase.

8. Methods of Nucleic Acid Transfer

For some methods of the present invention, methods of nucleic acid transfer can be employed. Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); or by desiccation/inhibition-mediated DNA uptake (Potrykus et al., 1985). Through the application of techniques such as these, organelle(s), cell(s), tissue(s) or organism(s) can be stably or transiently transformed.

9. Allele-Specific Antibodies

MEK1 or MEK2 polypeptides having one or more resistance mutations described herein can be detected using antibodies that specifically recognize the mutant MEK1 or MEK2 polypeptides, but do not recognize wild-type MEK1 or MEK2 polypeptides. Antibodies can be raised against one or more allelic forms of the MEK1 or MEK2 polypeptides having one or more resistance mutations. Techniques for using a specific protein or an oligopeptide as an antigen to elicit antibodies that specifically recognize epitopes on the peptide or protein are well known. In one embodiment, the DNA sequence of the desired allelic form of the target gene can be cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. A third embodiment is to use the DNA sequence of the alternative alleles as a basis for the generation of synthetic peptides representing the amino acid sequence of the alleles for use as antigen to elicit the production of specific antibodies.

Antibodies can be generated either by standard monoclonal antibody techniques or generated through recombinant based expression systems. See generally, Abbas, Lichtman, and Pober, Cellular and Molecular Immunology, W. B. Saunders Co. (1991). The term "antibodies" is meant to include intact antibody molecules as well as antibody fragments or derivatives, such as Fab and F(ab')2, which are capable of specifically binding to antigen. The antibodies so produced will preferentially bind only the mutant protein produced in the allelic form which was used as an antigen to create the antibody. Methods of generating allele-specific antibodies are also described in U.S. Pat. No. 6,200,754 and U.S. Pat. No. 6,054,273, the entire contents of which are incorporated herein by reference.

Such antibodies specific for mutant MEK polypeptides can be used to detect the presence of a MEK polypeptide having one or more resistance mutations in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. Antibodies which specifically recognize mutant MEK polypeptides can also be second-generation MEK inhibitors. The ability of an antibody which specifically recognizes a mutant MEK polypeptide to inhibit the biological activity of the mutant MEK polypeptide can be determined using the methods described herein for identifying second-generation MEK inhibitors.

IX. Diagnostic and Screening Applications

The foregoing techniques can be used to determine the presence or absence of a previously identified resistance mutation in a MEK nucleic acid or polypeptide molecule in a sample obtained from a patient. Identification of a mutant MEK nucleic acid or polypeptide molecule in a patient sample can be useful for characterizing a disease or condition in the patient. For example, in a patient having a disease associated with aberrant expression or activation of MEK (e.g., a cancer), identification of a mutant MEK nucleic acid or polypeptide molecule in sample (e.g., a cancer-cell containing sample) obtained from the patient indicates that the patient is at a relatively high risk of relapse or lack of response to treatment with a MEK inhibitor. In one embodiment, identification of a MEK nucleic acid or polypeptide molecule containing one or more mutations described herein in a cancer-cell containing sample obtained from a patient indicates that the patient is at a relatively high risk of relapse or lack of response to treatment with a first generation MEK inhibitor, e.g., CI-1040, AZD6244, PD318088, PD98059, PD334581, RDEA119, Compound A, or Compound B.

A patient who has a MEK resistance mutation described herein has a higher risk of relapse from treatment with a first-generation MEK inhibitor than a patient in whom a MEK resistance mutation can not be detected. Accordingly, as used herein, the term "relatively high risk of relapse" is in relation to a patient in whom a mutant MEK nucleic acid or polypeptide molecule cannot be detected. That is, a patient who has a "relatively high risk of relapse" is a patient who has a greater risk of relapse as compared to a patient in whom a mutant MEK nucleic acid or polypeptide molecule cannot be detected.

In certain embodiments, identification of a MEK polypeptide, or a nucleic acid encoding a MEK polypeptide, having a mutation at one or more of the following residues indicates that the patient is at relatively high risk of relapse or lack of response to treatment with a first-generation MEK inhibitor, e.g., CI-1040: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H in MEK1; and 71D, 78L, 107I, 110A, 111I, 115I, 119L, 123H, 128P, 132G, 133F, 171G, 207E, 215V, 251W, 262V, 264R, 280G, 310M, 311D, 316M, and 336G in MEK2. In other embodiments, identification of a MEK polypeptide, or a nucleic acid encoding a MEK polypeptide, having a mutation at one or more of the following residues indicates that the patient is at relatively high risk of relapse or lack of response to treatment with a first-generation MEK inhibitor, e.g., CI-1040: 56Q, 99I, 104K, 113R, 120E, 128G, 133F, 215L, 237G, 326P and 368E in MEK1; and 60Q, 103I, 108K, 117R, 124E, 132G, 137F, 219L, 241G, 334P and 376E in MEK2. In exemplary embodiments, identification of a MEK polypeptide, or a nucleic acid encoding a MEK polypeptide, having one or more of the following resistance mutations indicates that the patient is at relatively high risk of relapse or lack of response to treatment with a MEK inhibitor, e.g., CI-1040: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D in MEK1; and 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R in MEK2. In other embodiments, identification of a MEK polypeptide, or a nucleic acid encoding a MEK polypeptide, having one or more of the following resistance mutations indicates that the patient is at relatively high risk of relapse or lack of response to treatment with a MEK inhibitor, e.g., CI-1040: 56Q>P, 99I>T, 104K>N, 113R>S, 120E>D, 128G>D, 133F>L, 215L>P, 237G>V, 326P>L, and 368E>K in MEK1; and 60Q>P, 103I>T, 108K>N, 117R>S, 124E>D, 132G>D, 137F>L, 219L>P, 241G>V, 334P>L, and 376E>K in MEK2.

Determining the presence or absence of a mutant MEK nucleic acid or polypeptide molecule in a patient sample also allows for the selection of an optimized treatment regimen for the patient, or stratification of the patient to a certain treatment group. In one embodiment, a treatment regimen comprising treatment with a first-generation MEK inhibitor is selected for a patient wherein a cancer cell-containing sample from the patient does not contain a mutant MEK nucleic acid or polypeptide molecule. Such a patient can be stratified to a treatment regimen comprising a first-generation MEK inhibitor. The MEK inhibitor can be given to such a patient at a standard dosage, at standard dosing intervals.

In another embodiment, a treatment regimen comprising a combination therapy with a MEK inhibitor and a RAF inhibitor is selected for a patient wherein a cancer cell-containing sample from the patient does not contain a mutant MEK nucleic acid or polypeptide molecule. Such a patient can be stratified to a treatment regimen comprising a first generation MEK inhibitor or a second generation MEK inhibitor, in combination with a RAF inhibitor. A treatment regimen comprising a combination therapy with a MEK inhibitor and a RAF inhibitor advantageously suppresses the emergence of MEK resistant alleles in a patient whose cancer does not contain a mutant MEK molecule.

In another embodiment, a treatment regimen comprising treatment without a MEK inhibitor is selected for a patient wherein a cancer cell-containing sample from the patient contains a mutant MEK nucleic acid or polypeptide molecule, e.g., a MEK nucleic acid or polypeptide molecule containing one or more of the mutations described herein. Such a patient can be stratified to a treatment regimen that does not comprise a MEK inhibitor.

In another embodiment, a treatment regimen comprising treatment with an elevated dosage of a first-generation MEK inhibitor is selected for a patient wherein a cancer cell-containing sample from the patient contains a mutant MEK nucleic acid or polypeptide molecule. Such a patient can be stratified to a treatment regimen comprising an elevated dosage of a first-generation MEK inhibitor. In an exemplary aspect of the foregoing embodiments, the first-generation MEK inhibitor is CI-1040, AZD6244, PD318088, PD98059, PD334581, RDEA119, Compound A, or Compound B.

In an alternative embodiment, identification of a mutant MEK nucleic acid or polypeptide molecule in a cancer-cell containing sample obtained from a patient indicates that the patient is likely to respond to treatment with a second-generation MEK inhibitor. Accordingly, in one embodiment, a treatment regimen comprising treatment with a second-generation MEK inhibitor is selected for a patient wherein a cancer cell-containing sample from the patient contains a mutant MEK nucleic acid or polypeptide molecule. Such a patient can be stratified to a treatment regimen comprising a second-generation MEK inhibitor.

In particular aspects of the foregoing embodiments, the mutant MEK polypeptide is a mutant MEK1 polypeptide that has a mutation at one or more of the following residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H. In another embodiment, the mutant MEK polypeptide is a mutant MEK1 polypeptide that has a mutation at one or more of the following residues: 56Q, 99I, 104K, 113R, 120E, 128G, 133F, 215L, 237G, 326P, and 368E. In exemplary embodiments, the mutant MEK1 polypeptide has one or more of the following mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>E, 203E>K, 211V>D, 247W>G, 258V>G, 260R>G, 276G>E, 286G>E, 302M>R, 303D>A, 308M>L, 328G>L, 328G>R, 379I>L and 399H>D. In other embodiments, the mutant MEK1 polypeptide has one or more of the following mutations: 56Q>P, 99I>T, 104K>N, 113R>S, 120E>D, 128G>D, 133F>L, 215L>P, 237G>V, 326P>L, and 368E>K. In related embodiments, the mutant MEK polypeptide is a mutant MEK2 polypeptide that has a mutation at one or more of the following residues: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In another embodiment, the mutant MEK polypeptide is a mutant MEK2 polypeptide that has a mutation at one or more of the following residues: 60Q, 103I, 108K, 117R, 124E, 132G, 137F, 219L, 241G, 334P, and 376E. In exemplary embodiments, the mutant MEK2 polypeptide has one or more of the following mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In other embodiments, the mutant MEK2 polypeptide has one or more of the following mutations: 60Q>P, 103I>T, 108K>N, 117R>S, 124E>D, 132G>D, 137F>L, 219L>P, 241G>V, 334P>L, and 376E>K. In a preferred embodiment, a mutant MEK nucleic acid molecule encodes a mutant MEK polypeptide containing a mutation at one or more of the foregoing amino acid residues.

X. Methods of Treatment

In various embodiments, the invention provides methods of treating a subject having a cancer. Said methods generally comprise administration of a MEK inhibitor, e.g., a second-generation MEK inhibitor, as described herein. In exemplary embodiments, the subject has a cancer containing a MEK polypeptide having one or more mutations, e.g., one or more of the resistance mutations described herein. In related embodiments, the subject has a cancer containing a nucleic acid molecule encoding a MEK polypeptide having one or more mutations, e.g., one or more of the resistance mutations described herein. The term "treated," "treating" or "treatment" includes the diminishment or alleviation of at least one symptom associated with the condition being treated. For example, treatment can be diminishment of one or several symptoms of a disorder or complete eradication of a disorder, such as cancer.

Because mutations in MEK broadly enhance resistance in a number of types of cancer, the methods and second-generation MEK inhibitors described herein are useful in treating a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers.

In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In some embodiments, pharmaceutical compositions of the compounds (or combinations) of the invention can be in unitary dosage form suitable for administration orally, rectally or by parenteral injection. For example, in preparing compositions in oral dosage form, any of the usual pharmaceutical media may be employed, such as, for example, water, glycols, oils, alcohols and the like, as in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are employed. For parenteral compositions, carriers usually comprise sterile water, at least in large part, though other ingredients, for example, to aid solubility, may be included. Injectable solutions, for example, are prepared using a carrier which comprises saline solution, glucose solution or a mixture of saline and glucose solution. Injectable suspensions may also be prepared in which case appropriate liquid carriers, suspending agents and the like may be employed. In case of compositions suitable for percutaneous administration, carrier optionally comprises a penetration enhancing agent and/or a suitable wetting agent, which may be combined with suitable additives of any nature in minor proportions, which additives do not cause a significant deleterious effect to the skin. Additives may facilitate the administration to the skin and/or may be helpful for preparing desired compositions. These compositions may be administered in various ways, e.g., as a transdermal patch, as a spot-on, as an ointment.

It is especially advantageous to formulate the pharmaceutical compositions described herein in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In general it is contemplated that a therapeutically effective amount of a first or a second compound would be from about 0.0001 mg/kg to 0.001 mg/kg; 0.001 mg/kg to about 10 mg/kg body weight or from about 0.02 mg/kg to about 5 mg/kg body weight. In some embodiments, a therapeutically effective amount of a first or a second compound is from about 0.007 mg to about 0.07 mg, about 0.07 mg to about 700 mg, or from about 1.4 mg to about 350 mg. A method of prophylactic or curative treatment may also include administering the composition in a regimen of between one to five intakes per day.

In some embodiments, a therapeutically effective amount of a first compound or a second compound includes, but is not limited to, the amount less than about 0.01 mg/dose, or less than about 0.5 mg/dose, or less than about 1 mg/dose, or less than about 2 mg/dose, or less than about 5 mg/dose, or less than about 10 mg/dose, or less than about 20 mg/dose, or less than about 25 mg/dose, or less than about 50 mg/dose, or less than about 100 mg/dose. The number of times a day a first or a second compound is administrated to a subject can be determined based on various criteria commonly used in the art and/or those described herein.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the composition that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a composition of the present invention with the carrier and, optionally, one or more accessory ingredients. In general, the formulations are prepared by uniformly and intimately bringing into association a composition of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a composition of the present invention as an active ingredient. A composition of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compositions of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compositions of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active composition.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a composition of this invention include powders, sprays, ointments, pastes, creams, lotions, gels, solutions, patches and inhalants. The active composition may be mixed under sterile conditions with a pharmaceutically acceptable carrier, and with any preservatives, buffers, or propellants that may be required.

The ointments, pastes, creams and gels may contain, in addition to an active composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a composition of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a composition of the present invention to the body. Such dosage forms can be made by dissolving or dispersing the composition in the proper medium. Absorption enhancers can also be used to increase the flux of the composition across the skin. The rate of such flux can be controlled by either providing a rate controlling membrane or dispersing the active composition in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compositions of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compositions in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a viral infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

XI. Methods of Treatment Using a Combination Therapy

The present invention further describes methods of suppressing the emergence of MEK resistance mutations in a subject having cancer. Such methods involve the combined administration of a MEK inhibitor (e.g., a first generation MEK inhibitor or a second generation MEK inhibitor) and a RAF inhibitor. Accordingly, the present invention provides a combination therapy for treating or preventing the symptoms of a cancer, comprising administration of a MEK inhibitor and a RAF inhibitor. The term "combination therapy", as used herein, refers to the administration of two or more therapeutic substances, e.g., a MEK inhibitor or a RAF inhibitor. The MEK inhibitor may be administered concomitant with, prior to, or following the administration of a RAF inhibitor. As set forth herein, a combination therapy involving a MEK inhibitor and a RAF inhibitor suppresses the emergence of MEK resistance mutations to a greater extent than administration of either a MEK inhibitor or a RAF inhibitor alone. Standard dosages of the MEK and RAF inhibitors are also suitable for the combination therapies described herein. Exemplary cancers that can be treated with a combination therapy include those described herein, for example, leukemias, lymphomas, myelomas, carcinomas, metastatic carcinomas, sarcomas, adenomas, nervous system cancers and geritourinary cancers, e.g., melanoma, myelodysplastic syndrome, leukemia, pancreatic cancer, ovarian cancer, peritoneal cancer, non small cell lung cancer, and breast cancer.

Exemplary MEK inhibitors include first-generation and second generation MEK inhibitors. In particular embodiments, MEK inhibitors useful for combination therapy include CI-1040, AZD6244, PD318088, PD98059, PD334581, RDEA119, Compound A, and Compound B. Exemplary RAF inhibitors useful for combination therapy include pan-RAF inhibitors, inhibitors of B-RAF, inhibitors of A-RAF, and inhibitors of RAF-1. In exemplary embodiments RAF inhibitors useful for combination therapy include PLX4720, PLX4032, BAY 43-9006 (Sorafenib), ZM 336372, RAF 265, AAL-881, LBT-613, and CJS352. Exemplary RAF inhibitors further include the compounds set forth in PCT Publication No. WO/2008/028141, the entire contents of which are incorporated herein by reference. Exemplary RAF inhibitors additionally include the quinazolinone derivatives described in PCT Publication No. WO/2006/024836, and the pyridinylquinazolinamine derivatives described in PCT Publication No. WO/2008/020203, the entire contents of which are incorporated herein by reference.

Accordingly, the invention provides methods of treating cancer in a subject, comprising administering a combination therapy comprising a MEK inhibitor and a RAF inhibitor, as described herein. In some embodiments, the method further comprises screening a subject to detect the presence or absence of one or more mutations in MEK. In a preferred embodiment, a combination therapy comprising a MEK inhibitor and a RAF inhibitor is selected for a subject in whom one or more mutations in MEK are not detected. In such a subject, the combination therapy advantageously suppresses the emergence of MEK resistance mutations. The invention further provides methods of suppressing the emergence of MEK resistance mutations in a subject having cancer, comprising administering to the subject a combination therapy comprising a MEK inhibitor and a RAF inhibitor, as described herein. Accordingly, a combination therapy comprising a MEK inhibitor and a RAF inhibitor may be administered to a subject in whom one or more MEK resistance mutations are detected. Such a combination therapy suppresses the growth of cells containing MEK resistance mutations. In some embodiments, the method further comprises screening a subject to detect the presence or absence of one or more mutations in MEK. In these embodiments, a combination therapy comprising a MEK inhibitor and a RAF inhibitor can be given, for example, to a subject in whom a MEK resistance mutation was not detected, or, for example, to a subject in whom a MEK resistance mutation was detected.

In another embodiment of the invention, a pharmaceutical composition can comprise (a) a MEK inhibitor and also (b) a RAF inhibitor. In some embodiments, the MEK inhibitor can be a first generation MEK inhibitor or a second generation MEK inhibitor. In some embodiments, the RAF inhibitor can be a pan-RAF inhibitor, an inhibitor of B-RAF, an inhibitor of A-RAF, and an inhibitor of RAF-1. In exemplary embodiments, the MEK inhibitor can be CI-1040, AZD6244, PD318088, PD98059, PD334581, RDEA119, Compound A, or Compound B, and the RAF inhibitor can be PLX4720, PLX4032, BAY 43-9006 (Sorafenib), ZM 336372, RAF 265, AAL-881, LBT-613, and CJS352. In a particular embodiment, the pharmaceutical composition comprises (a) AZD6244 and also (b) PLX4720.

Another embodiment of the invention is directed to methods of administering the pharmaceutical compositions described herein. Hence, the present invention is directed to a method of treating a subject for cancer comprising administering to the subject a MEK inhibitor; and administering to the subject a pharmaceutical composition comprising a RAF inhibitor. The MEK inhibitor and the RAF inhibitor can be administered to the subject sequentially or simultaneously. A sequential administration includes (a) first administering the MEK inhibitor followed by (b) administering the RAF inhibitor. An alternative sequential administration includes (a) first administering the RAF inhibitor followed by (b) administering the MEK inhibitor. A simultaneous administration includes administering the MEK inhibitor and the RAF inhibitor at the same time; or at substantially the same time.

When administration involves the separate administration (e.g., sequential administration) of the first compound (e.g., a MEK inhibitor) and a second compound (e.g., a RAF inhibitor), as described herein, the compounds are administered sufficiently close in time to have the desired therapeutic effect. For example, the period of time between each administration, which can result in the desired therapeutic effect, can range from minutes to hours and can be determined based on the properties of each compound such as potency, solubility, bioavailability, plasma half-life and kinetic profile. For example, the compounds can be administered in any order within about 24 hours of each other or within any time less than 24 hours of each other.

When the MEK inhibitor and the RAF inhibitor are administered sequentially, they are separately formulated and can be provided in any order. When the MEK inhibitor and the RAF inhibitor are administered simultaneously, however, they may be either separately formulated or combined in the same formulation. When combined in the same formulation, the MEK inhibitor and the RAF inhibitor can be formulated so as to be released into the subject at the same time or at different times. The release profile of a formulation comprising both the MEK inhibitor and the RAF inhibitor includes the following:

A) release and bioavailability of the MEK inhibitor followed by release and bioavailability of the RAF inhibitor;

B) release and bioavailability of the RAF inhibitor followed by release and bioavailability of the MEK inhibitor;

C) release and bioavailability of the MEK inhibitor at the same time (or substantially at the same time as) release and bioavailability of the RAF inhibitor.

In another embodiment, provided herein is a method of treating cancer in a subject in need thereof comprising administering to the subject a composition comprising a MEK inhibitor and a RAF inhibitor. In still another embodiment, provided herein is a method of treating cancer in a subject in need thereof comprising administering to the subject a composition comprising a MEK inhibitor and a RAF inhibitor, wherein the cancer is selected from the group consisting of leukemias, lymphomas, myelomas, carcinomas, metastatic carcinomas, sarcomas, adenomas, nervous system cancers and geritourinary cancers, e.g., melanoma, myelodysplastic syndrome, leukemia, pancreatic cancer, ovarian cancer, peritoneal cancer, non small cell lung cancer, and breast cancer.

A combination of compounds described herein (e.g., a MEK inhibitor and a RAF inhibitor) can either result in synergistic increase in anti-cancer activity, or such an increase can be additive. Compositions described herein typically include lower dosages of each compound in a composition, thereby avoiding adverse interactions between compounds and/or harmful side effects, such as ones which have been reported for similar compounds. Furthermore, normal amounts of each compound when given in combination could provide for greater efficacy in subjects who are either unresponsive or minimally responsive to each compound when used alone. For example, when given in combination, a MEK inhibitor and a RAF inhibitor suppress the emergence of MEK resistance alleles to a greater extent than when either compound is used alone.

A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, the invention provides a pharmaceutical composition of any of the compositions of the present invention. In a related embodiment, the invention provides a pharmaceutical composition of any of the compositions of the present invention and a pharmaceutically acceptable carrier or excipient of any of these compositions.

In one embodiment, the invention includes a packaged cancer treatment. The packaged treatment includes a composition of the invention packaged with instructions for using an effective amount of the composition of the invention for an intended use. In other embodiments, the present invention provides a use of any of the compositions of the invention for manufacture of a medicament to treat a cancer in a subject.

In another embodiment of the invention, the MEK inhibitor and the RAF inhibitor can be administered sequentially (in any order) or simultaneously with other pharmaceutical agents typically administered to subjects being treated for cancer. Such other pharmaceutical agents include without limitation anti-emetics, agents that increase appetite, other cytotoxic or chemotherapeutic agents, and agents that relieve pain. The CDA substrate and the compound of any one of formulae I-VIII can be formulated together with or separately from such other pharmaceutical agents.

XII. Kits

Various kits may be assembled as part of the present invention. A kit can contain components to assay for mutations in MEK to evaluate a particular patient for the risk of developing resistance to therapy using a MEK inhibitor, and thus allow a clinician to determine whether an alternative treatment for the patient is needed. Such kits can contain reagents that allow for mutations to be evaluated, such as primer sets to evaluate mutations correlated with relevant phenotypic manifestations concerning resistance to a MEK inhibitor (e.g., CI-1040). It is contemplated that primers (or pairs of primers) that are complementary to or identical to all or part of SEQ ID NO:1 or SEQ ID NO:3, for example, can be part of a kit. In preferred embodiments, the primers can be used to specifically detect or amplify a nucleic acid molecule encoding a mutant MEK1 polypeptide containing a mutation at one or more of the following amino acid residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H, or a mutant MEK2 polypeptide containing a mutation at one or more of the following residues: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. In other embodiments, the primers can be used to specifically detect or amplify a nucleic acid molecule encoding a mutant MEK1 polypeptide containing a mutation at one or more of the following amino acid residues: 56Q, 99I, 104K, 113R, 120E, 128G, 133F, 215L, 237G, 326P, and 368E, or a mutant MEK2 polypeptide containing a mutation at one or more of the following residues: 60Q, 103I, 108K, 117R, 124E, 132G, 137F, 219L, 241G, 334P, and 376E. In exemplary embodiments, the primers specifically detect or amplify a nucleic acid molecule encoding a MEK1 polypeptide containing one or more of the following mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D, or a MEK2 polypeptide containing one or more of the following mutations: 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R. In other embodiments, the primers specifically detect or amplify a nucleic acid molecule encoding a MEK1 polypeptide containing one or more of the following mutations: 56Q>P, 99I>T, 104K>N, 113R>S, 120E>D, 128G>D, 133F>L, 215L>P, 237G>V, 326P>L, and 368E>K, or a MEK2 polypeptide containing one or more of the following mutations: 60Q>P, 103I>T, 108K>N, 117R>S, 124E>D, 132G>D, 137F>L, 219L>P, 241G>V, 334P>L, and 376E>K. In other embodiments, the kits contain instructions for using primers that are complementary or identical to all or part of SEQ ID NO:1 or SEQ ID NO:3 to amplify a nucleotide sequence encoding a MEK polypeptide.

In other embodiments, the kits comprise compositions for detecting a mutation comprising a MEK polypeptide, such as an antibody which specifically recognizes a mutant MEK polypeptide containing one or more resistance mutations. Exemplary polypeptides include a mutant MEK1 polypeptide containing a mutation at one or more of the following amino acid residues: 67D, 74L, 103I, 106A, 107I, 111I, 115L, 119H, 124P, 128G, 129F, 167G, 203E, 211V, 247W, 258V, 260R, 276G, 286G, 302M, 303D, 308M, 328G and 399H, or a mutant MEK2 polypeptide containing a mutation at one or more of the following amino acid residues: 71D, 78L, 107I, 110A, 111I, 115I, 119L, 123H, 128P, 132G, 133F, 171G, 207E, 215V, 251W, 262V, 264R, 280G, 310M, 311D, 316M, and 336G. Other exemplary polypeptides include a mutant MEK1 polypeptide containing a mutation at one or more of the following amino acid residues: 56Q, 99I, 104K, 113R, 120E, 128G, 133F, 215L, 237G, 326P, and 368E, or a mutant MEK2 polypeptide containing a mutation at one or more of the following amino acid residues: 60Q, 103I, 108K, 117R, 124E, 132G, 137F, 219L, 241G, 334P, and 376E. In other embodiments, the mutant MEK polypeptide contains one or more of the following mutations: 67D>N, 74L>Q, 74L>R, 103I>N, 106A>T, 107I>M, 111I>N, 115L>R, 115L>P, 119H>P, 124P>L, 124P>S, 128G>D, 129F>L, 167G>R, 203E>K, 211V>D, 247W>G, 258V>G, 260R>G, 276G>E, 286G>E, 302M>R, 303D>A, 308M>L, 328G>L, 328G>R, 379I>L and 399H>D in MEK1; and 71D>N, 78L>Q, 78L>R, 107I>N, 110A>T, 111I>M, 115I>N, 119L>R, 119L>P, 123H>P, 128P>L, 128P>S, 132G>D, 133F>L, 171G>R, 207E>K, 215V>D, 251W>G, 262V>G, 264R>G, 280G>E, 310M>R, 311D>A, 316M>L, 336G>L, and 336G>R in MEK2. In other embodiments, the mutant MEK polypeptide contains one or more of the following mutations: 56Q>P, 99I>T, 104K>N, 113R>S, 120E>D, 128G>D, 133F>L, 215L>P, 237G>V, 326P>L, and 368E>K in MEK1; and 60Q>P, 103I>T, 108K>N, 117R>S, 124E>D, 132G>D, 137F>L, 219L>P, 241G>V, 334P>L, and 376E>K in MEK2.

All of the essential materials and reagents required for assaying for MEK mutations by a particular method discussed above can also be assembled together in a kit. When the components of the kit are provided in one or more liquid solutions, the liquid solution preferably is an aqueous solution, with a sterile aqueous solution being particularly preferred.

The invention further provides kits comprising compositions, (e.g., pharmaceutical compositions), comprising a second generation MEK inhibitor. Such kits can be used in the methods set forth herein, for example, for treating a cancer in a subject. Accordingly, the kits may further contain instructions that describe the use of the composition for the treatment of cancer.

The invention likewise provides kits comprising compositions suitable for use in a combination therapy involving a MEK inhibitor and a RAF inhibitor. Such kits may include, for example, a composition comprising a MEK inhibitor and a composition comprising a RAF inhibitor. Such kits may alternatively include a composition comprising both a MEK inhibitor and a RAF inhibitor. The kits may further contain instructions that describe the use of the composition for the treatment of cancer, and/or for suppressing the emergence of MEK resistance alleles in a subject having cancer. The instructions may describe the administration of a composition comprising a MEK inhibitor simultaneously, prior to, or following administration of a RAF inhibitor.

The components of the kit can also be provided in dried or lyophilized forms. When reagents or components are provided as a dried form, reconstitution generally is by the addition of a suitable solvent. It is envisioned that the solvent also can be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also can comprise, or be packaged with, an instrument for assisting with sample collection and evaluation. Such an instrument can be an inhalant, syringe, pipette, forceps, measured spoon, eye dropper or any such medically approved delivery vehicle, for example.

The kits of the invention can also include an instruction sheet outlining suggested alternative therapies when particular mutations are identified in a patient. For example, an instruction sheet included with the kits of the invention can recommend that a patient having a disorder, e.g., a cancer, in which a mutant MEK polypeptide has been identified, discontinue treatment with a first-generation MEK inhibitor, be monitored for relapse during treatment with a first-generation MEK inhibitor, continue treatment with a first-generation MEK inhibitor at an elevated dosage, or initiate treatment with a second-generation MEK inhibitor. An instruction sheet included with the kits of the invention can likewise recommend that a patient having a disorder in which a mutant MEK polypeptide is not detectable continue treatment with a first-generation MEK inhibitor at a standard dosage. In exemplary embodiments, the first-generation MEK inhibitor is CI-1040, AZD6244, PD318088, PD98059, PD334581, RDEA119, Compound A, or Compound B.

This invention is further illustrated by the following examples, which should not be construed as limiting. The contents of all references, patents and published patent applications cited throughout this application are incorporated herein by reference.

EXAMPLES

Example 1

Identification of MEK Mutations that Confer Resistance to First-Generation MEK Inhibitors To investigate the importance of RAF/MEK dependency and "on-target" resistance to MEK inhibition in melanoma, random mutagenesis screens together with massively-parallel sequencing were employed to discover the spectrum of variants associated with resistance to MEK inhibition (outlined in FIG. 1). Here, a saturating cDNA library of MEK1 mutations was introduced into A375 melanoma cells, which harbor the $BRAF^{V600E}$ mutation and are highly sensitive to MEK inhibition. After culturing these cells for 4 weeks in the presence of a diaryl amine MEK inhibitor (e.g., AZD6244 or CI-1040) resistant clones emerged, ~1000 of which were pooled and characterized en masse by massively-parallel sequencing. An additional 100 clones were sequenced by the Sanger method. This combined analysis of ~1100 resistant clones vastly exceeded the scope of prior mutagenesis studies and offered a comprehensive framework for unbiased characterization of MEK/-mediated drug resistance.

Figure 2A:
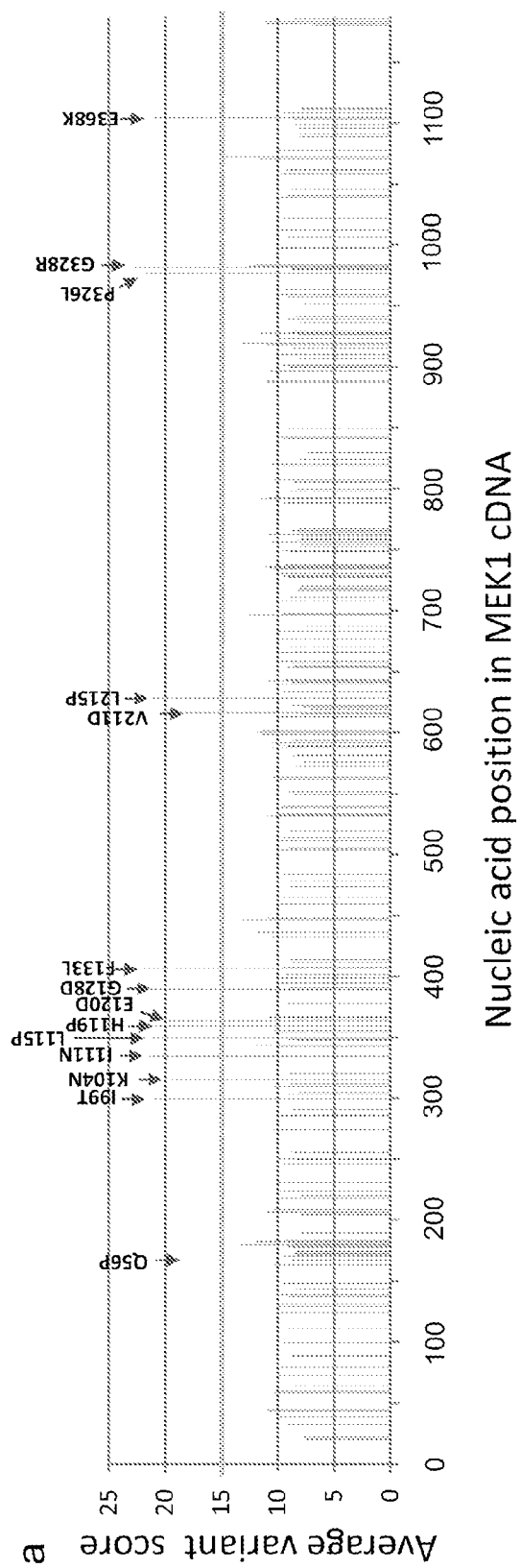
FIGS. 2a-2c depict MEK1 resistance mutations identified in a mutagenesis screen. (A): The average variant score (based on a lane of Illumina sequencing) of candidate mutations across the MEK1 coding sequence from the AZD6244 mutagenesis screen is shown. The corresponding amino acid substitutions from high scoring mutations (>15%) are indicated in bold. (B): The locations of putative MEK1 inhibitor resistance alleles are indicated within the crystal structure of MEK1 (red). Both ATP and an aryl amine MEK inhibitor (PD318088) are shown to bind MEK1; this inhibitor chemotype binds a hydrophobic pocket adjacent to the ATP binding site. Candidate resistance alleles cluster within Helix C, the hydrophobic drug binding pocket, and the activation loop. (C): The majority of high-frequency mutations cluster in two distinct regions encoded by exons 3 and 6 of MEK1. The locations of the C helix and activation loop are indicated.
Figure 2B:
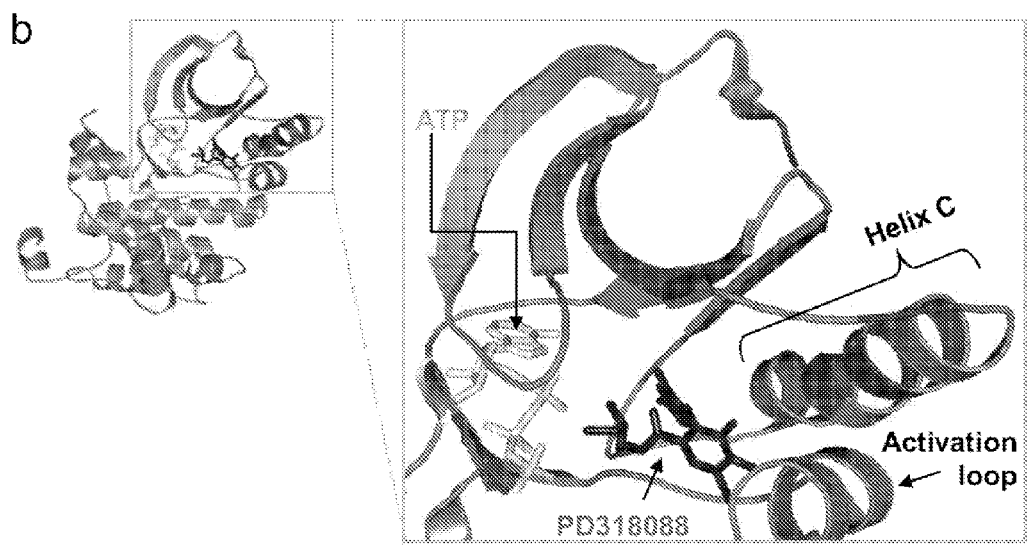
Figure 2C:
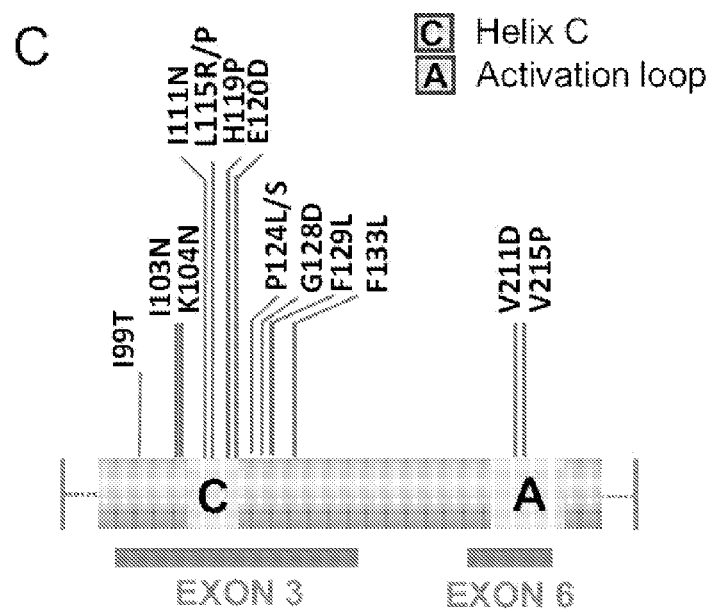
Figure 3:
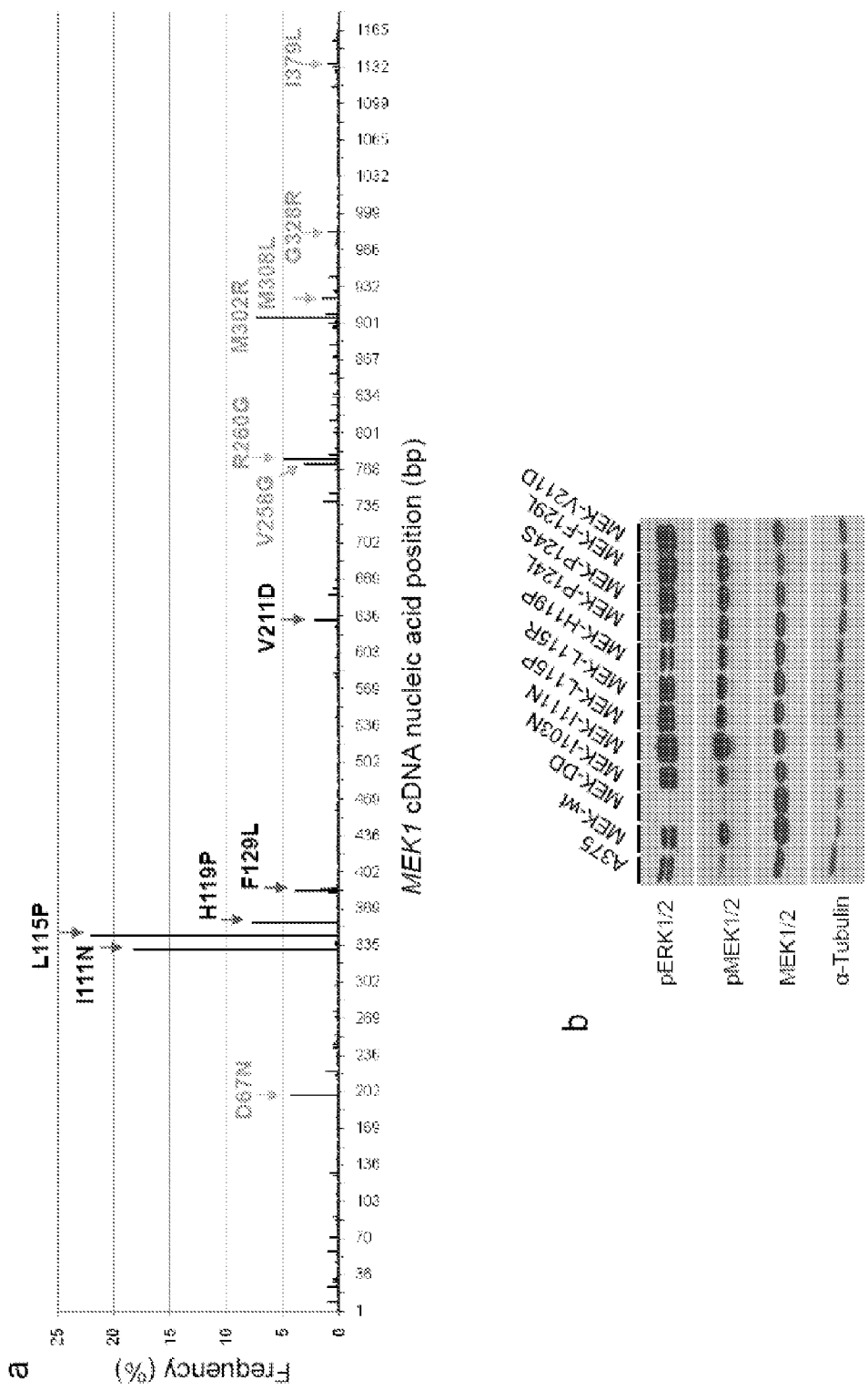
FIG. 3 shows the frequency of mutations across the MEK coding sequence from a mutagenesis screen using the first-generation MEK inhibitor CI-1040. The corresponding amino acids are shown for high frequency alleles (Panel A). Panel B shows the relative levels of pERK1/2, pMEK1/2, MEK1/2 and α-Tubulin in A375 cells expressing resistant MEK1 alleles.

The distribution of candidate resistance alleles across each MEK1 nucleotide position, and the resulting amino acid substitutions within the MEK three-dimensional structure, were then investigated. Nearly all non-synonymous nucleotide mutations clustered within exons 3 and 6 of MEK (FIG. 2a), which encode "C helix" and flanking hydrophobic residues, plus the majority of the kinase activation loop. Notably, these alleles corresponded closely to the known binding pocket of diaryl amine-based MEK inhibitors, which engage a novel allosteric site adjacent to the ATP binding motif (FIG. 2b). Furthermore, several high-frequency MEK amino acid substitutions converted a hydrophobic residue to a charged residue or introduced a proline into the proximal aspect of the C helix (FIG. 2c). Such alterations may disrupt drug binding either through steric hindrance or altered C helical conformation. A few mutations localized elsewhere within MEK1, but preliminary functional studies suggested that these were less likely to exert a prominent resistance phenotype. The foregoing data indicate that MEK1 exons 3 and 6 represent promising candidate loci for the clinical emergence of resistance to MEK inhibition. FIG. 3a depicts the frequency of mutations across the MEK1 coding sequence. Corresponding amino acids are shown for high frequency alleles. FIG. 3b depicts the relative levels of pERK1/2, pMEK1/2 and α-tubulin in A375 cells expressing resistant MEK1 alleles.

Example 2

Acquired MEK1 Mutations in AZD6244-Resistant Metastatic Melanoma

Figure 4:
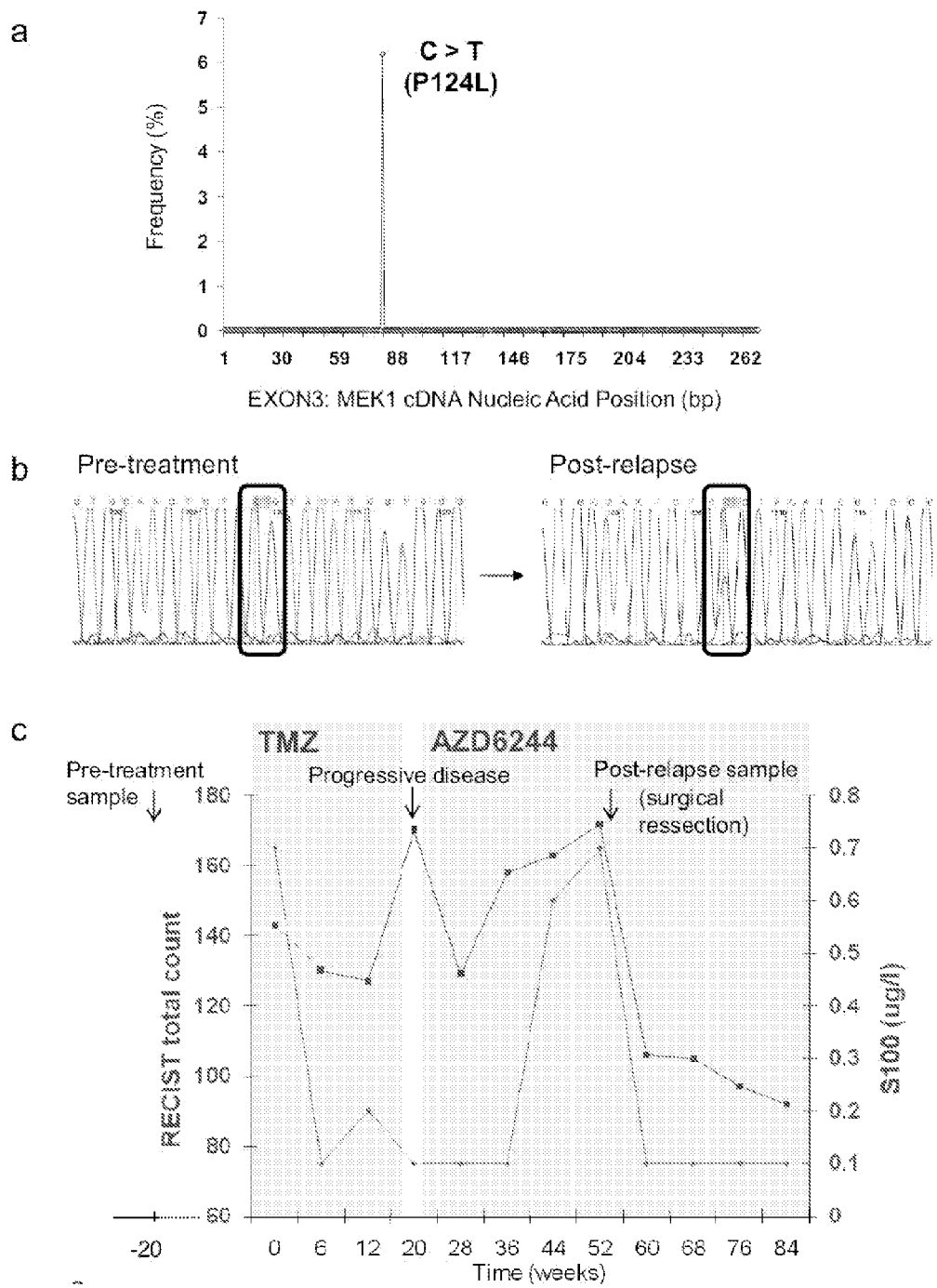
FIGS. 4a-4c depict the identification of an acquired MEK1 mutation in AZD6244-resistant metastatic melanoma. PCR products corresponding to MEK1 exons 3 and 6 were generated from relapsed melanomas treated with AZD6244; products were pooled and interrogated by massively-parallel sequencing (a single Illumina lane). (A): A single mutation, $MEK^{P/24-L}$, was recovered by this analysis. (B): Sanger sequencing chromatograms from MEK1 exon 3 corresponding to pre-treatment and post-relapse melanoma DNA from patient #7. A C>T transition, indicative of $MEK^{P124L}$, is evident only in the relapsed sample. (C): Changes in RECIST total count (blue graph) and serum S100 levels (red graph) over the clinical course of patient #7. The times of pre-treatment and post-relapse biopsies are indicated. The intervals of temozolomide treatment and AZD6244 treatment are shown.

To test the hypothesis that MEK exons 3 and 6 are likely candidates for emergence of resistance to MEK inhibition, the MEK1 locus in melanoma genomic DNA from patients enrolled in a phase II clinical trial of the MEK inhibitor AZD6244[5] was studied. Table 1 summarizes pertinent clinical characteristics of patients examined. In this trial, AZD6244 treatment did not improve clinical outcomes when compared to temozolomide; however, we identified seven patients who experienced transient disease stabilization followed by relapse on AZD6244 (mean stable disease duration=55+/−18 days in patients 1-6). Five of these patients contained dermal metastases amenable to both pre-treatment and post-relapse biopsy, and three harbored BRAF$^{V600E}$ resection, the patient continued on AZD6244 and showed prolonged disease stabilization (>44 weeks), including a steadily declining RECIST score and a 28% overall reduction in tumor burden (FIG. 4c).

Figure 5:
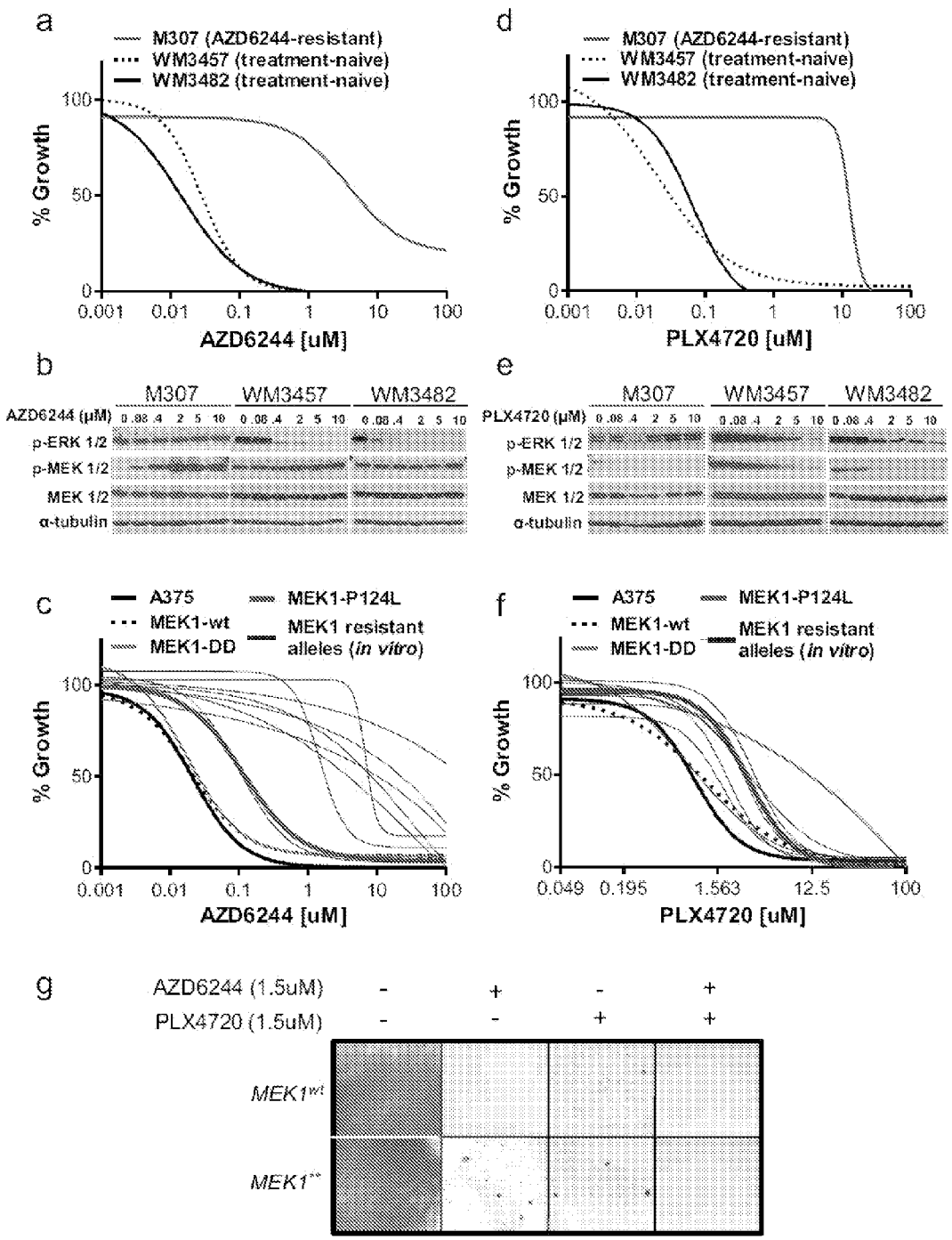
FIG. 5 depicts the functional characterization of MEK1 resistance mutations. (A): AZD6244-mediated growth inhibition ex vivo of treatment-naïve BRAFV600E melanoma cells (black) or cells cultured from an AZD6244-resistant metastatic focus (red). (B): ERK phosphorylation (p-ERK) is shown following treatment with increasing concentrations of AZD6244 in treatment-naïve or AZD6244-resistant melanoma cells cultured ex vivo. Phosphorylated and total MEK (p-MEK1/2 and MEK1/2) are also shown, together with the tubulin loading control (α-tubulin). (C): Growth inhibition curves are shown for A375 cells expressing MEK1 resistance mutations derived from in vitro screens (blue), the AZD6244-resistant metastasis ($MEK^{P124L}$; red), a constitutive active MEK variant (MEK-DD; green), wild-type MEK1 (hatched black) and parental A375 (solid black). (D): PLX4720 growth inhibition curves are shown for the cultured melanoma cells from panel A, above. (E): Immunoblot studies of p-ERK, p-MEK1/2 and MEK1/2 levels following treatment with increasing concentrations of PLX4720 in treatment-naïve or AZD6244-resistant melanoma cells. (F): PLX4720 growth inhibition curves of A375 cells expressing MEK1 resistance mutations or controls as outlined in panel C, above. (G): Colony formation of parental A375 cells or cells expressing a mutagenized MEK1 cDNA library. Cells were treated with vehicle, AZD6244 alone (1.5 µM), PLX4720 alone (1.5 µM), or AZD6244+PLX4720 (1.5 µM each).

To confirm the functional effects of MEK1$^{P124L}$ and the putative MEK1 resistance alleles identified by random mutagenesis, biochemical and pharmacologic studies were performed on several representative variants. First, ex vivo melanoma cultures were derived from the AZD6244-resistant metastasis of patient #7 (M307), and the effects of MEK inhibition in these cells was examined. The GI$_{50}$ for AZD6244 was 10-50 nM in treatment-naïve BRAF$^{V600E}$ melanoma cultures (WM3482 and WM3457; Table 3) but exceeded 2 µM in cells derived from the AZD6244-resistant metastasis (M307; FIG. 5a). Likewise, marked biochemical inhibition of ERK phosphorylation (p-ERK) was achieved following 16-hour exposure to ~400 nM AZD6244 in treatment-naïve lines, but p-ERK remained robust in the resistant cells even at 10 µM AZD6244 (FIG. 5b). Similar results were observed in studies of the related MEK inhibitor CI-1040 (Table 3).

TABLE 1

Patient Characteristics

| Patient # | Age (years) | Gender | Breslow (mm) | Staging at trial entry | Pre-treatment biopsy location | Post-treatment biopsy location | Durations of stable disease (days) | BRAF status |
|---|---|---|---|---|---|---|---|---|
| 1 | 48 | Female | 6 | T4b Nx Mx | Back, left | Skin, thoracal, left | 77 | V600E |
| 2 | 66 | Male | 3.1 | T3b N3 M1c | Skin, axillary, thoracal | Skin, shoulder, left | 48 | wt |
| 3 | 72 | Female | 5.5 | T4b N2b M1b | Lung, upper lobe | n/a | 40 | — |
| 4 | 48 | Female | 0.3 | T1a N1b M1c | Axillary lymph node, left | Skin, retro-auricular, right | 39 | V600E |
| 5 | 63 | Male | unknown | Tx Nx M1c | Skin, axillary, left | n/a | 78 | wt |
| 6 | 49 | Female | 0.8 | T1a N3 M1c | n/a | Skin, neck, left | 51 | wt |
| 7 | 58 | Male | 7 | T4 N1 M0 | Axillary lymph node, left | Axillary lymph node, left | Ongoing | V600E | melanomas. One patient (patient 7) with BRAF$^{V600E}$ melanoma experienced prolonged disease stabilization on AZD6244.

To investigate the clinical relevance of on-target resistance to MEK inhibitors, MEK1 exons 3 and 6 were PCR-amplified in tumor DNA from relapsed patients. PCR products from all patients were pooled and subjected to massively parallel sequencing. This analysis identified a C>T transition in MEK1 exon 3 that encodes a P124L substitution (FIG. 4a). MEK1 codon 124 was also implicated by Sanger sequencing in random mutagenesis screens using the MEK inhibitor CI-1040, although an alternative amino acid was selected (P124S; Table 2). Sequencing of individual pre-treatment and post-relapse melanoma samples revealed that MEK1$^{P124L}$ occurred in the post-relapse tumor DNA from patient #7, but this mutation was absent in the corresponding pre-treatment tumor sample (FIG. 4b).

The MEK1$^{P124L}$ allele was identified in a 55 year old male with metastatic melanoma, including pulmonary and skeletal involvement at the time of clinical trial enrollment. The patient was treated with oral temozolomide but developed progressive disease characterized by mediastinal lymph node enlargement and pulmonary infiltration (FIG. 4c). Switching to the AZD6244 treatment arm resulted in regression or stabilization of all disease sites except for a left axillary lymph note metastasis, which expanded over 16 weeks with a concomitant rise in the S100 tumor marker. Surgical removal of this metastasis led to a marked decrease in S100 levels; MEK1P124L was detected in this specimen. Following

TABLE 2

Summary of inhibitor-resistant MEK1 alleles

| MEK1 allele | Method of identification | Experimental Validation |
|---|---|---|
| Q56P | Massively-parallel | Not done |
| D67N | Massively-parallel and Sanger | Failed |
| L74R | Massively-parallel and Sanger | Failed |
| I99T | Massively-parallel | Not done |
| I103N | Sanger | Validated |
| K104N | Massively-parallel | Not done |
| A106T | Sanger | Failed |
| I107M | Massively-parallel | Failed |
| I111N | Massively-parallel and Sanger | Validated |
| L115P | Massively-parallel | Validated |
| L115R | Sanger | Validated |
| H119P | Massively-parallel | Validated |
| E120D | Massively-parallel | Not done |
| P124S | Sanger | Validated |
| G128D | Massively-parallel | Not done |
| F129L | Massively-parallel and Sanger | Validated |
| F133L | Massively-parallel | Not done |
| G167R | Massively-parallel and Sanger | Failed |
| V211D | Massively-parallel and Sanger | Validated |
| L215P | Massively-parallel | Not done |
| W247G | Massively-parallel and Sanger | Failed |
| V258G | Massively-parallel | Not done |
| R260G | Massively-parallel | Failed |
| M302R | Massively-parallel | Not done |
| D303A | Massively-parallel | Failed |
| M308L | Massively-parallel | Failed |
| P326L | Massively-parallel | Not done |
| G328R | Massively-parallel | Failed |

TABLE 2-continued

Summary of inhibitor-resistant MEK1 alleles

| MEK1 allele | Method of identification | Experimental Validation |
|---|---|---|
| E368K | Massively-parallel | Failed |
| I379L | Massively-parallel | Failed |

TABLE 3

GI$_{50}$ values for cell lines and MEK1 alleles

| Cell culture | AZD6244 (μM) | PLX4720 (μM) | CI-1040 (μM) |
|---|---|---|---|
| A375 | 0.04 | 0.91 | 0.07 |
| A375-MEK-wt | 0.04* | 1.29* | 0.11** |
| A375-MEK-DD | 0.05* | 16.80* | 0.11* |
| A375-MEK-I103N | 1.89** | 2.94*** | 6.14*** |
| A375-MEK-I111N | 5.96*** | 2.94*** | 7.59*** |
| A375-MEK-L115P | 55.05** | 1.97*** | 11.34*** |
| A375-MEK-L115R | 43.65*** | 1.17*** | 6.80** |
| A375-MEK-H119P | 9.08*** | 1.42*** | 6.91** |
| A375-MEK-P124S | 0.17*** | 3.44*** | 0.62*** |
| A375-MEK-P124L | 0.19** | 2.84*** | 0.56*** |
| A375-MEK-F129L | 7.32*** | 2.79*** | 6.05** |
| A375-MEK-V211D | 113.90** | 2.73** | 8.47*** |
| M307 | 7.18*** | 20.28*** | — |
| WM3457 | 0.05 | 0.07 | — |
| WM3482 | 0.01 | 0.05 | — |

Example 3

Pharmacological and Biochemical Characterization of Mutant MEK Alleles

Figure 6:
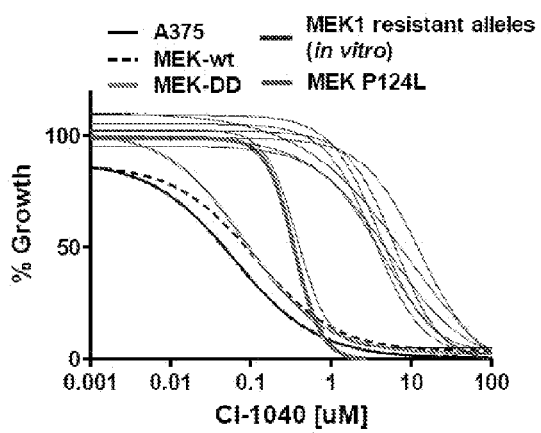
FIGS. 6a-6c depict growth inhibition curves and alterations in signaling in A375 cells containing resistance mutations. (A) shows growth inhibition curves with CI-1040 for A375 cells expressing MEK1 resistance mutations derived from in vitro screens (blue), the AZD6244-resistant metastasis ($MEK^{P124L}$; red), a constitutive active MEK variant (MEK-DD; green), wild-type MEK1 (hatched black) and parental A375 (solid black). (B) shows the levels of pERK1/2, pMEK1/2, MEK1/2 and α-Tubulin in A375 cells expressing resistant MEK1 alleles following a 16 hour incubation with CI-1040 at 10 µM, 5 µM, 2 µM, 0.4 µM, 0.08 µM and 0 µM. (C) shows protein levels following treatment with ADZ6244 in A375 cells compared to A375 expressing MEK1 wild type ($MEK1^{WT}$), constitutive activated MEK1 ($MEK^{DD}$) and $MEK^{P124L}$.
Figure 6:
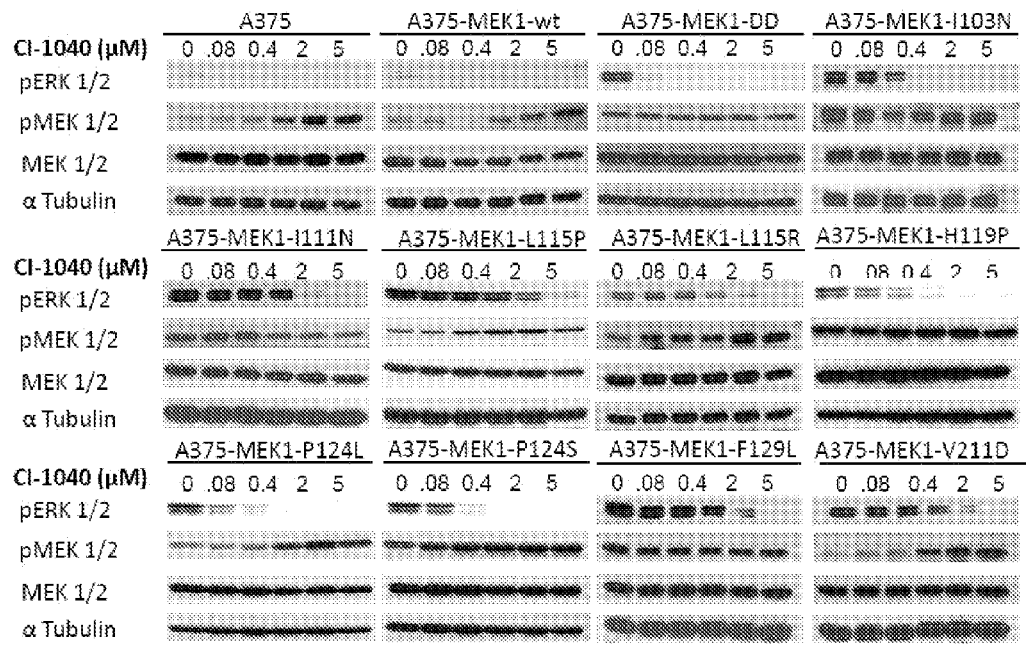
Figure 6:
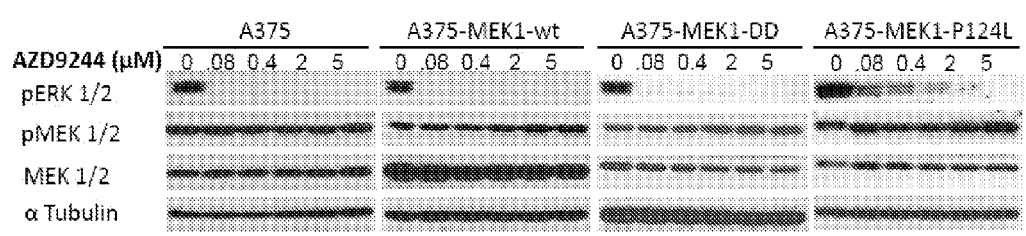

Next, we introduced P124L and several additional candidate resistance alleles into the sequence of wild-type MEK1 and expressed these variants in A375 melanoma cells. All variant constructs were overexpressed at comparable levels. A375 cells expressing wild-type MEK1 or a constitutively active control (MEK-DD) showed AZD6244 GI50 values comparable to wild-type A375 (~50 nM; FIG. 5c). In contrast, P124L and P124S alleles increased the GI50 of AZD6244 and CI-1040 by 5-10-fold; several additional alleles located in the MEK1 C helix (I103N, I111N, L115P/R, H119P), drug binding pocket (F129L) or activation loop (V211D) increased the GI$_{50}$ by ~100-fold (FIG. 5c). Biochemical analyses of both drugs corroborated these findings (FIG. 6). These results validated the functional relevance of resistance-associated MEK1 alleles.

Example 4

MEK Mutations Confer Cross-Resistance to RAF Inhibition

Figure 7:
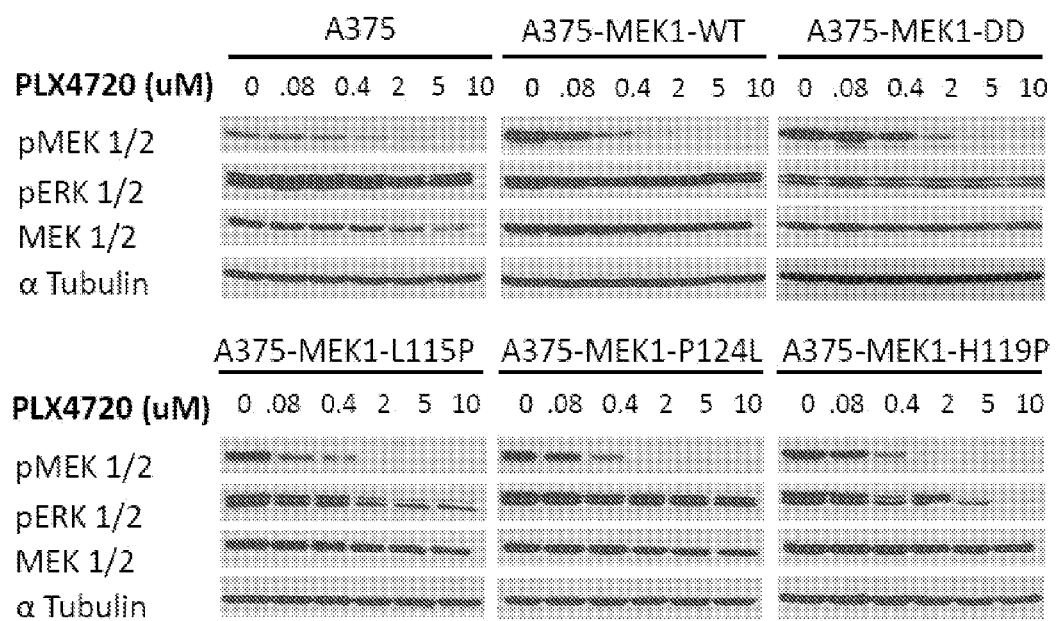
FIG. 7 depicts the level of pERK1/2, pMEK1/2, MEK1/2 and α-tubulin in A375 cells expressing resistant MEK1 alleles following a 16-hour incubation with PLX4720 at 10 µM, 5 µM, 2 µM, 0.4 µM, 0.08 µM and 0 µM.

To determine if MEK1 mutations might confer cross-resistance to RAF inhibition, we examined the effects of the selective B-RAF inhibitor PLX4720 in the cultured melanoma lines described above. AZD6244-resistant primary melanoma cells (M307) demonstrated profound resistance to PLX4720, with a GI$_{50}$ value of >20 μM compared to 50-70 nM in treatment-naïve lines (FIG. 5d). These findings were reflected in biochemical studies of MEK phosphorylation (pMEK) following B-RAF inhibition (FIG. 5e). Expression of several MEK1 resistance alleles in A375 cells modestly increased PLX4720 GI$_{50}$ levels by 3-4 fold, despite comparable levels of p-MEK reduction by this compound (FIG. 5f and Table 3). Interestingly, the constitutively active MEK-DD variant conferred robust resistance to PLX4720, indicating a specific dependency on RAF-activated MEK activity in BRAF$^{V600E}$ melanoma (FIG. 7). Thus, MEK resistance alleles may confer some cross-resistance to RAF inhibition in MAP kinase-dependent cancer cells.

Example 5

Suppression of the Emergence of Drug-Resistant Variants

Whether the stringency of MAP kinase pathway inhibition might influence the emergence of on-target resistance variants in cells harboring a MAP kinase oncogene dependency was next examined. A375 melanoma cells expressing either wild-type MEK1 or a library of MEK1-mutant cDNAs (described above) were cultured for 4 weeks in the presence of AZD6244 or PLX4720 (1.5 μM) singly or in combination. As expected, exposure to AZD6244 completely suppressed the growth of A375 cells expressing wild-type MEK1, whereas AZD6244-resistant clones emerged on plates containing mutagenized MEK1-expressing cells (FIG. 5g). PLX4720-resistant clones emerged from both wild-type and mutant MEK1-expressing cells under these conditions. Notably, simultaneous exposure to both AZD6244 and PLX4720 completely suppressed the emergence of resistant variants (FIG. 5g). Thus, combined RAF and MEK inhibition can help circumvent acquired resistance in MAP kinase-dependent cancers.

Methodology

The following materials and methods were used in connection with the examples. These materials and methods are illustrative only and are not intended to be limiting.

MEK1 Expression Constructs

MEK1 cDNA was cloned into the pWZL-Blast vector by recombinational cloning (Invitrogen) to generate pWZL-Blast-MEK1. Specific mutations were introduced into MEK1 cDNA using QuikChange II Site Directed Mutagenesis (Stratagene).

MEK1 Random Mutagenesis Screen

MEK1 cDNA was cloned in pWZL(Blast) via Gateway cloning technology (Invitrogen). To generate random mutant libraries the plasmid was propagated in E. coli deficient for DNA repair genes MutS, MutD5- and MutT-(XL1-Red, Stratagene), thus introducing random mutations into the plasmid. DNA extracted from the bacteria was subsequently transformed into XL1-Blue (Stratagene) to amplify the library. The mutagenized MEK1 plasmid or non-mutagenized control was used to infect A375 melanoma cells. After selection with blasticidin, cells were plated on 15-cm dishes and cultured in the presence of MEK inhibitors (AZD6244 or C1-1040; 1.5 μM or 2 μM respectively) for 4 weeks until resistant clones emerged.

To determine the approximate coverage of mutations within the library a parallel experiment was performed using the pDNR-1r-SacB vector. Expression of SacB is lethal in sucrose containing media. The vector was replicated in XL1-red following manufacturers protocol. Following transformation bacteria was plated in triplicate +/− sucrose at different dilutions. Colonies were then quantified to infer a frequency of mutation (number of colonies−sucrose/number of colonies+sucrose). The frequency determined by this method is an underestimate: stop codons are most scored, and silent and non-deleterious mutations cannot be detected. One can assume the actual mutation rate would approach a value 4 times greater than scored with this assay. The number of MEK1 containing *E. coli* was quantified per 15 cm plate, then the number of plates to generate the library was calculated to generate coverage of approximately 60×, meaning each base had the potential to be mutated 60 individual occasions within the library as a whole. This was achieved by harvesting bacteria from 40×15 cm plates (~54 000 colonies per plate).

MEK1 Polymerase Chain Reaction

MEK 1 exon 3 was amplified using forward primer 5'-CTTTCATCCCTTCCTCCCTC-3 (SEQ ID NO: 5) and reverse primer 5'-CACCTCCCAGACCAAAGATTAG-3' (SEQ ID NO: 6). MEK1 exon 6 was amplified using 10-20 ng of genomic DNA, forward primer 5'-CTTCTCTTC-CCCAATCTACCTGTG-3 (SEQ ID NO: 7)' and reverse primer 5'-CCTACCCAGCACAAGACTCTG-3 (SEQ ID NO: 8). For each exon, thermocycling reactions were as follows; 95° C./5 minutes, followed by 30 cycles of (95° C./15 seconds, 52° C./20 seconds, 68° C./30 seconds), followed by 68° C./10 minutes. MEK1 cDNA was amplified using forward primer 5'-CGATCCTCCCTTTATCCAGCCCT-CACTCCTTCTCTAGG-3' (SEQ ID NO: 9) and reverse primer 5°-GAGGCCAGCATCGGTTGGTGTG-3' (SEQ ID NO: 10). Thermocyling reactions were 95° C./5 minutes, 35×(95° C./15 seconds, 66° C./60 seconds, 68° C./90 seconds), 68° C./10 minutes. All reactions were performed using pfx polymerase (Invitrogen).

Sequencing of Mek1 DNA

AZD6244 or CI-1040-resistant cells emerging from the random mutagenesis screens were pooled and genomic DNA was prepared (Qiagen DNeasy). MEK1 cDNA was amplified from genomic DNA using primers specific to flanking vector sequence at the 5' and 3' end. In separate experiments, genomic DNA was prepared from melanoma tumor samples, and PCR was performed using intronic primers that amplified exons 3 and 6 from MEK1. PCR products were gel purified, pooled and subjected to single molecule sequencing using an Illumina 3G instrument according to the manufacturer's instructions. Sequence reads (2-3 million 36-base pair sequences per lane) were filtered based on quality metrics and assigned a variant score according to the manufacturer's instructions.

Analysis of Massively-Parallel Sequencing

Raw data from massively-parallel sequencing lanes (Illumina) were analyzed using a "next-generation" sequencing analysis pipeline. Output from data files representing the nucleotide sequence, per-base quality measure, variants detected and alignment to cDNA reference sequence (as determined by alignment with the ELAND algorithm) were integrated and processed for each run. Coverage (i.e., the number of fragments including each base of the cDNA reference) was determined for all bases, and variant alleles were mapped from individual DNA fragments onto the reference sequence. Frequency of variation for each non-wild type allele was determined, and an 'average variant score' was calculated as the average of all quality scores for the position and variant allele in question. All coding mutations were translated to determine amino acid variation, if any, and data for high-frequency (>0.5%), high-quality (AVS>7) mutations were loaded into the CCGD results database.

Patients and Samples

Pre-treatment and post-relapse metastatic melanoma samples were obtained from patients enrolled on a Phase II clinical trial of AZD6244[5]. All patients were consented according to the approved biobanking IRB protocol (University of Zurich, no. 647) prior to biopsy.

Cell Lines and Primary Melanoma Cultures

A375 melanoma cells and 293T retroviral producer cells (ATCC) were cultured in DMEM (MediaTech) with 10% fetal bovine serum (Gemini). A primary culture (M307) derived from an AZD6244-resistant metastatic tumor was generated by treating fresh biopsy material with Dispase for 4 hours and collagenase for 3 hours at 37° C. Cells were washed (phosphate-buffered saline) and seeded into RPMI medium (MediaTech) supplemented with 10% fetal calf serum. Treatment-naïve BRAFV600E melanoma primary cultures (WM3482 and WM3457) were kindly provided by Dr. M. Herlyn (Wistar Institute) and cultured in RPMI, 10% fetal bovine serum and 1% penicillin plus streptomycin.

Retroviral Infections 293T cells (70% confluent) were transfected with pWZL-Blast-MEK1 and pCL-Ampho packaging vector using Lipofectamine 2000 (Invitrogen). Supernatants containing virus were passed through a 0.45 μm syringe. A375 cells were infected for 16 hr with virus together with polybrene (4 μg/ml, Sigma). The selective marker blasticidin (3 μg/ml) was introduced 48 hours post infection.

Pharmacologic Studies

CI-1040 was purchased from Shanghai Lechen International Trading Company; AZD6244 was purchased from Selleck Chemicals Co., Ltd., and PLX4720 was purchased from Symansis, Inc. For growth inhibition analysis, cultured melanoma cells were seeded in 96-well plates (5000 cells/well, or 3000 cells/well for A375 cells) and allowed to adhere for 16 hr. Afterwards, media containing serial dilutions of MEK or RAF inhibitor were added, ensuring that the final volume of DMSO did not exceed 1%. Cells were incubated for 96 hours in the presence of drug, and viability was measured by the CellTiter-Glo assay (Promega). Curves and $GI_{50}$ values were generated from the composite of three independent experiments, 6 replicates per experiment.

Pharmacological Growth Inhibition Assays

Cultured cells were seeded in 96-well plates at a density of 5000 cells/well for all cell lines, with the exception of A375, where 3000 cells were seeded. Following adherence of the cells, usually an overnight period was allowed for this, serial dilutions of a compound were performed 100 fold in DMSO, then transferred to cells accordingly to yield dilutions ranging from 100 μM to $1\times10^6$ μM, ensuring the final volume of DMSO did not exceed 1%. Compounds used included the MEK inhibitors CI-1040 (purchased from Shanghai Lechen International Trading Co), and AZD6244 (purchased from Selleck Chemicals Co., Ltd.) and the BRAF inhibitor PLX4720 (purchased from Symansis). Following addition of a drug, cells were incubated for 96 hours. Subsequently cell viability was measured using the CellTiter-Glo viability assay (Promega). Viability was calculated as a percentage of the control (untreated cells) after background subtraction. A minimal number of three replicates were made for each cell line and drug combination experiment, and the entire experiment repeated 3 times. The data from the phaunacologic growth-inhibition assays were modeled using a nonlinear regression curve fit with a sigmoidal dose response. These curves were displayed using GraphPad Prism 5 for Windows (GraphPad Software). The $GI_{50}$ was calculated by determining the slope of the line connecting the data points which flanked the 50% point. The $GI_{50}$ of each MEK allele was compared to A375 using two-sample Student's T-test, and M302 was compared to treatment naïve short term cultures. $H_A$ (alternative hypothesis) was used; mean $GI_{50}$ greater than mean $GI_{50}$ of A375 or naïve short term culture, $\alpha$=0.05, one-sided test. All P-value calculations were performed using MATLAB Statistics Toolbox (MATLAB Version 7.1), the MathWorks, Inc.

Western Blot Analysis

Immunoblot studies were performed using standard procedures. Briefly, melanoma cells were lysed with TNN buffer containing protease inhibitor (Roche), NaF and NaV0$_3$ (1 mM each). Lysates were quantified (Bradford assay), denatured (95° C.), and resolved by SDS gel electrophoresis. Protein was transferred to nitrocellulose membranes and probed with primary antibodies recognizing p-ERK1/2, p-MEK1/2 (Ser217/221), MEK1/2 and α-tubulin (Cell Signaling Technology; 1:1000 dilution). After incubation with the appropriate secondary antibody (anti-rabbit or anti-mouse IgG, HRP-linked; 1:1000 dilution) (Cell Signaling Technology), proteins were detected using chemiluminescence (Pierce). Biochemical effects of MEK or RAF inhibition were assessed by Western blot analysis of cell lysates collected following 16 hr exposure to drug at varying concentrations.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes can be made to the above-described examples and embodiments, without departing from the intended spirit and scope of the invention as recited in the following claims. It is intended that all such additions, deletions, modifications and other changes be included within the scope of the following claims.

---

What is claimed is:

1. A method of optimizing treatment of a subject having cancer, comprising:
   (a) extracting nucleic acid from cells of the cancer;
   (b) assaying a nucleic acid molecule encoding a MEK polypeptide and identifying the nucleotide sequence of a nucleic acid molecule encoding a MEK polypeptide to identify an alteration of an amino acid residue at one or more amino acids of the encoded MEK polypeptide that confers resistance to a MEK inhibitor and identifying the presence of nucleotides that alter the identity of an amino acid residue at one or more amino acids of the encoded MEK polypeptide relative to the amino acid at one or more positions selected from the group consisting of I103N, I111N, L115R, L115P, H119P, P124L, P124S, F129L and V211D of SEQ ID NO:2, the altered identity of the amino acid residue at one or more amino acids of the encoded MEK polypeptide confers resistance to a MEK inhibitor and indicates a need to treat the subject with a MEK inhibitor and a RAF inhibitor; and
   (c) administering a MEK inhibitor and a RAF inhibitor to the subject when the nucleic acid molecule includes nucleotides that alter the identity of an amino acid residue at one or more amino acid of the encoded MEK polypeptide relative to the amino acid at one or more positions selected from the group consisting I103N, I111N, L115R, L115P, H119P, P124L, P124S, F129L and V211D of SEQ ID NO:2, and the altered identity of the amino acid residue at one or more amino acids of the encoded MEK polypeptide confers resistance to a MEK inhibitor.

2. A method of treating a subject having cancer, comprising:
   (a) assaying a nucleic acid molecule of the cancer encoding a MEK polypeptide and identifying the nucleotide sequence of a nucleic acid molecule encoding a MEK polypeptide to identify an alteration of an amino acid residue at one or more amino acids of the encoded MEK polypeptide that confers resistance to a MEK inhibitor and identifying the presence of nucleotides that alter the identity of an amino acid residue at one or more amino acids of the encoded MEK polypeptide relative to the amino acid at one or more positions selected from the group consisting of I103N, I111N, L115R, L115P, H119P, P124L, P124S, F129L and V211D of SEQ ID NO:2, the altered identity of the amino acid residue at one or more amino acids of the encoded MEK polypeptide confers resistance to a MEK inhibitor and indicates a need to treat the subject with a MEK inhibitor and a RAF inhibitor;
   (b) selecting a subject for treatment with a MEK inhibitor and a RAF inhibitor on the basis of the subject having a nucleic acid molecule encoding a MEK polypeptide having an alteration of an amino acid residue at one or more amino acids of the encoded MEK polypeptide that confers resistance to a MEK inhibitor; and
   (c) administering a MEK inhibitor and a RAF inhibitor to the subject when the nucleic acid molecule includes nucleotides that alter the identity of an amino acid residue at one or more amino acid of the encoded MEK polypeptide relative to the amino acid at one or more positions selected from the group consisting of I103N, I111N, L115R, L115P, H119P, P124L, P124S, FLF129L and V211D of SEQ ID NO:2, and the altered identity of the amino acid residue at one or more amino acids of the encoded MEK polypeptide confers resistance to a MEK inhibitor.

3. A method of identifying a subject having cancer as having a high risk of relapse during treatment with a first inhibitor comprising a first-generation MEK inhibitor or as being unresponsive to treatment with a first inhibitor comprising a first-generation MEK inhibitor or who is likely to benefit from treatment with a second inhibitor, comprising:
   (a) extracting nucleic acid from cells of the cancer;
   (b) assaying a nucleic acid molecule encoding a MEK polypeptide to identify an alteration of an amino acid residue at one or more amino acids of the encoded MEK polypeptide that confers resistance to a MEK inhibitor and identifying the presence of nucleotides that alter the identity of an amino acid residue at one or more amino acids of the encoded MEK polypeptide relative to the amino acid at one or more positions selected from the group consisting of I103N, I111N, L115R, L115P, H119P, P124L, P124S, F129L and V211D of SEQ ID NO:2, the altered identity of the amino acid residue at one or more amino acids of the encoded MEK polypeptide confers resistance to a MEK inhibitor and identifies the subject as having a high risk of relapse during treatment with a first-generation MEK inhibitor or as being unresponsive to treatment with a first-generation MEK inhibitor or who is likely to benefit from treatment with a second inhibitor; and (c) administering a MEK inhibitor and a RAF inhibitor to the subject when the nucleic acid molecule includes nucleotides that alter the identity of an amino acid residue at one or more amino acid of the encoded MEK polypeptide relative to the amino acid at one or more positions selected from the group consisting I103N, I111N, L115R, L115P, H119P, P124L, P124S, F129L and V211D of SEQ ID NO:2, and the altered identity of the amino acid residue at one or more amino acids of the encoded MEK polypeptide confers resistance to a MEK inhibitor.

4. The method of claim 1, wherein the MEK inhibitor is selected from the group consisting of CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile, and 4-[3-Chloro-4-(1-methyl-1H-imidazol-2-ylsulfanyl)-phenylamino]-6-methoxy-7-(3-morpholin-4-yl-propoxy)-quinoline-3-carbonitrile.

5. The method of claim 1, wherein the RAF inhibitor is selected from the group consisting of PLX4720, PLX4032, BAY 43-9006 (Sorafenib), ZM 336372, RAF 265, AAL-881, LBT-613, and CJS352.

6. The method of claim 1, wherein the cancer is selected from the group consisting of leukemias, lymphomas, myelomas, carcinomas, metastatic carcinomas, sarcomas, adenomas, nervous system cancers and genitourinary cancers.

7. The method of claim 1, wherein the cancer is melanoma.

8. The method of claim 2, wherein the MEK inhibitor is selected from the group consisting of CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile, and 4-[3-Chloro-4-(1-methyl-1H-imidazol-2-ylsulfanyl)-phenylamino]-6-methoxy-7-(3-morpholin-4-yl-propoxy)-quinoline-3-carbonitrile.

9. The method of claim 2, wherein the RAF inhibitor is selected from the group consisting of PLX4720, PLX4032, BAY 43-9006 (Sorafenib), ZM 336372, RAF 265, AAL-881, LBT-613, and CJS352.

10. The method of claim 2, wherein the cancer is selected from the group consisting of leukemias, lymphomas, myelomas, carcinomas, metastatic carcinomas, sarcomas, adenomas, nervous system cancers and genitourinary cancers.

11. The method of claim 2, wherein the cancer is melanoma.

12. The method of claim 2, wherein the assay comprises sequencing the nucleic acid or subjecting the sample to PCR.

13. The method of claim 3, wherein the second inhibitor comprises a RAF inhibitor.

* * * * *

UNITED STATES PATENT AND TRADEMARK OFFICE
CERTIFICATE OF CORRECTION

PATENT NO. : 9,084,781 B2  
APPLICATION NO. : 13/139060  
DATED : July 21, 2015  
INVENTOR(S) : Levi A. Garraway et al.

Page 1 of 1

It is certified that error appears in the above-identified patent and that said Letters Patent is hereby corrected as shown below:

In the Claims

In column 75, claim 1, line 48, before "when the nucleic acid" replace "subiect" with --subject--.

In column 76, claim 2, line 49, before "and V211D" replace "FLF129L" with --F129L--.

Signed and Sealed this  
Thirty-first Day of May, 2016

Michelle K. Lee  
*Director of the United States Patent and Trademark Office*

SEQUENCE LISTING

<160> NUMBER OF SEQ ID NOS: 10

<210> SEQ ID NO 1
<211> LENGTH: 2603
<212> TYPE: DNA
<213> ORGANISM: Homo sapiens

<400> SEQUENCE: 1

```
aggcgaggct tccccttccc cgcccctccc ccggcctcca gtccctccca gggccgcttc      60
gcagagcggc taggagcacg gcggcggcgg cactttcccc ggcaggagct ggagctgggc     120
tctggtgcgc gcgcggctgt gccgcccgag ccggagggac tggttggttg agagagagag     180
aggaagggaa tcccgggctg ccgaaccgca cgttcagccc gctccgctcc tgcagggcag     240
cctttcggct ctctgcgcgc gaagccgagt cccgggcggg tggggcgggg gtccactgag     300
accgctaccg gcccctcggc gctgacggga ccgcgcgggg cgcacccgct gaaggcagcc     360
ccggggcccg cggcccggac ttggtcctgc gcagcgggcg cggggcagcg cagcgggagg     420
aagcgagagg tgctgccctc ccccgggagt tggaagcgcg ttacccgggt ccaaaatgcc     480
caagaagaag ccgacgccca tccagctgaa cccggccccc gacggctctg cagttaacgg     540
gaccagctct gcggagacca acttggaggc cttgcagaag aagctggagg agctagagct     600
tgatgagcag cagcgaaagc gccttgaggc cttcttacc cagaagcaga aggtgggaga     660
actgaaggat gacgactttg agaagatcag tgagctgggg gctggcaatg gcggtgtggt     720
gttcaaggtc tcccacaagc cttctggcct ggtcatggcc agaaagctaa ttcatctgga     780
gatcaaaccc gcaatccgga accagatcat aagggagctg caggttctgc atgagtgcaa     840
ctctccgtac atcgtgggct tctatggtgc gttctacagc gatggcgaga tcagtatctg     900
catggagcac atggatggag ttctctgga tcaagtcctg aagaaagctg gaagaattcc     960
tgaacaaatt ttaggaaaag ttagcattgc tgtaataaaa ggcctgacat atctgaggga    1020
gaagcacaag atcatgcaca gagatgtcaa gcccctccaac atcctagtca actcccgtgg    1080
ggagatcaag ctctgtgact ttggggtcag cgggcagctc atcgactcca tggccaactc    1140
cttcgtgggc acaaggtcct acatgtcgcc agaaagactc cagggggactc attactctgt    1200 gcagtcagac atctggagca tgggactgtc tctggtagag atggcggttg ggaggtatcc    1260
catccctcct ccagatgcca aggagctgga gctgatgttt gggtgccagg tggaaggaga    1320
tgcggctgag accccaccca ggccaaggac ccccgggagg cccttagct catacggaat    1380 ggacagccga cctcccatgg caattttga gttgttggat tacatagtca acgagcctcc    1440
tccaaaactg cccagtggag tgttcagtct ggaatttcaa gattttgtga ataaatgctt    1500
```

```
aataaaaaac cccgcagaga gagcagattt gaagcaactc atggttcatg cttttatcaa    1560
gagatctgat gctgaggaag tggattttgc aggttggctc tgctccacca tcggccttaa    1620
ccagcccagc acaccaaccc atgctgctgg cgtctaagtg tttgggaagc aacaaagagc    1680
gagtcccctg cccggtggtt tgccatgtcg cttttgggcc tccttcccat gcctgtctct    1740
gttcagatgt gcatttcacc tgtgacaaag gatgaagaac acagcatgtg ccaagattct    1800
actcttgtca tttttaatat tactgtcttt attcttatta ctattattgt tcccctaagt    1860
ggattggctt tgtgcttggg gctatttgtg tgtatgctga tgatcaaaac ctgtgccagg    1920
ctgaattaca gtgaaatttt ggtgaatgtg ggtagtcatt cttacaattg cactgctgtt    1980
cctgctccat gactggctgt ctgcctgtat tttcgggatt ctttgacatt tggtggtact    2040
ttattcttgc tgggcatact ttctctctag gagggagcct tgtgagatcc ttcacaggca    2100
gtgcatgtga agcatgcttt gctgctatga aaatgagcat cagagagtgt acatcatgtt    2160 atttttattat tattatttgc ttttcatgta gaactcagca gttgacatcc aaatctagcc    2220
agagcccttc actgccatga tagctggggc ttcaccagtc tgtctactgt ggtgatctgt    2280
agacttctgg ttgtatttct atatttattt tcagtatact gtgtgggata cttagtggta    2340
tgtctcttta agttttgatt aatgtttctt aaatggaatt attttgaatg tcacaaattg    2400
atcaagatat taaaatgtcg gatttatctt tccccatatc caagtaccaa tgctgttgta    2460
aacaacgtgt atagtgccta aaattgtatg aaaatccttt taaccatttt aacctagatg    2520
tttaacaaat ctaatctctt attctaataa atatactatg aaataaaaaa aaaaggatga    2580
aagctaaaaa aaaaaaaaaa aaa                                             2603
```

<210> SEQ ID NO 2
<211> LENGTH: 393
<212> TYPE: PRT
<213> ORGANISM: Homo sapiens

<400> SEQUENCE: 2

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175
```

```
Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 3
<211> LENGTH: 1759
<212> TYPE: DNA
<213> ORGANISM: Homo sapiens

<400> SEQUENCE: 3
cccctgcctc tcggactcgg gctgcggcgt cagccttctt cgggcctcgg cagcggtagc      60
ggctcgctcg cctcagcccc agcgcccctc ggctaccctc ggcccaggcc cgcagcgccg     120
cccgccctcg gccgccccga cgccggcctg ggccgcggcc gcagcccgg gctcgcgtag     180 gcgccgaccg ctcccggccc gcccctatg ggccccggct agaggcgccg ccgccgccgg     240
cccgcggagc cccgatgctg gcccggagga agccggtgct gccggcgctc accatcaacc     300
ctaccatcgc cgagggccca tcccctacca gcgagggcgc ctccgaggca aacctggtgg     360
acctgcagaa gaagctggag gagctggaac ttgacgagca gcagaagaag cggctggaag     420 ccttctcac ccagaaagcc aaggtcggcg aactcaaaga cgatgacttc gaaaggatct     480
cagagctggg cgcgggcaac ggcggggtgg tcaccaaagt ccagcacaga ccctcgggcc     540
tcatcatggc caggaagctg atccaccttg agatcaagcc ggccatccgg aaccagatca     600
tccgcgagct gcaggtcctg cacgaatgca actcgccgta catcgtgggc ttctacgggg     660
ccttctacag tgacggggag atcagcattt gcatggaaca catggacggc ggctccctgg     720
accaggtgct gaaagaggcc aagaggattc cgaggagat cctggggaaa gtcagcatcg     780
cggttctccg gggcttggcg tacctccgag agaagcacca gatcatgcac cgagatgtga     840
agccctccaa catcctcgtg aactctagag gggagatcaa gctgtgtgac ttcggggtga     900
```

-continued

```
gcggccagct catcgactcc atggccaact ccttcgtggg cacgcgctcc tacatggctc    960
cggagcggtt gcagggcaca cattactcgg tgcagtcgga catctggagc atgggcctgt   1020
ccctggtgga gctggccgtc ggaaggtacc ccatccccc gcccgacgcc aaagagctgg    1080
aggccatctt tggccggccc gtggtcgacg gggaagaagg agagcctcac agcatctcgc   1140
ctcggccgag gccccgggg cgccccgtca gcggtcacgg gatggatagc cggcctgcca    1200
tggccatctt tgaactcctg gactatattg tgaacgagcc acctcctaag ctgcccaacg   1260
gtgtgttcac ccccgacttc caggagtttg tcaataaatg cctcatcaag aacccagcgg   1320
agcgggcgga cctgaagatg ctcacaaacc acaccttcat caagcggtcc gaggtggaag   1380
aagtggattt tgccggctgg ttgtgtaaaa ccctgcggct gaaccagccc ggcacaccca   1440
cgcgcaccgc cgtgtgacag tggccgggct ccctgcgtcc cgctggtgac ctgcccaccg   1500
tccctgtcca tgccccgccc ttccagctga ggacaggctg gcgcctccac ccaccctcct   1560 gcctcaccc tgcggagagc accgtggcgg ggcgacagcg catgcaggaa cgggggtctc   1620
ctctcctgcc cgtcctggcc ggggtgcctc tggggacggg cgacgctgct gtgtgtggtc   1680
tcagaggctc tgcttcctta ggttacaaaa caaacaggg agagaaaaag caaaaaaaaa    1740
aaaaaaaaaa aaaaaaaaa                                                1759
```

<210> SEQ ID NO 4
<211> LENGTH: 400
<212> TYPE: PRT
<213> ORGANISM: Homo sapiens

<400> SEQUENCE: 4

```
Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
    130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220
```

```
Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400

<210> SEQ ID NO 5
<211> LENGTH: 20
<212> TYPE: DNA
<213> ORGANISM: Artificial Sequence
<220> FEATURE:
<223> OTHER INFORMATION: Synthetic forward primer for MEK 1 exon 3

<400> SEQUENCE: 5
ctttcatccc ttcctccctc                                              20

<210> SEQ ID NO 6
<211> LENGTH: 22
<212> TYPE: DNA
<213> ORGANISM: Artificial Sequence
<220> FEATURE:
<223> OTHER INFORMATION: Synthetic reverse primer for MEK 1 exon 3

<400> SEQUENCE: 6
cacctcccag accaaagatt ag                                           22

<210> SEQ ID NO 7
<211> LENGTH: 24
<212> TYPE: DNA
<213> ORGANISM: Artificial Sequence
<220> FEATURE:
<223> OTHER INFORMATION: Synthetic forward primer for MEK1 exon 6

<400> SEQUENCE: 7
cttctcttcc ccaatctacc tgtg                                         24

<210> SEQ ID NO 8
<211> LENGTH: 21
<212> TYPE: DNA
<213> ORGANISM: Artificial Sequence
<220> FEATURE:
<223> OTHER INFORMATION: Synthetic reverse primer for MEK1 exon 6
```

```
<400> SEQUENCE: 8
cctacccagc acaagactct g                                              21

<210> SEQ ID NO 9
<211> LENGTH: 38
<212> TYPE: DNA
<213> ORGANISM: Artificial Sequence
<220> FEATURE:
<223> OTHER INFORMATION: Synthetic forward primer for MEK1 cDNA

<400> SEQUENCE: 9
cgatcctccc tttatccagc cctcactcct tctctagg                            38

<210> SEQ ID NO 10
<211> LENGTH: 22
<212> TYPE: DNA
<213> ORGANISM: Artificial Sequence
<220> FEATURE:
<223> OTHER INFORMATION: Synthetic reverse primer for MEK1 cDNA

<400> SEQUENCE: 10
gaggccagca tcggttggtg tg                                             22
```